US010470661B2

(12) United States Patent
Garcia et al.

(10) Patent No.: US 10,470,661 B2
(45) Date of Patent: Nov. 12, 2019

(54) TRANSCUTANEOUS ANALYTE SENSORS AND MONITORS, CALIBRATION THEREOF, AND ASSOCIATED METHODS

(71) Applicant: DexCom, Inc., San Diego, CA (US)

(72) Inventors: Arturo Garcia, Chula Vista, CA (US); Peter C. Simpson, Cardiff, CA (US); Apurv Ullas Kamath, San Diego, CA (US); Naresh C. Bhavaraju, San Diego, CA (US); Stephen J. Vanslyke, Carlsbad, CA (US)

(73) Assignee: DexCom, Inc., San Diego, CA (US)

( * ) Notice: Subject to any disclaimer, the term of this patent is extended or adjusted under 35 U.S.C. 154(b) by 193 days.

(21) Appl. No.: 15/261,816

(22) Filed: Sep. 9, 2016

(65) Prior Publication Data

US 2017/0071511 A1    Mar. 16, 2017

Related U.S. Application Data

(63) Continuation of application No. 15/261,711, filed on Sep. 9, 2016, which is a continuation of application No. PCT/US2016/050814, filed on Sep. 8, 2016.

(60) Provisional application No. 62/216,926, filed on Sep. 10, 2015.

(51) Int. Cl.
*A61B 5/00* (2006.01)
*A61B 5/145* (2006.01)
*A61B 5/1495* (2006.01)
*A61B 5/11* (2006.01)

(52) U.S. Cl.
CPC .......... *A61B 5/0031* (2013.01); *A61B 5/1495* (2013.01); *A61B 5/14532* (2013.01); *A61B 5/7246* (2013.01); *A61B 5/743* (2013.01); *A61B 5/1118* (2013.01); *A61B 5/14503* (2013.01); *A61B 2560/0223* (2013.01); *A61B 2560/0228* (2013.01)

(58) Field of Classification Search
CPC .......................... A61B 5/0031; A61B 5/14532
USPC .......................................................... 702/85
See application file for complete search history.

(56) References Cited

U.S. PATENT DOCUMENTS

| | | | |
|---|---|---|---|
| 8,880,371 B2 | 11/2014 | Beyer et al. | |
| 9,033,878 B2 | 5/2015 | Liang et al. | |
| 9,211,092 B2 | 12/2015 | Bhavaraju et al. | |
| 9,943,256 B2 | 4/2018 | Varsavsky et al. | |
| 2008/0039702 A1 | 2/2008 | Hayter et al. | |
| 2008/0200789 A1 | 8/2008 | Brister et al. | |
| 2009/0137887 A1* | 5/2009 | Shariati | A61B 5/0031 600/345 |

(Continued)

FOREIGN PATENT DOCUMENTS

| | | |
|---|---|---|
| EP | 2727530 A1 | 5/2014 |
| WO | WO 2005-057168 | 6/2005 |

(Continued)

*Primary Examiner* — Ricky Ngon
(74) *Attorney, Agent, or Firm* — Knobbe Martens Olson & Bear, LLP

(57) ABSTRACT

Systems and methods are provided to calibrate an analyte concentration sensor within a biological system, generally using only a signal from the analyte concentration sensor. For example, at a steady state, the analyte concentration value within the biological system is known, and the same may provide a source for calibration. Similar techniques may be employed with slow-moving averages. Variations are disclosed.

24 Claims, 49 Drawing Sheets

(56) References Cited

U.S. PATENT DOCUMENTS

2009/0178459 A1* 7/2009 Li ..................... A61B 5/0031
                                                          73/1.02
2014/0278189 A1  9/2014 Vanslyke et al.
2015/0005601 A1  1/2015 Hoss et al.

FOREIGN PATENT DOCUMENTS

| WO | WO 2012-142502 | 10/2012 |
| WO | WO 2013-138369 | 9/2013 |
| WO | WO 2014-158327 | 10/2014 |

* cited by examiner

TRANSCUTANEOUS ANALYTE SENSORS AND MONITORS, CALIBRATION THEREOF, AND ASSOCIATED METHODS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/261,711, filed on Sep. 9, 2016, which is a continuation, under 35 U.S.C. § 120, of International Patent Application No. PCT/US2016/050814, filed on Sep. 8, 2016 under the Patent Cooperation Treaty (PCT), which designates the United States and claims the benefit of U.S. Provisional Application No. 62/216,926, filed Sep. 10, 2015. Each of the aforementioned applications is incorporated by reference herein in its entirety, and each is hereby expressly made a part of this specification.

TECHNICAL FIELD

Systems and methods for processing sensor data from continuous analyte sensors and for calibration of the sensors.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are spread so far apart that the person with diabetes likely finds out too late of a hyperglycemic or hypoglycemic condition, sometimes incurring dangerous side effects. Glucose levels may be alternatively monitored continuously by a sensor system including an on-skin sensor assembly. The sensor system may have a wireless transmitter which transmits measurement data to a receiver which can process and display information based on the measurements.

Heretofore, a variety of glucose sensors have been developed for continuously measuring glucose values. Many implantable glucose sensors suffer from complications within the body and provide only short-term and less-than-accurate sensing of blood glucose. Similarly, transdermal sensors have run into problems in accurately sensing and reporting back glucose values continuously over extended periods of time. Some efforts have been made to obtain blood glucose data from implantable devices and retrospectively determine blood glucose trends for analysis; however these efforts do not aid the diabetic in determining real-time blood glucose information. Some efforts have also been made to obtain blood glucose data from transdermal devices for prospective data analysis, however similar problems have occurred.

In a continuous glucose monitor (CGM), after the sensor is implanted, it is calibrated, after which it provides substantially continuous sensor data to the sensor electronics. The sensor electronics convert the sensor data so that estimated analyte values can be continuously provided to the user. As used herein, the terms "substantially continuous," "continuously," etc., may refer to a data stream of individual measurements taken at time-spaced intervals, which may range from fractions of a second up to, for example, 1, 2, or 5 minutes or more. As the sensor electronics continue to receive sensor data, the sensor may be occasionally recalibrated to account for possible changes in sensor sensitivity and/or baseline (drift). Sensor sensitivity may refer to an amount of electrical current produced in the sensor by a predetermined amount of the measured analyte.

Sensor baseline refers to a signal output by the sensor when no analyte is detected. Over time, sensitivity and baseline change due to a variety of factors, including cellular attack or migration of cells to the sensor, which can affect the ability of the analyte to reach the sensor.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

Without limiting the scope of the present embodiments as expressed by the claims that follow, prominent features of systems and methods according to present principles will be discussed briefly. After considering this discussion, and particularly after reading the section entitled "Detailed Description," one will understand how the features of the present embodiments provide the advantages described herein.

In a first aspect, a method is provided of calibrating an analyte concentration sensor within a biological system, using only a signal from the analyte concentration sensor, where at an occurrence of a repeatable event, the analyte concentration value within the biological system is known, including: on a monitoring device, detecting when an analyte concentration value as measured by an analyte concentration sensor indwelling in a biological system constitutes a first repeatable event; and on the monitoring device or on a device or server operatively coupled to the monitoring device, correlating a measurement of the analyte concentration value when the biological system is at the detected first repeatable event to the known analyte concentration value.

Implementations of the embodiments and aspects may include one or more of the following. The correlating may include determining a functional relationship between the sensor reading and the known analyte concentration value. The functional relationship may include a multiplicative constant. The detecting may include waiting a predetermined time following entry of an event on the monitoring device, such as meal or exercise. The method may further include, following the correlating, detecting the occurrence of a second repeatable event, the second repeatable event different from the first repeatable event; and recalibrating the analyte concentration sensor by correlating a sensor reading when the biological system is at the detected second repeatable event to the known analyte concentration value. The sensor reading may have a first raw value at initial calibration and a second raw value at re-calibration, where the first and second raw values are different. The method may further include, following the correlating, displaying a graph or table indicating currently measured and historic values of the analyte concentration as calibrated based at least in part on the correlating; and, following the recalibration, updating the display of the graph or table indicating currently measured and historic values of the analyte concentration according to the recalibration. The updating may change the display of the historic values of the analyte concentration. The method may further include determining a difference between the first and second raw value; comparing a quantity based on the difference to a predetermined criteria, and based on the comparing, determining if the sensor calibration has drifted. The method may further include determining a quantitative amount that the sensor calibration has drifted. The method may further include adjusting the sensor calibration based on the determined quantitative amount. The quantity may be the slope between the first and second raw value. The method may further include, if the slope exceeds a predetermined threshold, prohibiting future calibrations based on steady-state until the slope no longer exceeds a predetermined threshold. The method may further include prompting the user to enter a measured value. The sensor may be a glucose sensor. The method may further include, subsequent to the correlating, receiving a signal from the sensor; and displaying a value corresponding to the received signal, the displayed value based on the received signal and the known analyte concentration value. The method may further include a step of determining the known analyte concentration value by prompting the user to enter a measured value. The method may further include a step of determining the known analyte concentration value by accessing a population average. Recalibrating may be configured to occur at a time when a sensor reading is substantially stable, or within a predetermined range of readings for threshold period of time, whereby an occurrence of unexpected jumps in readings is reduced, and such recalibrating at such times may be caused or configured to occur in any of the embodiments or aspects described.

In a second aspect, a method is provided of compensating for drift in an analyte concentration sensor within a biological system using only a signal from an analyte concentration sensor, including: measuring values of an analyte using an indwelling analyte concentration sensor; determining a first slow-moving average of the measured values of the analyte over a first period of time, and basing a calibration of the sensor based at least in part on the first slow-moving average; following the first determining, determining a second slow-moving average of the measured values of the analyte over a second period of time; and adjusting the calibration of the sensor based at least in part on the difference between the first slow moving average and the second slow moving average.

Implementations of the aspects and embodiments may include one or more of the following. The duration of the first period of time may be greater than about 12 hours or greater than about 24 hours. A duration of the first period of time may be the same as a duration of the second period of time. The method may further include, following the basing the calibration of the sensor based at least in part on the first slow-moving average, displaying a graph or table indicating at least historic values of the analyte concentration as calibrated based at least in part on the first slow-moving average; and following the adjusting, updating the display of the graph or table indicating at least historic values of the analyte concentration according to the adjusted calibration. The updating may change the display of the historic values of the analyte concentration. The displayed graph or table may further indicate currently measured values of the analyte concentration. The basing a calibration of the sensor based at least in part on the first slow-moving average may further include basing the calibration on a seed value, such as a seed value received from a population average or from a prior session. The method may further include, following the adjusting, changing the seed value based at least in part on the adjusting. The method may further include changing the seed value based on the difference between the first slow-moving average and the second slow moving average.

In a third aspect, a method is provided of compensating for drift in an analyte concentration sensor within a biological system using only a signal from an analyte concentration sensor, including: measuring values of an analyte using an indwelling analyte concentration sensor; determining a first slow-moving average of the measured values of the analyte over a first period of time, and basing a first apparent sensitivity of the sensor based at least in part on the first slow-moving average; following the first determining, determining a second slow-moving average of the measured values of the analyte over a second period of time, and basing a second apparent sensitivity of the sensor based at least in part on the second slow moving average; determining if a change in apparent sensitivity of the sensor between the first apparent sensitivity and the second apparent sensitivity matches predetermined criteria; if the change in apparent sensitivity matches predetermined criteria, then adjusting an actual sensitivity of the sensor to an adjusted value based on a difference between the first and second apparent sensitivities; if the change in apparent sensitivity fails to match predetermined criteria, then prompting the user to enter data, whereby a reason for the change in apparent sensitivity may be determined.

Implementations of the aspects and embodiments may include one or more of the following. The determining may include determining if the change in apparent sensitivity is due to sensitivity drift or a change in the slow-moving average. If the change in apparent sensitivity is due to a change in the slow-moving average, then the method may further include prompting the user to enter data pertaining to the change. The predetermined criteria may include known behavior for sensitivity changes over time for a sensor. The known behavior for sensitivity changes may constitute an envelope of acceptable sensitivity changes with respect to time. The adjusted value may be based at least in part on the second slow moving average. The predetermined criteria may further include known values for physiologically feasible analyte changes. The prompting the user may include prompting the user to enter a calibration value. The prompting the user may include prompting the user to enter meal or exercise information. Upon receiving the calibration value or the meal or exercise information from the user, the method may further include determining if the change in apparent sensitivity is due to sensitivity drift or a change in the slow-moving average. The method may further include adjusting the actual sensitivity of the sensor based on the received calibration value or meal or exercise information.

In a fourth aspect, a method is provided of checking calibration of an analyte concentration sensor system within a biological system using only a signal from an analyte concentration sensor, including: after an initial calibration, measuring values of an analyte over time using an indwelling analyte concentration sensor; calculating a clinical value of an analyte concentration based on the measured values and the initial calibration; adjusting the initial calibration to an updated calibration, the adjusting based only on the measured values of the analyte over time or a subset thereof; calculating a clinical value of the analyte concentration based on a measured value and the updated calibration.

Implementations of the aspects and embodiments may include one or more of the following. The initial calibration may be based on a population average or data entered by a user. The adjusting may be based on a slow-moving average of the measured values of the analyte over time. The adjusting may be based on a steady-state value of the analyte. The initial calibration may be based on data determined prior to a session associated with the indwelling analyte concentration sensor. The data may be determined a priori, on the bench, or in vitro.

In a fifth aspect, a method is provided of calibrating an analyte concentration sensor within a biological system, using a signal from the analyte concentration sensor, where at a steady state, the analyte concentration value within the biological system is known, including: on a monitoring device, receiving a seed value of a calibration parameter; on the monitoring device, detecting when an analyte concentration value as measured by an analyte concentration sensor indwelling in a biological system is at a steady state; and on the monitoring device or on a device or server operatively coupled to the monitoring device, correlating a measurement of the analyte concentration value when the biological system is at the detected steady state to the known analyte concentration value; subsequent to the correlating, receiving a signal from the sensor; and calculating and displaying a value corresponding to the received signal, the calculated value based on the received signal, the known analyte concentration value, and the seed value.

Implementations of the aspects and embodiments may include one or more of the following. The received seed value may be received from a source including factory calibration information. The method may further include detecting a behavior in the received signal outside of a pre-prescribed parameter; and prompting a user to enter external calibration information. The displayed value may further be based on the external calibration information. The external calibration information may be received from an SMBG or a fingerstick calibration. The method may further include resetting the known calibration value to a new known calibration value, the resetting based at least partially on the external calibration information. The method may further include resetting the seed value to a new seed value, the resetting based at least partially on the external calibration information. The method may further include altering the display based on a determined accuracy of the value. The altering the displaying may include displaying a range rather than a value, or vice versa. The received seed value of a calibration parameter may be a user-entered characterization of disease state. The user entered characterization of disease state may include an indication of type I diabetes, type II diabetes, nondiabetic, or prediabetic. The received seed value of a calibration parameter may be a value based on one or more user-entered blood glucose values. The displaying of a value corresponding to the received signal may include displaying a graph or table indicating currently measured and historic values of the analyte concentration, and further including: detecting that a change in calibration has occurred; adjusting one or more calibration parameters of the analyte concentration sensor according to the change in calibration; and following the adjusting, updating the display of the graph or table indicating currently measured and historic values of the analyte concentration according to the adjusted calibration parameters. The detecting that a change in calibration has occurred may include: detecting a change in a slow-moving average; or detecting a change in the steady state value.

In a sixth aspect, a method is provided of calibrating an analyte concentration sensor, where following sensor insertion in a patient, only parameters based on or derivable from a sensor signal are employed, including: receiving at least an initial value of an analyte concentration and an initial value or initial distribution of values of a sensor sensitivity; following insertion of an analyte concentration sensor, monitoring a signal from the sensor over a duration of time; over the duration of time, calculating a plurality of analyte concentration values based on the monitored sensor signal and the initial value or distribution of values of the sensor sensitivity; determining a distribution of values of the monitored signal over the duration of time; optimizing the initial value or the distribution of values of the sensor sensitivity and the plurality of analyte concentration values to match the distribution of values of the monitored signal; and determining an updated sensitivity based on the optimization.

Implementations of the aspects and embodiments may include one or more of the following. The receiving may be of an initial distribution of values of a sensor sensitivity, and the calculating a plurality of analyte concentration values may be based on the monitored sensor signal and a representative value from the initial distribution of values of the sensor sensitivity. The representative value may be chosen from an average or a midpoint or a median. The determining an updated sensitivity may further include: dividing the representative value by the initial value of the analyte concentration; and updating the value of the sensitivity to be equal to the result of the dividing. The initial value of an analyte population may be a population average, may be entered by the user, or transferred from a prior session. The optimizing may include optimizing a product of the initial value or distribution of values of the sensor sensitivity and the plurality of analyte concentration values. The optimizing a product may include optimizing the product to match the distribution of values of the monitored signal while adjusting parameters of the distribution of values of the sensor sensitivity and the plurality of analyte concentration values to most closely match respective population averages. The receiving may further include receiving an initial distribution of values of a baseline, and the optimizing may further include optimizing the distribution of values of the baseline along with the distribution of values of the sensor sensitivity and the plurality of analyte concentration values to match the distribution of values of the monitored signal. The initial distribution of values of a baseline may follow a normal distribution. At least the initial value of the analyte concentration may be used as part of a seed value input to a slow-moving average filter. The initial distribution of values of a sensor sensitivity may be defined by a normal distribution. The determined distribution of values of the monitored signal may follow a log normal distribution. The duration of time may be one day. The method may further include continuing to determine updated sensitivities based on a prior updated sensitivity and received analyte concentration values. The method may further include detecting a slow moving average of the monitored analyte concentration values. If an absolute value of a change in the slow moving average is greater than a predetermined threshold over a predetermined unit of time, then the method may include prompting a user to enter data. If an absolute value of a change in the slow moving average is greater than a predetermined threshold over a predetermined unit of time, then the method may include determining if the change is due a system error or due to a change in actual sensitivity of the sensor. The determining if the change is due to a system error or due to a change in actual sensitivity of the sensor may include determining if subsequent behavior of the sensitivity is consistent with a known sensitivity profile, including with an envelope of sensitivity curves. If the absolute value of a change in the slow moving average is determined to be due to a change in actual sensitivity of the sensor, then the method may include updating the sensitivity based at least in part on the value of the change in the slow moving average. The determining if the change is due to a system error or due to a change in actual sensitivity of the sensor may include determining if subsequent behavior of the analyte concentration value is consistent with a known envelope of physiological feasibility. If the absolute value of a change in the slow moving average is determined to be due to a system error, then the method may include prompting the user to enter data.

In an seventh aspect, a method is provided of calibrating an analyte concentration sensor within a biological system, using a signal from the analyte concentration sensor, including: receiving or determining a seed value of a calibration parameter relating to an analyte concentration sensor; using the seed value to at least in part determine a calibration of the analyte concentration sensor; and using the analyte concentration sensor, measuring a value of an analyte concentration; and displaying the measured value as calibrated at least in part using the seed value.

Implementations of the aspects and embodiments may include one or more of the following. The receiving or determining may be performed on a monitoring device in operative signal communication with the analyte concentration sensor. The displaying may be performed on the monitoring device or on a mobile device in signal communication with the monitoring device. The displaying the measured value may include displaying a graph or table indicating at least historic values of the analyte concentration, and may further include: detecting that a change in calibration has occurred; adjusting one or more calibration parameters of the analyte concentration sensor according to the detected change in calibration; and following the adjusting, updating the display of the graph or table indicating at least historic values of the analyte concentration according to the adjusted calibration parameter. The updating may change the display of the historic values of the analyte concentration. The seed value may be at least partially based on a code. The code may be entered by a user into a monitoring device. A monitoring device may be configured to receive the code without substantial involvement of the user. The seed value may be at least partially based on an impedance measurement. The seed value may be at least partially based on information associated with a manufacturing lot of the sensor. The seed value may be at least partially based on a population average. The seed value may be at least partially based on an immediate past analyte value of the user.

In an eighth aspect, a method is provided of calibrating and compensating for drift in an indwelling analyte concentration sensor within a biological system, using only a signal from the analyte concentration sensor, where at a steady state, the analyte concentration value within the biological system is known, including: on a monitoring device, detecting when an analyte concentration value as measured by an analyte concentration sensor indwelling in a biological system is at a steady state; on the monitoring device or on a device or server operatively coupled to the monitoring device, correlating a measurement of the analyte concentration value when the biological system is at the detected steady state to the known analyte concentration value; determining a first slow-moving average of the measured values of the analyte over a first period of time, and basing a calibration of the sensor based at least in part on the first slow-moving average and on the known analyte concentration value; following the first determining, determining a second slow-moving average of the measured values of the analyte over a second period of time; and adjusting the calibration of the sensor based at least in part on the difference between the first slow moving average and the second slow moving average.

In a ninth aspect, a method is provided of calibrating a first portion of a lot of sensors where a second portion has been subject to use, including: receiving calibration data from some of the second portion of sensors; and updating one or more calibration parameters of the first portion based on the received data.

Implementations of the aspects and embodiments may include one or more of the following. The updating may be performed prior to the first portion being installed in users. The updating may be performed after the first portion has been installed in users. The updating may be performed by transmitting new or updated calibration parameters over a network to a monitoring device or to a sensor electronics module associated with the sensor. The second portion of sensors may be configured to be calibrated using an a priori calibration. The second portion of sensors may be configured to be calibrated using user data. The second portion of sensors may be configured to be calibrated using an ex vivo bench calibration. The second portion of sensors may be configured to be calibrated using a blood measurement.

In a tenth aspect, a method is provided of compensating for drift in an analyte concentration sensor within a biological system using only a signal from an analyte concentration sensor, including: measuring values as a function of time of an analyte using an indwelling analyte concentration sensor; filtering the measured values using a double exponential smoothing filter; and following the filtering, displaying the filtered measured values against time.

Implementations of the aspects and embodiments may include one or more of the following. The double exponential smoothing filter may be governed by the equations described herein. The subsequent glucose signal as a function of time may be provided by the equations described herein.

In an eleventh aspect, a method is provided of calibrating an analyte concentration sensor within a biological system, using only a signal from the analyte concentration sensor, wherein at or during a repeatable event, the analyte concentration value within the biological system is known, comprising: on a monitoring device, detecting when a set of analyte concentration values as measured by an analyte concentration sensor indwelling in a biological system constitutes a repeatable event; and on the monitoring device or on a device or server operatively coupled to the monitoring device, correlating the set of analyte concentration values at the repeatable event to the known analyte concentration value.

Implementations may include that the repeatable event is selected from the group consisting of: a steady-state, a post prandial rise, a daily high-low glucose spread, a decay rate, or a rate of change.

In a twelfth aspect, a method is provided of compensating for drift in an analyte concentration sensor within a biological system using only a signal from an analyte concentration sensor, comprising: measuring values of an analyte using an indwelling analyte concentration sensor; determining a first slow-moving average of the measured values of the analyte over a first set of periods of time, wherein the first set includes event-based time periods, and basing a calibration of the sensor based at least in part on the first slow-moving average; following the first determining, determining a second slow-moving average of the measured values of the analyte over a second set of periods of time, wherein the second set includes event-based time periods; and adjusting the calibration of the sensor based at least in part on the difference between the first slow moving average and the second slow moving average.

Implementations may include one or more of the following. The first and second event-based time periods may be selected from the group consisting of: a post-prandial time period, a sleeping time period, and a post-breakfast time period.

In a thirteenth aspect, a method is provided of calibrating an analyte concentration sensor within a biological system, comprising: for a set of sensors of a type, determining a sensitivity profile versus time; for an individual sensor of the type, measuring a sensitivity profile; measuring electrical characteristics of a transmitter; and reading an identifier of the sensor and receiving data corresponding to sensitivity of the sensor, and storing the identifier and the received data on the transmitter.

Implementation may include one or more of the following. The set of sensors of a type may correspond to a set of sensors within a lot. The method may further include packaging the individual sensor in the transmitter as a kit. The method may further include coupling the transmitter to a mobile device running a monitoring application. The method may further include calibrating the transmitter and the sensor using the monitoring application. The calibrating may be with respect to the measured electrical characteristics of the transmitter. The monitoring application may be configured to start a sensor session upon a signal from a transmitter, the signal detecting that the transmitter is coupled to a sensor. The transmitter may be configured to start a sensor session when the transmitter detects a coupling to a sensor. The method may further include coupling the transmitter to a mobile device running a monitoring application. The method may further include receiving a representative set of measured analyte values. The method may further include using the received representative set of measured analyte values, or a subset thereof, to determine a seed parameter for a forward filter, a reverse filter, or both. The seed values may be determined using a median signal value, a drift value, or both. Both a forward filter and a reverse filter may be employed, and the method may further include optimizing the seed values to minimize a mean squared error between the two signal filters. The method may further include adjusting a sensitivity and a baseline for the sensor according to a signal based calibration algorithm, the signal based calibration algorithm using an average of the signals from the forward and reverse filters along with a raw sensor signal. The method may further include adjusting the sensitivity and the baseline based on one or more criteria. The criterion may include that a mean glucose value should be consistent with an expected diabetic mean. The criterion may include that a CGM glucose variability should be consistent with a mean glucose level. The method may further include detecting an amount of sensor change, determining that the amount of sensor change is above a threshold criterion, and preventing the display of readings, whereby potentially inaccurate readings are not displayed to a user.

In a fourteenth aspect, a method is provided of compensating for drift in an analyte concentration sensor within a biological system using only a signal from an analyte concentration sensor, comprising: measuring values of an analyte using an indwelling analyte concentration sensor; determining a first slow-moving average of the measured values of the analyte over a first period of time, and basing a calibration of the sensor based at least in part on the first slow-moving average; following the first determining, determining a second slow-moving average of the measured values of the analyte over a second period of time; and adjusting the calibration of the sensor based at least in part on a seed value and on the difference between the first slow moving average and the second slow moving average.

Implementations may include one or more of the following. The seed value may be determined using a median signal value, a drift value, or both. Both a forward filter and a reverse filter may be employed, and the method may further include optimizing seed values to minimize a mean squared error between the two signal filters. The method may further include adjusting a sensitivity and a baseline for the sensor according to a signal based calibration algorithm, the signal based calibration algorithm using an average of the signals from the forward and reverse filters along with a raw sensor signal. The method may further include adjusting the sensitivity and the baseline based on one or more criteria. The criterion may include that a mean glucose value should be consistent with an expected diabetic mean. The criterion may include that a CGM glucose variability should be consistent with a mean glucose level.

In further aspects and embodiments, the above method features of the various aspects are formulated in terms of a system as in various aspects, configured to carry out the method features. Any of the features of an embodiment of any of the aspects, including but not limited to any embodiments of any of the first through fourteenth aspects referred to above, is applicable to all other aspects and embodiments identified herein, including but not limited to any embodiments of any of the first through fourteenth aspects referred to above. Moreover, any of the features of an embodiment of the various aspects, including but not limited to any embodiments of any of the first through fourteenth aspects referred to above, is independently combinable, partly or wholly with other embodiments described herein in any way, e.g., one, two, or three or more embodiments may be combinable in whole or in part. Further, any of the features of an embodiment of the various aspects, including but not limited to any embodiments of any of the first through fourteenth aspects referred to above, may be made optional to other aspects or embodiments. Any aspect or embodiment of a method can be performed by a system or apparatus of another aspect or embodiment, and any aspect or embodiment of a system or apparatus can be configured to perform a method of another aspect or embodiment, including but not limited to any embodiments of any of the first through fourteenth aspects referred to above.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

BRIEF DESCRIPTION OF THE DRAWINGS

The present embodiments now will be discussed in detail with an emphasis on highlighting the advantageous features. These embodiments depict the novel and nonobvious sensor signal processing and calibration systems and methods shown in the accompanying drawings, which are for illustrative purposes only and are not to scale, instead emphasizing the principles of the disclosure. These drawings include the following figures, in which like numerals indicate like parts:

FIG. 35 also illustrates the effect of a double exponential filter operating on the glucose trace.

DETAILED DESCRIPTION

Figure 1:
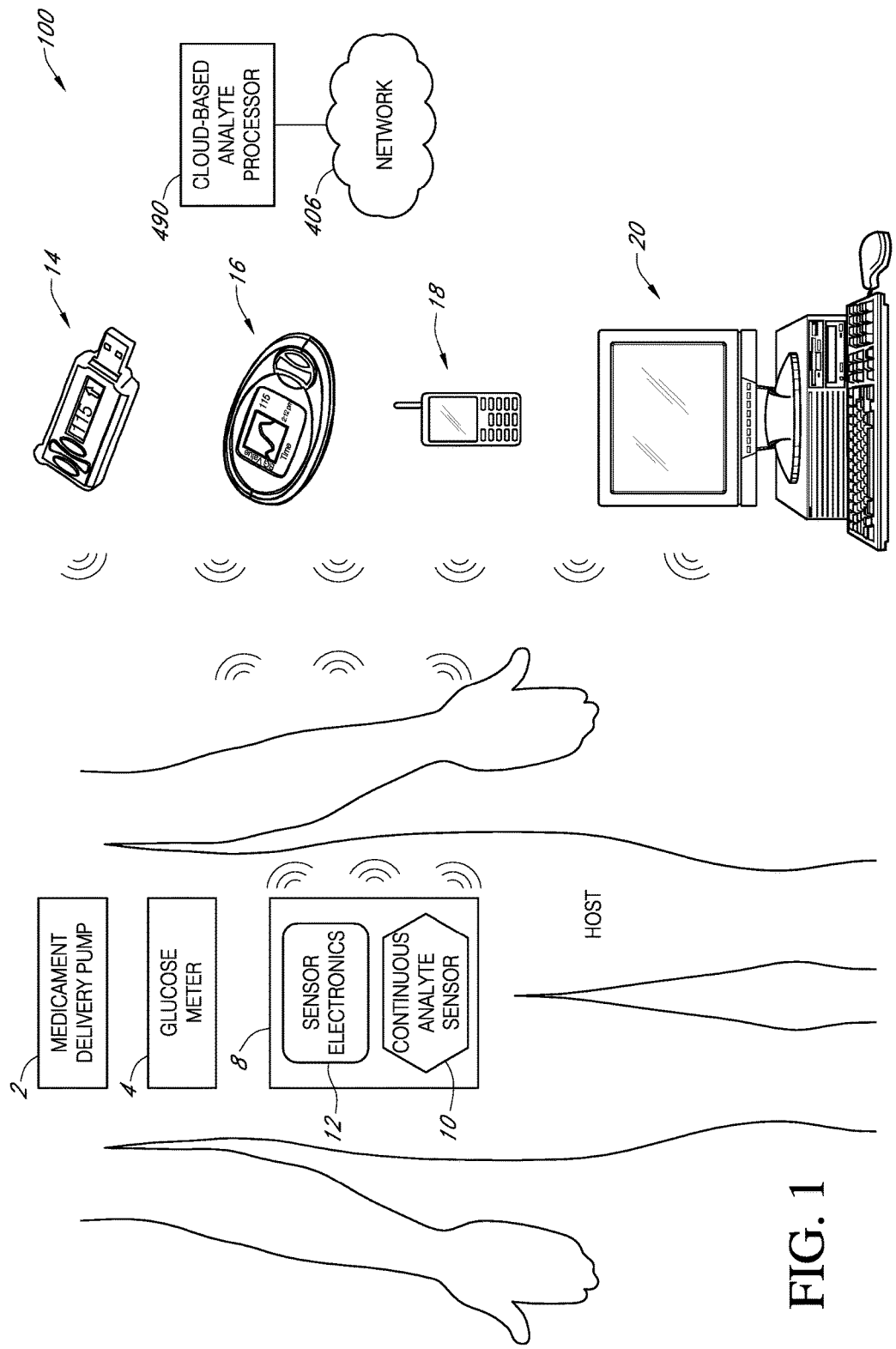
FIG. 1 is a schematic view of a continuous analyte sensor system attached to a host and communicating with a plurality of example devices.

The following description and examples illustrate some example embodiments of the disclosed invention in detail. Those of skill in the art will recognize that there are numerous variations and modifications of this invention that are encompassed by its scope. Accordingly, the description of a certain example embodiment should not be deemed to limit the scope of the present invention.

Definitions

In order to facilitate an understanding of the preferred embodiments, a number of terms are defined below.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-ß hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diphtheria/tetanus antitoxin; erythrocyte arginase; erythrocyte protoporphyrin; esterase D; fatty acids/acylglycines; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *Cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The terms "microprocessor" and "processor" as used herein are broad terms and are to be given their ordinary and customary meaning to a person of ordinary skill in the art (and are not to be limited to a special or customized meaning), and furthermore refer without limitation to a computer system, state machine, and the like that performs arithmetic and logic operations using logic circuitry that responds to and processes the basic instructions that drive a computer.

The terms "raw data stream" and "data stream" as used herein are broad terms and are to be given their ordinary and customary meaning to a person of ordinary skill in the art (and are not to be limited to a special or customized meaning), and furthermore refer without limitation to an analog or digital signal directly related to the measured glucose from the glucose sensor. In one example, the raw data stream is digital data in "counts" converted by an A/D converter from an analog signal (e.g., voltage or amps) and includes one or more data points representative of a glucose concentration. The terms broadly encompass a plurality of time spaced data points from a substantially continuous glucose sensor, which comprises individual measurements taken at time intervals ranging from fractions of a second up to, e.g., 1, 2, or 5 minutes or longer. In another example, the raw data stream includes an integrated digital value, wherein the data includes one or more data points representative of the glucose sensor signal averaged over a time period.

The term "calibration" as used herein is a broad term and is to be given its ordinary and customary meaning to a person of ordinary skill in the art (and is not to be limited to a special or customized meaning), and furthermore refers without limitation to the process of determining the relationship between the sensor data and the corresponding reference data, which can be used to convert sensor data into meaningful values substantially equivalent to the reference data, with or without utilizing reference data in real time. In some embodiments, namely, in continuous analyte sensors, calibration can be updated or recalibrated (at the factory, in real time and/or retrospectively) over time as changes in the relationship between the sensor data and reference data occur, for example, due to changes in sensitivity, baseline, transport, metabolism, and the like. Calibration may also be accomplished by estimating sensor signal parameters automatically through analysis of one or more signal characteristics or features (auto-calibration).

The terms "calibrated data" and "calibrated data stream" as used herein are broad terms and are to be given their ordinary and customary meaning to a person of ordinary skill in the art (and are not to be limited to a special or customized meaning), and furthermore refer without limitation to data that has been transformed from its raw state to another state using a function, for example a conversion function, including by use of a sensitivity, to provide a meaningful value to a user.

The terms "smoothed data" and "filtered data" as used herein are broad terms and are to be given their ordinary and customary meaning to a person of ordinary skill in the art (and are not to be limited to a special or customized meaning), and furthermore refer without limitation to data that has been modified to make it smoother and more continuous and/or to remove or diminish outlying points, for example, by performing a moving average of the raw data stream, including a slow moving average. Examples of data filters include FIR (finite impulse response), IIR (infinite impulse response), moving average filters, and the like.

The terms "smoothing" and "filtering" as used herein are broad terms and are to be given their ordinary and customary meaning to a person of ordinary skill in the art (and are not to be limited to a special or customized meaning), and furthermore refer without limitation to modification of a set of data to make it smoother and more continuous or to remove or diminish outlying points, for example, by performing a moving average of the raw data stream.

The term "algorithm" as used herein is a broad term and is to be given its ordinary and customary meaning to a person of ordinary skill in the art (and is not to be limited to a special or customized meaning), and furthermore refers without limitation to a computational process (for example, programs) involved in transforming information from one state to another, for example, by using computer processing.

The term "counts" as used herein is a broad term and is to be given its ordinary and customary meaning to a person of ordinary skill in the art (and is not to be limited to a special or customized meaning), and furthermore refers without limitation to a unit of measurement of a digital signal. In one example, a raw data stream measured in counts is directly related to a voltage (e.g., converted by an A/D converter), which is directly related to current from the working electrode.

The term "sensor" as used herein is a broad term and is to be given its ordinary and customary meaning to a person of ordinary skill in the art (and is not to be limited to a special or customized meaning), and furthermore refers without limitation to the component or region of a device by which an analyte can be quantified.

The terms "glucose sensor" and "member for determining the amount of glucose in a biological sample" as used herein are broad terms and are to be given their ordinary and customary meaning to a person of ordinary skill in the art (and are not to be limited to a special or customized meaning), and furthermore refer without limitation to any mechanism (e.g., enzymatic or non-enzymatic) by which glucose can be quantified. For example, some embodiments utilize a membrane that contains glucose oxidase that catalyzes the conversion of oxygen and glucose to hydrogen peroxide and gluconate, as illustrated by the following chemical reaction:

Because for each glucose molecule metabolized, there is a proportional change in the co-reactant $O_2$ and the product $H_2O_2$, one can use an electrode to monitor the current change in either the co-reactant or the product to determine glucose concentration.

The terms "operably connected" and "operably linked" as used herein are broad terms and are to be given their ordinary and customary meaning to a person of ordinary skill in the art (and are not to be limited to a special or customized meaning), and furthermore refer without limitation to one or more components being linked to another component(s) in a manner that allows transmission of signals between the components. For example, one or more electrodes can be used to detect the amount of glucose in a sample and convert that information into a signal, e.g., an electrical or electromagnetic signal; the signal can then be transmitted to an electronic circuit. In this case, the electrode is "operably linked" to the electronic circuitry. These terms are broad enough to include wireless connectivity.

The term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, calculating, deriving, establishing and/or the like. Determining may also include ascertaining that a parameter matches a predetermined criteria, including that a threshold has been met, passed, exceeded, and so on.

The term "substantially" as used herein is a broad term and is to be given its ordinary and customary meaning to a person of ordinary skill in the art (and is not to be limited to a special or customized meaning), and furthermore refers without limitation to being largely but not necessarily wholly that which is specified.

The term "host" as used herein is a broad term and is to be given its ordinary and customary meaning to a person of ordinary skill in the art (and is not to be limited to a special or customized meaning), and furthermore refers without limitation to mammals, particularly humans.

The term "continuous analyte (or glucose) sensor" as used herein is a broad term and is to be given its ordinary and customary meaning to a person of ordinary skill in the art (and is not to be limited to a special or customized meaning), and furthermore refers without limitation to a device that continuously or continually measures a concentration of an analyte, for example, at time intervals ranging from fractions of a second up to, for example, 1, 2, or 5 minutes, or longer. In one exemplary embodiment, the continuous analyte sensor is a glucose sensor such as described in U.S. Pat. No. 6,001,067, which is incorporated herein by reference in its entirety.

The term "continuous analyte (or glucose) sensing" as used herein is a broad term and is to be given its ordinary and customary meaning to a person of ordinary skill in the art (and is not to be limited to a special or customized meaning), and furthermore refers without limitation to the period in which monitoring of an analyte is continuously or continually performed, for example, at time intervals ranging from fractions of a second up to, for example, 1, 2, or 5 minutes, or longer.

The terms "reference analyte monitor," "reference analyte meter," and "reference analyte sensor" as used herein are broad terms and are to be given their ordinary and customary meaning to a person of ordinary skill in the art (and are not to be limited to a special or customized meaning), and furthermore refer without limitation to a device that measures a concentration of an analyte and can be used as a reference for the continuous analyte sensor, for example a self-monitoring blood glucose meter (SMBG) can be used as a reference for a continuous glucose sensor for comparison, calibration, and the like.

The term "sensing membrane" as used herein is a broad term and is to be given its ordinary and customary meaning to a person of ordinary skill in the art (and is not to be limited to a special or customized meaning), and furthermore refers without limitation to a permeable or semi-permeable membrane that can be comprised of two or more domains and is typically constructed of materials of a few microns thickness or more, which are permeable to oxygen and may or may not be permeable to glucose. In one example, the sensing membrane comprises an immobilized glucose oxidase enzyme, which enables an electrochemical reaction to occur to measure a concentration of glucose.

The term "physiologically feasible" as used herein is a broad term and is to be given its ordinary and customary meaning to a person of ordinary skill in the art (and is not to be limited to a special or customized meaning), and furthermore refers without limitation to the physiological parameters obtained from continuous studies of glucose data in humans and/or animals. For example, a maximal sustained rate of change of glucose in humans of about 4 to 5 mg/dL/min and a maximum acceleration of the rate of change of about 0.1 to 0.2 mg/dL/min/min are deemed physiologically feasible limits. Values outside of these limits would be considered non-physiological and likely a result of signal error, for example. As another example, the rate of change of glucose is lowest at the maxima and minima of the daily glucose range, which are the areas of greatest risk in patient treatment, thus a physiologically feasible rate of change can be set at the maxima and minima based on continuous studies of glucose data. As a further example, it has been observed that the best solution for the shape of the curve at any point along glucose signal data stream over a certain time period (e.g., about 20 to 30 minutes) is a straight line, which can be used to set physiological limits.

The term "frequency content" as used herein is a broad term and is to be given its ordinary and customary meaning to a person of ordinary skill in the art (and is not to be limited to a special or customized meaning), and furthermore refers without limitation to the spectral density, including the frequencies contained within a signal and their power.

The term "linear regression" as used herein is a broad term and is to be given its ordinary and customary meaning to a person of ordinary skill in the art (and is not to be limited to a special or customized meaning), and furthermore refers without limitation to finding a line in which a set of data has a minimal measurement deviation or separation from that line. Byproducts of this algorithm include a slope, a y-intercept, and an R-Squared value that determine how well the measurement data fits the line. In certain cases, robust regression techniques may also be employed to handle outliers in regression.

The term "non-linear regression" as used herein is a broad term and is to be given its ordinary and customary meaning to a person of ordinary skill in the art (and is not to be limited to a special or customized meaning), and furthermore refers without limitation to fitting a set of data to describe the relationship between a response variable and one or more explanatory variables in a non-linear fashion.

The term "mean" as used herein is a broad term and is to be given its ordinary and customary meaning to a person of ordinary skill in the art (and is not to be limited to a special or customized meaning), and furthermore refers without limitation to the sum of the observations divided by the number of observations.

The term "non-recursive filter" as used herein is a broad term and is to be given its ordinary and customary meaning to a person of ordinary skill in the art (and is not to be limited to a special or customized meaning), and furthermore refers without limitation to an equation that uses moving averages as inputs and outputs.

The terms "recursive filter" and "auto-regressive algorithm" as used herein are broad terms and are to be given their ordinary and customary meaning to a person of ordinary skill in the art (and are not to be limited to a special or customized meaning), and furthermore refer without limitation to an equation in which previous averages are part of the next filtered output. More particularly, the generation of a series of observations whereby the value of each observation is partly dependent on the values of those that have immediately preceded it. One example is a regression structure in which lagged response values assume the role of the independent variables.

The term "variation" as used herein is a broad term and is to be given its ordinary and customary meaning to a person of ordinary skill in the art (and is not to be limited to a special or customized meaning), and furthermore refers without limitation to a divergence or amount of change from a point, line, or set of data. In one embodiment, estimated analyte values can have a variation including a range of values outside of the estimated analyte values that represent a range of possibilities based on known physiological patterns, for example.

The terms "physiological parameters" and "physiological boundaries" as used herein are broad terms and are to be given their ordinary and customary meaning to a person of ordinary skill in the art (and are not to be limited to a special or customized meaning), and furthermore refer without limitation to the parameters obtained from continuous studies of physiological data in humans and/or animals. For example, a maximal sustained rate of change of glucose in humans of about 6 to 8 mg/dL/min and a maximum acceleration of the rate of change of about 0.1 to 0.2 mg/dL/min$^2$ are deemed physiologically feasible limits; values outside of these limits would be considered non-physiological. As another example, the rate of change of glucose is lowest at the maxima and minima of the daily glucose range, which are the areas of greatest risk in patient treatment, thus a physiologically feasible rate of change can be set at the maxima and minima based on continuous studies of glucose data. As a further example, it has been observed that the best solution for the shape of the curve at any point along glucose signal data stream over a certain time period (for example, about 20 to 30 minutes) is a straight line, which can be used to set physiological limits. These terms are broad enough to include physiological parameters for any analyte.

The term "measured analyte values" as used herein is a broad term and is to be given its ordinary and customary meaning to a person of ordinary skill in the art (and is not to be limited to a special or customized meaning), and furthermore refers without limitation to an analyte value or set of analyte values for a time period for which analyte data has been measured by an analyte sensor. The term is broad enough to include data from the analyte sensor before or after data processing in the sensor and/or receiver (for example, data smoothing, calibration, and the like).

The term "estimated analyte values" as used herein is a broad term and is to be given its ordinary and customary meaning to a person of ordinary skill in the art (and is not to be limited to a special or customized meaning), and furthermore refers without limitation to an analyte value or set of analyte values, which have been algorithmically extrapolated from measured analyte values.

The terms "sensor data," as used herein is a broad term and is to be given its ordinary and customary meaning to a person of ordinary skill in the art (and are not to be limited to a special or customized meaning), and furthermore refers without limitation to any data associated with a sensor, such as a continuous analyte sensor. Sensor data includes a raw data stream, or simply data stream, of analog or digital signals directly related to a measured analyte from an analyte sensor (or other signal received from another sensor), as well as calibrated and/or filtered raw data. In one example, the sensor data comprises digital data in "counts" converted by an A/D converter from an analog signal (e.g., voltage or amps) and includes one or more data points representative of a glucose concentration. Thus, the terms "sensor data point" and "data point" refer generally to a digital representation of sensor data at a particular time. The terms broadly encompass a plurality of time spaced data points from a sensor, such as from a substantially continuous glucose sensor, which comprises individual measurements taken at time intervals ranging from fractions of a second up to, e.g., 1, 2, or 5 minutes or longer. In another example, the sensor data includes an integrated digital value representative of one or more data points averaged over a time period. Sensor data may include calibrated data, smoothed data, filtered data, transformed data, and/or any other data associated with a sensor.

The term "matched data pair" or "data pair" as used herein is a broad term and is to be given its ordinary and customary meaning to a person of ordinary skill in the art (and is not to be limited to a special or customized meaning), and furthermore refers without limitation to reference data (for example, one or more reference analyte data points) matched with substantially time corresponding sensor data (for example, one or more sensor data points).

The term "sensor electronics," as used herein, is a broad term, and is to be given its ordinary and customary meaning to a person of ordinary skill in the art (and is not to be limited to a special or customized meaning), and refers without limitation to the components (for example, hardware and/or software) of a device configured to process data.

The term "calibration set" as used herein is a broad term, and is to be given its ordinary and customary meaning to a person of ordinary skill in the art (and is not to be limited to a special or customized meaning), and refers without limitation to a set of data comprising information useful for calibration. In some embodiments, the calibration set is formed from one or more matched data pairs, which are used to determine the relationship between the reference data and the sensor data; however other data derived pre-implant, externally or internally may also be used. As another example, data may also be employed from prior sensor sessions of the subject user.

The terms "sensitivity" or "sensor sensitivity," as used herein, are broad terms, and are to be given their ordinary and customary meaning to a person of ordinary skill in the art (and is not to be limited to a special or customized meaning), and refer without limitation to an amount of signal produced by a certain concentration of a measured analyte, or a measured species (e.g., $H_2O_2$) associated with the measured analyte (e.g., glucose). For example, in one embodiment, a sensor has a sensitivity of from about 1 to about 300 picoAmps of current for every 1 mg/dL of glucose analyte.

The terms "sensitivity profile" or "sensitivity curve," as used herein, are broad terms, and are to be given their ordinary and customary meaning to a person of ordinary skill in the art (and is not to be limited to a special or customized meaning), and refer without limitation to a representation of a change in sensitivity over time.

Other definitions will be provided within the description below, and in some cases from the context of the term's usage.

As employed herein, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade).

Overview/General Description of System

Conventional in vivo continuous analyte sensing technology has typically relied on reference measurements performed during a sensor session for calibration of the continuous analyte sensor. The reference measurements are matched with substantially time corresponding sensor data to create matched data pairs. Regression is then performed on the matched data pairs (e.g., by using least squares regression) to generate a conversion function that defines a relationship between a sensor signal and an estimated glucose concentration.

In critical care settings, calibration of continuous analyte sensors is often performed by using, as reference, a calibration solution with a known concentration of the analyte. This calibration procedure can be cumbersome, as a calibration bag, separate from (and an addition to) an IV (intravenous) bag, is typically used. In the ambulatory setting, calibration of continuous analyte sensors has traditionally been performed by capillary blood glucose measurements (e.g., a finger stick glucose test), through which reference data is obtained and entered into the continuous analyte sensor system. This calibration procedure typically involves frequent finger stick measurements, which can be inconvenient and painful.

Heretofore, systems and methods for in vitro calibration of a continuous analyte sensor by the manufacturer (e.g., factory calibration), without reliance on periodic recalibration, have for the most part been inadequate with respect to high levels of sensor accuracy required for glycemic management. Part of this can be attributed to changes in sensor properties (e.g., sensor sensitivity) that can occur during sensor use. Thus, calibration of continuous analyte sensors has typically involved periodic inputs of reference data, whether they are associated with a calibration solution or with a finger stick measurement. This can be very burdensome to the user during everyday life as well as to patients in the ambulatory setting or the hospital staff in the critical care setting.

The following description and examples described the present embodiments with reference to the drawings. In the drawings, reference numbers label elements of the present embodiments. These reference numbers are reproduced below in connection with the discussion of the corresponding drawing features.

Described herein are systems and methods for calibrating continuous analyte sensors that are capable of achieving high levels of accuracy, without (or with reduced) reliance on reference data from a reference analyte monitor (e.g., from a blood glucose meter).

Sensor System

FIG. 1 depicts an example system 100, in accordance with some example implementations. The system 100 includes a continuous analyte sensor system 8 including sensor electronics 12 and a continuous analyte sensor 10. The system 100 may include other devices and/or sensors, such as medicament delivery pump 2 and glucose meter 4. The continuous analyte sensor 10 may be physically connected to sensor electronics 12 and may be integral with (e.g., non-releasably attached to) or releasably attachable to the continuous analyte sensor 10. The sensor electronics 12, medicament delivery pump 2, and/or glucose meter 4 may couple with one or more devices, such as display devices 14, 16, 18, and/or 20.

In some example implementations, the system 100 may include a cloud-based analyte processor 490 configured to analyze analyte data (and/or other patient-related data) provided via network 406 (e.g., via wired, wireless, or a combination thereof) from sensor system 8 and other devices, such as display devices 14-20 and the like, associated with the host (also referred to as a patient) and generate reports providing high-level information, such as statistics, regarding the measured analyte over a certain time frame. A full discussion of using a cloud-based analyte processing system may be found in U.S. patent application Ser. No. 13/788,375, entitled "Cloud-Based Processing of Analyte Data" and filed on Mar. 7, 2013, herein incorporated by reference in its entirety.

In some example implementations, the sensor electronics 12 may include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well. The sensor electronics 12 may include hardware, firmware, software, or a combination thereof, to provide measurement of levels of the analyte via a continuous analyte sensor, such as a continuous glucose sensor. An example implementation of the sensor electronics 12 is described further below with respect to FIG. 2.

The sensor electronics 12 may, as noted, couple (e.g., wirelessly and the like) with one or more devices, such as display devices 14, 16, 18, and/or 20. The display devices 14, 16, 18, and/or 20 may be configured for presenting information (and/or alarming), such as sensor information transmitted by the sensor electronics 12 for display at the display devices 14, 16, 18, and/or 20.

The display devices may include a relatively small, key fob-like display device 14, a relatively large, hand-held display device 16, a cellular phone 18 (e.g., a smart phone, a tablet, and the like), a computer 20, and/or any other user equipment configured to at least present information (e.g., medicament delivery information, discrete self-monitoring glucose readings, heart rate monitor, caloric intake monitor, and the like).

In some example implementations, the relatively small, key fob-like display device 14 may comprise a wrist watch, a belt, a necklace, a pendent, a piece of jewelry, an adhesive patch, a pager, a key fob, a plastic card (e.g., credit card), an identification (ID) card, and/or the like. This small display device 14 may include a relatively small display (e.g., smaller than the large display device 16) and may be configured to display certain types of displayable sensor information, such as a numerical value, and an arrow, or a color code.

In some example implementations, the relatively large, hand-held display device 16 may comprise a hand-held receiver device, a palm-top computer, and/or the like. This large display device may include a relatively larger display (e.g., larger than the small display device 14) and may be configured to display information, such as a graphical representation of the continuous sensor data including current and historic sensor data output by sensor system 8.

In some example implementations, the continuous analyte sensor 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some example implementations, the continuous analyte sensor 10 may analyze a plurality of intermittent blood samples, although other analytes may be used as well.

In some example implementations, the continuous analyte sensor 10 may comprise a glucose sensor configured to measure glucose in the blood or interstitial fluid using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 10 includes a glucose sensor, the glucose sensor comprise any device capable of measuring the concentration of glucose and may use a variety of techniques to measure glucose including invasive, minimally invasive, and non-invasive sensing techniques (e.g., fluorescence monitoring), to provide data, such as a data stream, indicative of the concentration of glucose in a host. The data stream may be sensor data (raw and/or filtered), which may be converted into a calibrated data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

Although the disclosure herein refers to some implementations that include a continuous analyte sensor 10 comprising a glucose sensor, the continuous analyte sensor 10 may comprise other types of analyte sensors as well. Moreover, although some implementations refer to the glucose sensor as an implantable glucose sensor, other types of devices capable of detecting a concentration of glucose and providing an output signal representative of glucose concentration may be used as well. Furthermore, although the description herein refers to glucose as the analyte being measured, processed, and the like, other analytes may be used as well including, for example, ketone bodies (e.g., acetone, acetoacetic acid and beta hydroxybutyric acid, lactate, etc.), glucagon, acetyl-CoA, triglycerides, fatty acids, intermediaries in the citric acid cycle, choline, insulin, cortisol, testosterone, and the like.

Figure 2:
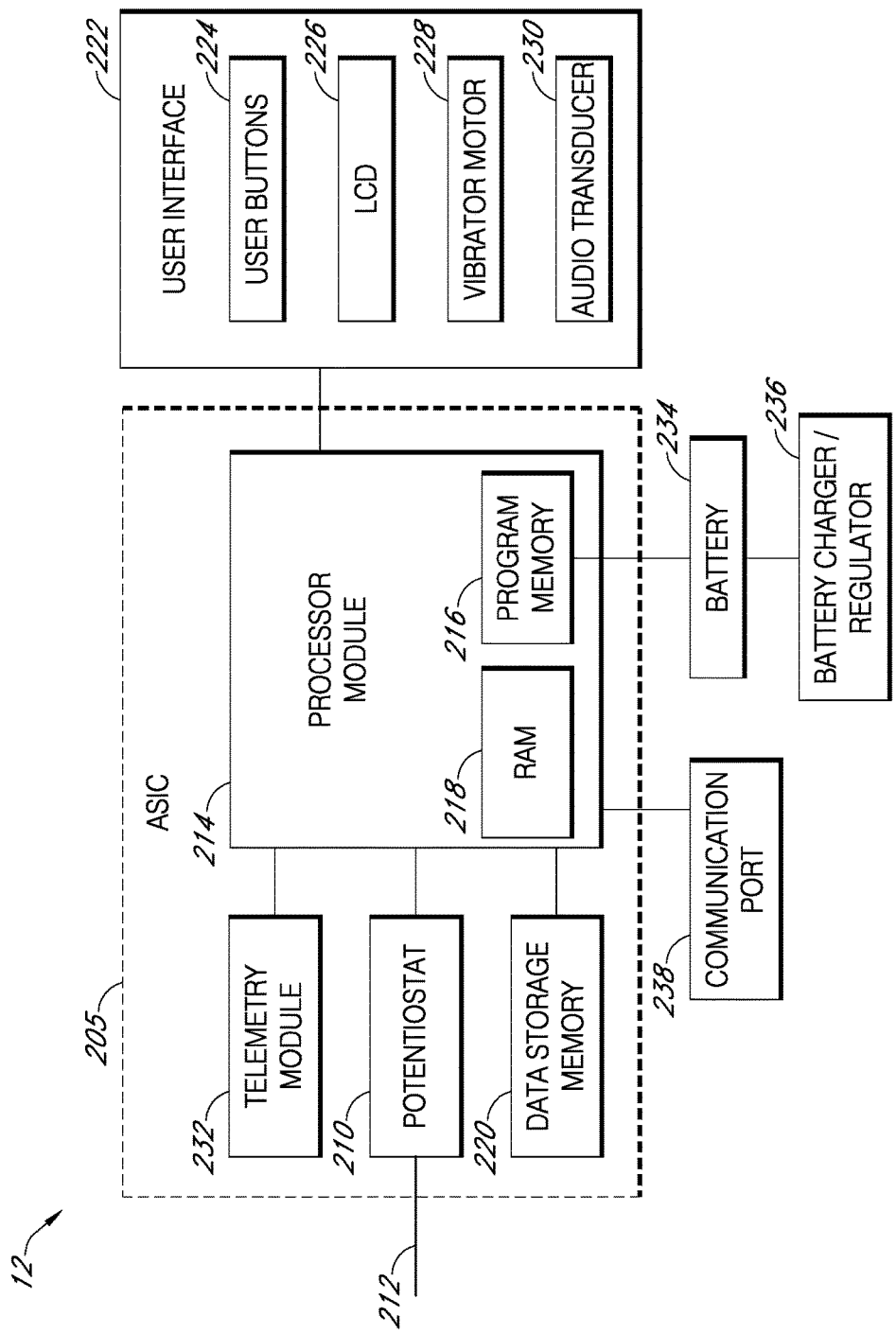
FIG. 2 is a block diagram that illustrates electronics associated with the sensor system of FIG. 1.

FIG. 2 depicts an example of sensor electronics 12, in accordance with some example implementations. The sensor electronics 12 may include sensor electronics that are configured to process sensor information, such as sensor data, and generate transformed sensor data and displayable sensor information, e.g., via a processor module. For example, the processor module may transform sensor data into one or more of the following: filtered sensor data (e.g., one or more filtered analyte concentration values), raw sensor data, calibrated sensor data (e.g., one or more calibrated analyte concentration values), rate of change information, trend information, rate of acceleration/deceleration information, sensor diagnostic information, location information, alarm/alert information, calibration information, smoothing and/or filtering algorithms of sensor data, and/or the like.

In some embodiments, a processor module 214 is configured to achieve a substantial portion, if not all, of the data processing. Processor module 214 may be integral to sensor electronics 12 and/or may be located remotely, such as in one or more of devices 14, 16, 18, and/or 20 and/or cloud 490. In some embodiments, processor module 214 may comprise a plurality of smaller subcomponents or submodules. For example, processor module 214 may include an alert module (not shown) or prediction module (not shown), or any other suitable module that may be utilized to efficiently process data. When processor module 214 is made up of a plurality of submodules, the submodules may be located within processor module 214, including within the sensor electronics 12 or other associated devices (e.g., 14, 16, 18, 20 and/or 490). For example, in some embodiments, processor module 214 may be located at least partially within a cloud-based analyte processor 490 or elsewhere in network 406.

In some example implementations, the processor module 214 may be configured to calibrate the sensor data, and the data storage memory 220 may store the calibrated sensor data points as transformed sensor data. Moreover, the processor module 214 may be configured, in some example implementations, to wirelessly receive calibration information from a display device, such as devices 14, 16, 18, and/or 20, to enable calibration of the sensor data from sensor 12. Furthermore, the processor module 214 may be configured to perform additional algorithmic processing on the sensor data (e.g., calibrated and/or filtered data and/or other sensor information), and the data storage memory 220 may be configured to store the transformed sensor data and/or sensor diagnostic information associated with the algorithms.

In some example implementations, the sensor electronics 12 may comprise an application-specific integrated circuit (ASIC) 205 coupled to a user interface 222. The ASIC 205 may further include a potentiostat 210, a telemetry module 232 for transmitting data from the sensor electronics 12 to one or more devices, such as devices 14, 16, 18, and/or 20, and/or other components for signal processing and data storage (e.g., processor module 214 and data storage memory 220). Although FIG. 2 depicts ASIC 205, other types of circuitry may be used as well, including field programmable gate arrays (FPGA), one or more microprocessors configured to provide some (if not all of) the processing performed by the sensor electronics 12, analog circuitry, digital circuitry, or a combination thereof.

In the example depicted in FIG. 2, the potentiostat 210 is coupled to a continuous analyte sensor 10, such as a glucose sensor to generate sensor data from the analyte. The potentiostat 210 may also provide via data line 212 a voltage to the continuous analyte sensor 10 to bias the sensor for measurement of a value (e.g., a current and the like) indicative of the analyte concentration in a host (also referred to as the analog portion of the sensor). The potentiostat 210 may have one or more channels depending on the number of working electrodes at the continuous analyte sensor 10.

In some example implementations, the potentiostat 210 may include a resistor that translates a current value from the sensor 10 into a voltage value, while in some example implementations, a current-to-frequency converter (not shown) may also be configured to integrate continuously a measured current value from the sensor 10 using, for example, a charge-counting device. In some example implementations, an analog-to-digital converter (not shown) may digitize the analog signal from the sensor 10 into so-called "counts" to allow processing by the processor module 214. The resulting counts may be directly related to the current measured by the potentiostat 210, which may be directly related to an analyte level, such as a glucose level, in the host.

The telemetry module 232 may be operably connected to processor module 214 and may provide the hardware, firmware, and/or software that enable wireless communication between the sensor electronics 12 and one or more other devices, such as display devices, processors, network access devices, and the like. A variety of wireless radio technologies that can be implemented in the telemetry module 232 include Bluetooth, Bluetooth Low-Energy, ANT, ANT+, ZigBee, IEEE 802.11, IEEE 802.16, cellular radio access technologies, radio frequency (RF), infrared (IR), paging network communication, magnetic induction, satellite data communication, spread spectrum communication, frequency hopping communication, near field communications, and/or the like. In some example implementations, the telemetry module 232 comprises a Bluetooth chip, although Bluetooth technology may also be implemented in a combination of the telemetry module 232 and the processor module 214.

The processor module 214 may control the processing performed by the sensor electronics 12. For example, the processor module 214 may be configured to process data (e.g., counts), from the sensor, filter the data, calibrate the data, perform fail-safe checking, and/or the like.

In some example implementations, the processor module 214 may comprise a digital filter, such as for example an infinite impulse response (IIR) or a finite impulse response (FIR) filter. This digital filter may smooth a raw data stream received from sensor 10. Generally, digital filters are programmed to filter data sampled at a predetermined time interval (also referred to as a sample rate). In some example implementations, such as when the potentiostat 210 is configured to measure the analyte (e.g., glucose and/or the like) at discrete time intervals, these time intervals determine the sampling rate of the digital filter. In some example implementations, the potentiostat 210 may be configured to measure continuously the analyte, for example, using a current-to-frequency converter. In these current-to-frequency converter implementations, the processor module 214 may be programmed to request, at predetermined time intervals (acquisition time), digital values from the integrator of the current-to-frequency converter. These digital values obtained by the processor module 214 from the integrator may be averaged over the acquisition time due to the continuity of the current measurement. As such, the acquisition time may be determined by the sampling rate of the digital filter. Other uses of FIR filters are described in greater detail below.

The processor module 214 may further include a data generator (not shown) configured to generate data packages for transmission to devices, such as the display devices 14, 16, 18, and/or 20. Furthermore, the processor module 214 may generate data packets for transmission to these outside sources via telemetry module 232. In some example implementations, the data packages may, as noted, be customizable for each display device, and/or may include any available data, such as a time stamp, displayable sensor information, transformed sensor data, an identifier code for the sensor and/or sensor electronics 12, raw data, filtered data, calibrated data, rate of change information, trend information, error detection or correction, and/or the like.

The processor module 214 may also include a program memory 216 and other memory 218. The processor module 214 may be coupled to a communications interface, such as a communication port 238, and a source of power, such as a battery 234. Moreover, the battery 234 may be further coupled to a battery charger and/or regulator 236 to provide power to sensor electronics 12 and/or charge the battery 234.

The program memory 216 may be implemented as a semi-static memory for storing data, such as an identifier for a coupled sensor 10 (e.g., a sensor identifier (ID)) and for storing code (also referred to as program code) to configure the ASIC 205 to perform one or more of the operations/functions described herein. For example, the program code may configure processor module 214 to process data streams or counts, filter, perform the calibration methods described below, perform fail-safe checking, and the like.

The memory 218 may also be used to store information. For example, the processor module 214 including memory 218 may be used as the system's cache memory, where temporary storage is provided for recent sensor data received from the sensor. In some example implementations, the memory may comprise memory storage components, such as read-only memory (ROM), random-access memory (RAM), dynamic-RAM, static-RAM, non-static RAM, easily erasable programmable read only memory (EEPROM), rewritable ROMs, flash memory, and the like.

The data storage memory 220 may be coupled to the processor module 214 and may be configured to store a variety of sensor information. In some example implementations, the data storage memory 220 stores one or more days of continuous analyte sensor data. For example, the data storage memory may store 1, 2, 3, 4, 5, 6, 7, 8, 9, 10, 11, 12, 13, 14, 15, 20, and/or 30 (or more days) of continuous analyte sensor data received from sensor 10. The stored sensor information may include one or more of the following: a time stamp, raw sensor data (one or more raw analyte concentration values), calibrated data, filtered data, transformed sensor data, and/or any other displayable sensor information, calibration information (e.g., reference BG values and/or prior calibration information), sensor diagnostic information, and the like.

The user interface 222 may include a variety of interfaces, such as one or more buttons 224, a liquid crystal display (LCD) 226, a vibrator 228, an audio transducer (e.g., speaker) 230, a backlight (not shown), and/or the like. The components that comprise the user interface 222 may provide controls to interact with the user (e.g., the host). One or more buttons 224 may allow, for example, toggle, menu selection, option selection, status selection, yes/no response to on-screen questions, a "turn off" function (e.g., for an alarm), an "acknowledged" function (e.g., for an alarm), a reset, and/or the like. The LCD 226 may provide the user with, for example, visual data output. The audio transducer 230 (e.g., speaker) may provide audible signals in response to triggering of certain alerts, such as present and/or predicted hyperglycemic and hypoglycemic conditions. In some example implementations, audible signals may be differentiated by tone, volume, duty cycle, pattern, duration, and/or the like. In some example implementations, the audible signal may be configured to be silenced (e.g., acknowledged or turned off) by pressing one or more buttons 224 on the sensor electronics 12 and/or by signaling the sensor electronics 12 using a button or selection on a display device (e.g., key fob, cell phone, and/or the like).

Although audio and vibratory alarms are described with respect to FIG. 2, other alarming mechanisms may be used as well. For example, in some example implementations, a tactile alarm is provided including a poking mechanism configured to "poke" or physically contact the patient in response to one or more alarm conditions.

The battery 234 may be operatively connected to the processor module 214 (and possibly other components of the sensor electronics 12) and provide the necessary power for the sensor electronics 12. In some example implementations, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some example implementations, the battery is rechargeable. In some example implementations, a plurality of batteries can be used to power the system. In yet other implementations, the receiver can be transcutaneously powered via an inductive coupling, for example.

A battery charger and/or regulator 236 may be configured to receive energy from an internal and/or external charger. In some example implementations, a battery regulator (or balancer) 236 regulates the recharging process by bleeding off excess charge current to allow all cells or batteries in the sensor electronics 12 to be fully charged without overcharging other cells or batteries. In some example implementations, the battery 234 (or batteries) is configured to be charged via an inductive and/or wireless charging pad, although any other charging and/or power mechanism may be used as well.

One or more communication ports 238, also referred to as external connector(s), may be provided to allow communication with other devices, for example a PC communication (com) port can be provided to enable communication with systems that are separate from, or integral with, the sensor electronics 12. The communication port, for example, may comprise a serial (e.g., universal serial bus or "USB") communication port, and allow for communicating with another computer system (e.g., PC, personal digital assistant or "PDA," server, or the like). In some example implementations, the sensor electronics 12 is able to transmit historical data to a PC or other computing device (e.g., an analyte processor as disclosed herein) for retrospective analysis by a patient and/or physician. As another example of data transmission, factory information may also be sent to the algorithm from the sensor or from a cloud data source.

In some continuous analyte sensor systems, an on-skin portion of the sensor electronics may be simplified to minimize complexity and/or size of on-skin electronics, for example, providing only raw, calibrated, and/or filtered data to a display device configured to run calibration and other algorithms required for displaying the sensor data. However, the sensor electronics 12 (e.g., via processor module 214) may be implemented to execute prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor data, set modes of operation, evaluate the data for aberrancies, and/or the like.

Although separate data storage and program memories are shown in FIG. 2, a variety of configurations may be used as well. For example, one or more memories may be used to provide storage space to support data processing and storage requirements at sensor electronics 12.

Calibration

While some continuous glucose sensors rely on (and assume an accuracy of) BG values and/or factory derived information for calibration, the disclosed embodiments exploit real-time information (e.g., including in some implementations just sensor data itself) to determine aspects of calibration as well as to calibrate based thereon.

In some cases calibration of an analyte sensor may use a priori calibration distribution information. For example, in some embodiments, a priori calibration distribution information or a code can be received as information from a previous calibration and/or sensor session (e.g., same sensor system, internally stored), stored in memory, coded at the factory (e.g., as part of factory settings), on a barcode of packaging, sent from the cloud or a network of remote servers, coded by a care provider or the user, received from another sensor system or electronic device, based on results from laboratory testing, and/or the like.

As used herein, a priori information includes information obtained prior to a particular calibration. For example, from previous calibrations of a particular sensor session (e.g., feedback from a previous calibration(s)), information obtained prior to sensor insertion (e.g., factory information from in vitro testing or data obtained from previously implanted analyte concentration sensors, such as sensors of the same manufacturing lot of the sensor and/or sensors from one or more different lots), prior in vivo testing of a similar sensor on the same host, and/or prior in vivo testing of similar sensors on different hosts. Calibration information includes information useful in calibrating a continuous glucose sensor, such as, but not limited to: sensitivity (m), change in sensitivity (Δdm/dt), which may also be referred to drift in sensitivity, rate of change of sensitivity (ddm/ddt), baseline/intercept (b), change in baseline (Δdb/dt), rate of change of baseline (ddb/ddt), baseline and/or sensitivity profiles (i.e., change over a time period) associated with the sensor; linearity, response time, relationships between properties of the sensor (e.g., relationships between sensitivity and baseline), or relationships between particular stimulus signal output (e.g., output indicative of an impedance, capacitance or other electrical or chemical property of the sensor) and sensor sensitivity or temperature (e.g., determined from prior in vivo and/or ex vivo studies) such as described in U.S. Patent Publication 2012-0265035-A1, which is incorporated herein by reference in its entirety; sensor data obtained from previously implanted analyte concentration sensors; calibration code(s) associated with a sensor being calibrated; patient specific relationships between sensor and sensitivity, baseline, drift, impedance, impedance/temperature relationship (e.g., determined from prior studies of the patient or other patients having common characteristics with the patient), site of sensor implantation (abdomen, arm, etc.) and/or specific relationships (different sites may have different vascular density). Distribution information includes ranges, distribution functions, distribution parameters (mean, standard deviation, skewness, etc.), generalized functions, statistical distributions, profiles, or the like that represent a plurality of possible values for calibration information. Taken together, a priori calibration distribution information includes range(s) or distribution(s) of values (e.g., describing their associated probabilities, probability density functions, likelihoods, or frequency of occurrence) provided prior to a particular calibration process useful for calibration of the sensor (e.g., sensor data).

For example, in some embodiments, a priori calibration distribution information includes probability distributions for sensitivity (m) or sensitivity-related information and baseline (b) or baseline-related information based on e.g., sensor type. As described above, the prior distribution of sensitivity and/or baseline may be factory-derived (e.g., from in vitro or in vivo testing of representative sensors) or derived from previous calibrations.

Figure 3:
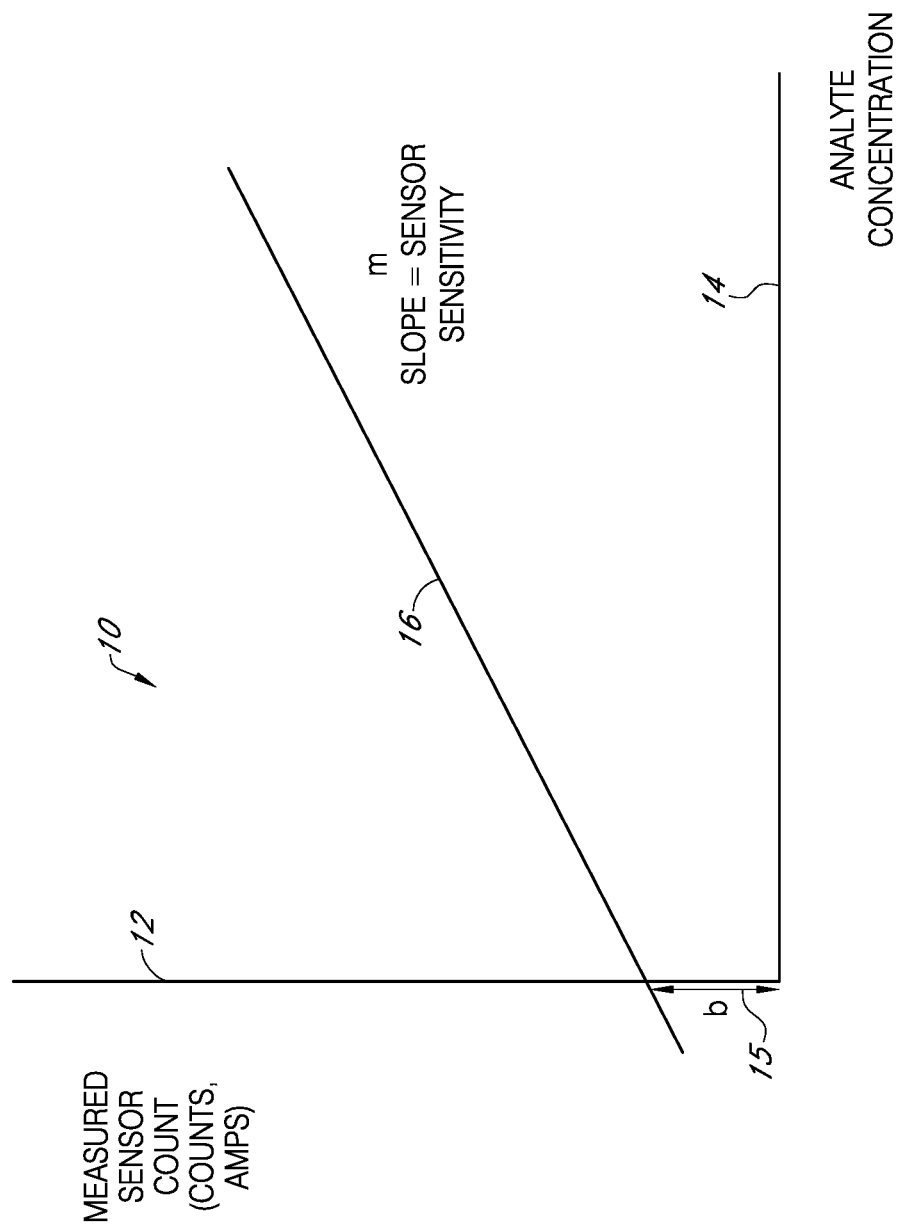
FIG. 3 depicts a graph illustrating a linear relationship between the measured sensor count and analyte concentration.

As noted above, an analyte sensor generally includes an electrode to monitor a current change in either a co-reactant or a product to determine analyte concentration, e.g., glucose concentration. In one example, the sensor data comprises digital data in "counts" converted by an A/D converter from an analog signal (e.g., voltage or amps). Calibration is the process of determining the relationship between the measured sensor signal in counts and the analyte concentration in clinical units. For example, calibration allows a given sensor measurement in counts to be associated with a measured analyte concentration value, e.g., in milligrams per deciliter. Referring to the graph 10 of FIG. 3, this relationship is generally a linear one, of the form $y=mx+b$, where 'y' is the sensor signal in counts (y-axis 12), 'x' is the clinical value of the analyte concentration (axis 14), and 'm' is the sensor sensitivity, having units of [counts/(mg/dL)]. A line 16 is illustrated whose slope is termed the sensor sensitivity. 'b' (see line segment 15) is the baseline sensor signal, which can be taken into account, or for advanced sensors, can generally be reduced to zero or nearly zero; in any event, in many cases, the baseline can be assumed to be small or capable of being compensated for in a predictable manner. In some implementations a constant background signal is seen, and such are modeled by $y=m(x+c)$, where c is a glucose offset between the sensor site and the blood glucose.

Once the line 16 has been determined, the system can convert a measured number of counts (or amps, e.g., picoamps, as described above) to a clinical value of the analyte concentration.

However, values of m and b vary from sensor to sensor and require determination. In addition, the slope value m is not always constant. For example, and referring to FIG. 4, the value m can be seen to change from an initial sensitivity value $m_0$ to a final sensitivity value $m_F$ over the course of time within a session. Its rate of change is seen to be greatest in the first few days of use, and this rate of change is termed $m_R$.

The slope is a function of in vivo time for a number of reasons. Particularly for initial changes in calibration, such are often due to the sensor membrane "settling in" and achieving equilibrium with the in vivo environment. Sensors are generally calibrated in vitro or on the bench, and efforts are made to make the in vitro environment as close as possible to the in vivo one, but differences are still apparent, and the in vivo environment itself changes from user to user. In addition, sensors may vary due to differences in sterilization or shelf-life/storage conditions. Calibration changes that occur later in the session are often due to changes in the tissue surrounding the sensor, e.g., a buildup of biofilm on the sensor.

Whatever the cause, certain effects of variability have been measured and determined. For example, it is known that variability in the final sensitivity $m_F$ is the largest contributor to overall sensor inaccuracy. Similarly, it is known that variability in the initial sensitivity $m_0$ and physiology are the largest contributors to inaccuracy of sensors on the first day.

Because of the variability noted above, an initial step of calibration includes determining and using seed values for one or more calibration parameters until additional data is obtained to adjust the seed value to a more accurate one.

Once calibration is achieved, the sensor and analyte concentration measurement system may be employed to accurately determine clinical values of an analyte concentration in a user. Such may then lead to discrimination of other sensor behaviors, including determination of errors and drifts in sensitivity, as are described in greater detail below.

Figure 4:
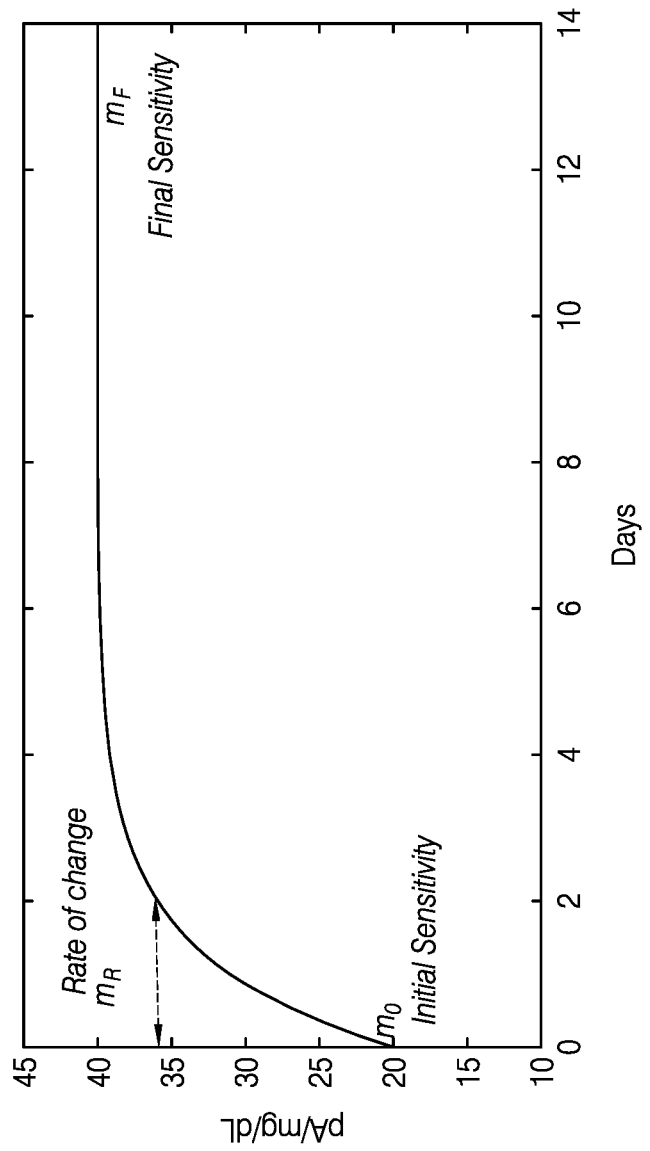
FIG. 4 illustrates an exemplary change of sensitivity over time.

The most common current method of calibration is by use of an external blood glucose meter. Such is commonly termed a "fingerstick calibration", and is a well-known and common part of life for many diabetics. This technique has the advantage of not requiring significant factory information, and further provides a low risk of outliers. A disadvantage is that significant user involvement is required, as well as requiring knowledge of certain other factory calibration information needed for appropriate calibration. As the measurements from such meters are trusted once the meters are themselves calibrated, values from the meters can be used to calibrate an indwelling analyte concentration meter. Even though the sensor sensitivity changes over time as seen in FIG. 4, the changing sensitivity is immaterial if the user is willing to perform numerous external calibrations.

However, users generally do not wish to perform numerous such calibrations, and in many cases, e.g., patients who are type II diabetic, prediabetic, or even nondiabetic, the additional accuracy provided by such calibrations is not strictly required. For example, it may be enough for a user to know what range they are in, rather than an exact analyte concentration value. In another implementation, data may be provided with an associated confidence interval, to let the user know how much confidence to place in the displayed data.

Thus efforts have been made to reduce the number of calibrations. Nevertheless, many current CGM systems still require a blood glucose value to be used for at least an initial calibration and the same is also often required when dosing. Present systems and methods according to present principles are directed in part to ways of reducing or eliminating such required calibrations.

Figure 5:
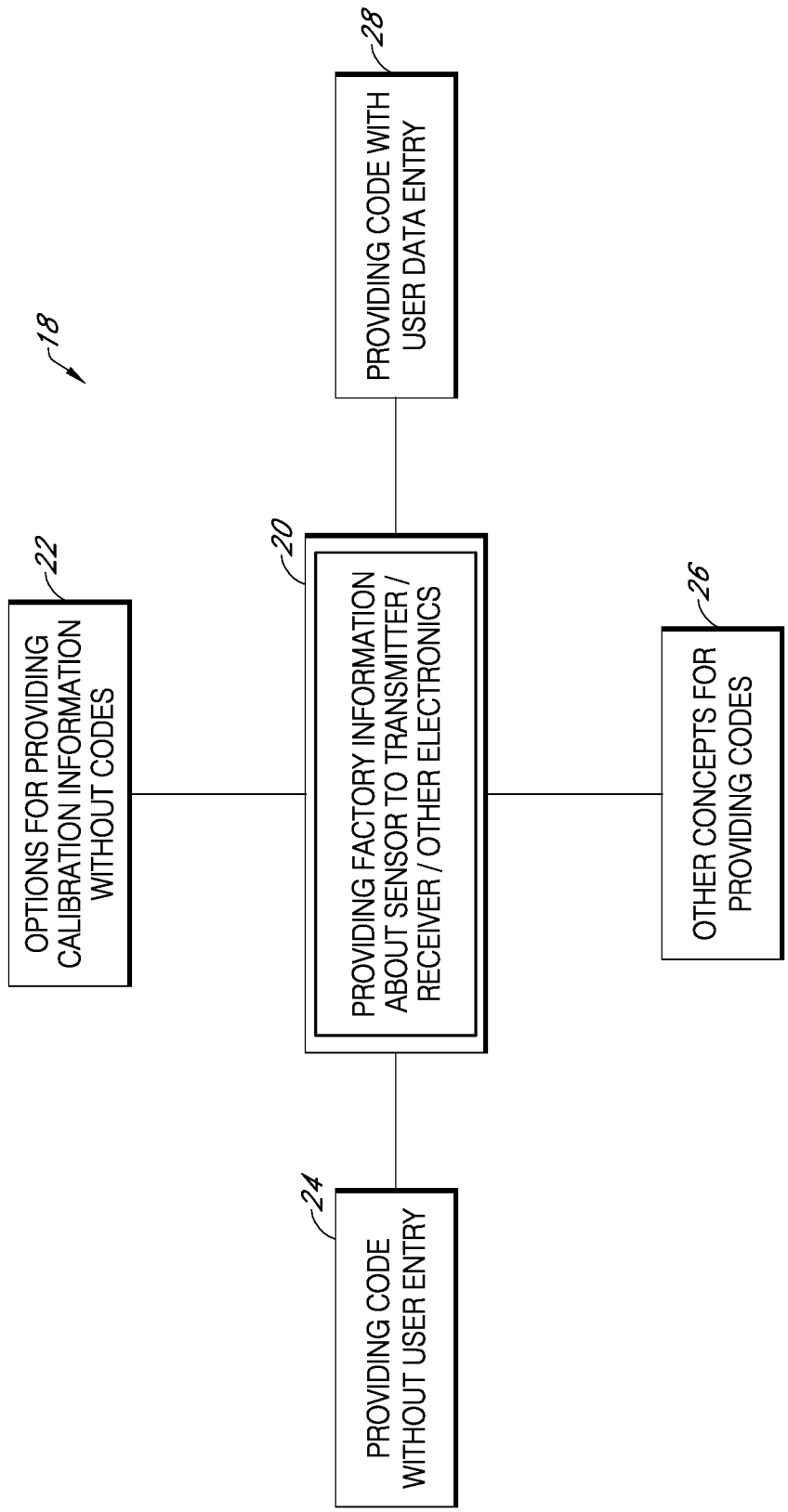
FIG. 5 illustrates various ways of providing factory information about a sensor to transmitter electronics.

One simple and convenient way of providing some level of calibration is by use of calibration information about related sensors. Even if the calibration information is approximate, such may still be sufficient for use by certain groups of patients. For example, and referring to the flowchart 18 of FIG. 5, if factory calibration is known about one or more sensors within a manufacturing lot, then this information may be provided to other sensors in the manufacturing lot that have not yet been used in patients (step 20). This step is often termed providing a "code" to a transmitter, as codes are often used to identify the manufacturing lot (and thus details) of the sensor as the same are coupled together during insertion in a patient as part of a CGM system. The transmitter may then identify the manufacturing lot from the code, and apply appropriate calibration parameters according to a lookup table or other technique. However, it should be understood that the code may be provided not just to a transmitter but to any device in which counts may be converted to clinical units, e.g., a dedicated receiver, an off-the-shelf device which may be employed to receive and display analyte concentrations, e.g., a smart phone, tablet computer, or the like. In addition, the code may not be a code in a typical sense but may simply provide any identifier to any device requiring the same for calibration purposes.

Referring again to FIG. 5, ways are described of accomplishing the step of providing factory information about the sensor to the transmitter or other electronics (step 20). Some of these ways constitute options for providing calibration information without using codes (step 22). Others include ways of providing a code using a step of user data entry (step 28). In some cases, codes may be entered without user entry (step 24). Still other ways of providing codes may be used (step 26), and such additional ways are also described below. Details of these methods are now described.

Figure 6:
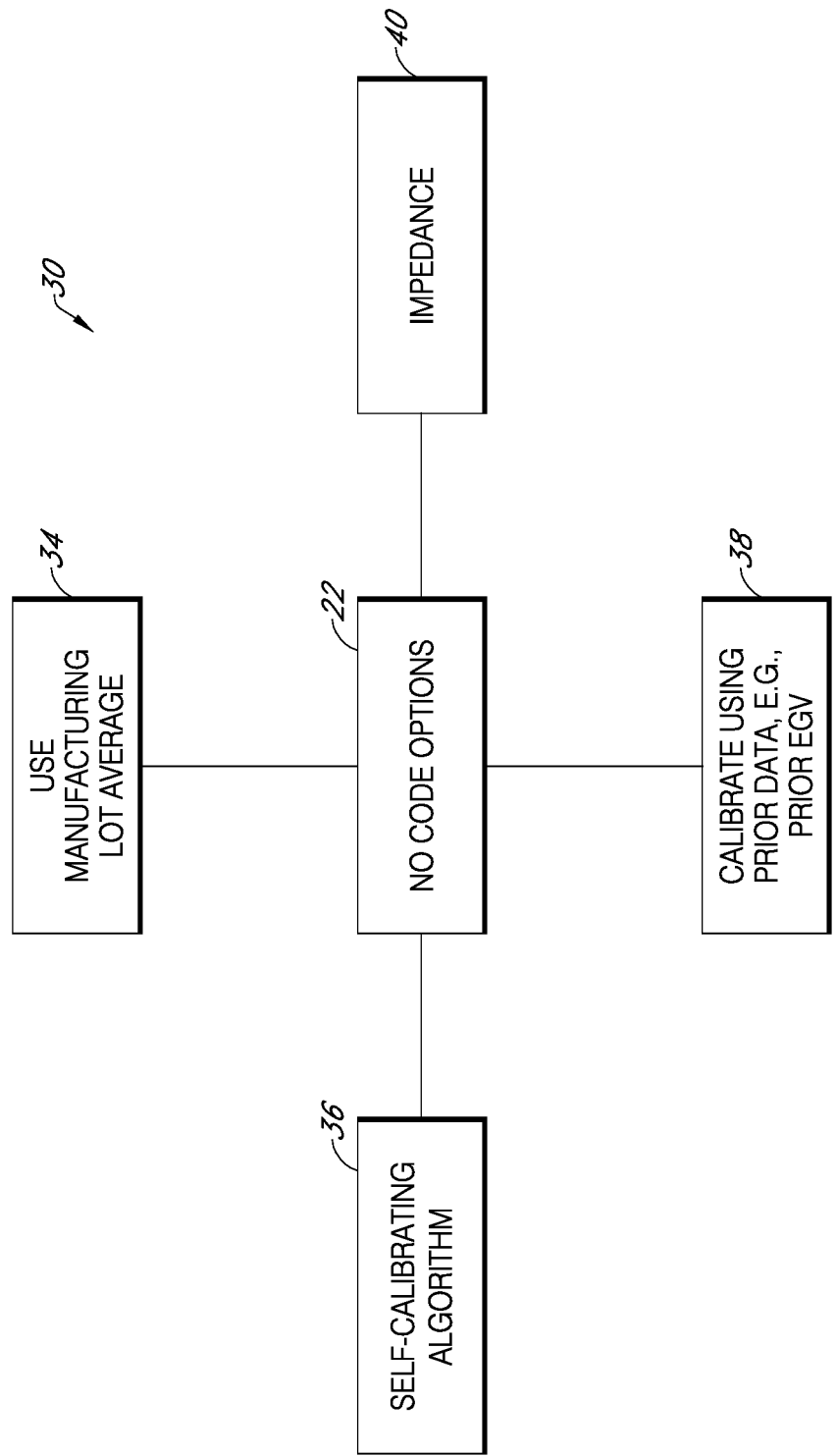
FIG. 6 illustrates "no code" options for providing factory information about a sensor to sensor electronics.

Referring to the flowchart 30 of FIG. 6, examples of providing factory calibration information in the absence of the code (step 22) are described. A first way is using a representative value, e.g., average or median or other measure, e.g., range, of the manufacturing lot (step 34). That is, if an average is known of the manufacturing lot, or even if an average is known of a different manufacturing lot, manufactured using the same techniques, then it may be assumed that the sensor calibration parameters will be similar and thus may be used as part of a calibration of a new sensor. Alternatively, a predictable relationship may also be employed to interpolate sensor calibration parameters, e.g., bracketing sensor lots.

As another example, impedance measurements may be employed in the determination of calibration parameters (step 40).

Calibrations may also occur using information about prior calibrations (step 38). For example, if a user just switched out a sensor which was calibrated and measuring the user's glucose concentration at, e.g., 120 mg/dL, then it may be assumed that a proper measurement of a newly inserted sensor should be such that the user's glucose value is again 120 mg/dL. In some cases, if a predicted glucose value has been determined, the predicted value may be used for the newly inserted sensor. Even if a short period of time has elapsed between the last reading of the old sensor and a new sensor reading, recognition of physiologically feasible glucose changes will lead to bounds in what the new measurement can be, and thus what the calibration parameters of the new sensor can be.

In yet another variation, various self-calibrating algorithms may be employed (step 36) in order to self-calibrate a CGM system. In this sense CGM systems may be termed as becoming "self-aware". For example, a CGM system may be seeded with an average glucose value if known, e.g., from a prior session, including use of a prior session steady state value or a prior session slow moving average, as will be described in greater detail below. CGM systems may also be seeded with A1C values if available. Various assumptions may also be made if appropriate. The seeded average value can be represented by a distribution, techniques for which will also be described in greater detail below.

Figure 7:
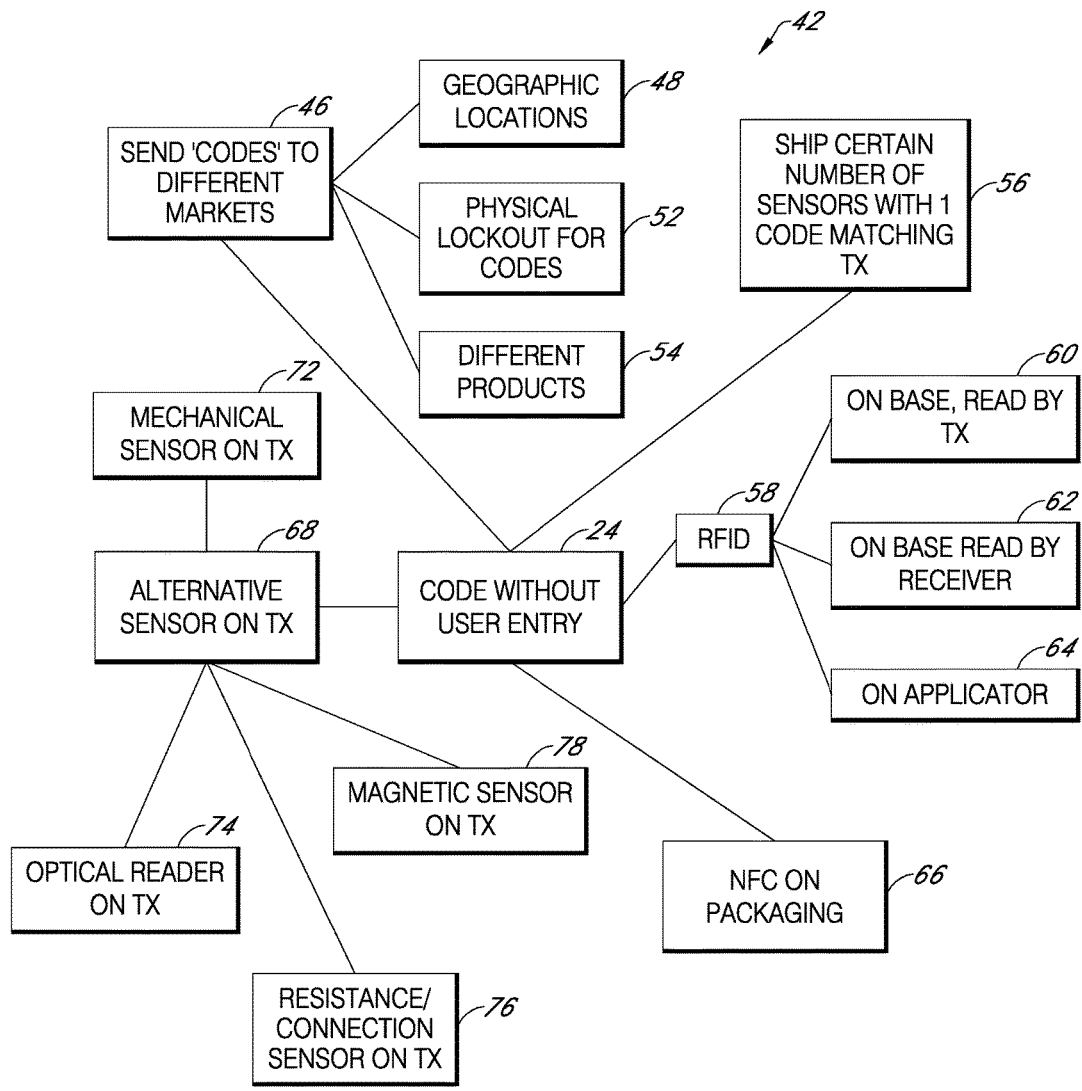
FIG. 7 illustrates options for providing factory information about a sensor to sensor electronics without explicit user entry.

FIG. 7 describes systems in which codes may be provided from a sensor to a transmitter without a step of user entry (step 24). Again it is noted that while language is used here about providing the code to a transmitter, it will be understood that codes may be provided to various devices in signal communication with the transmitter as well, including a dedicated receiver, smart phone, tablet computer, follower device, or other computing environment.

In the implementations of the diagram 42 of FIG. 7, codes or the like are provided to the transmitter but without significant user involvement. For example, a degree of encoding may be accomplished by sending a manufacturing lot of sensors to different markets (step 46). In one implementation, sensors with like codes may be sent to different geographic locations (step 48). For example, sensors sent to a particular geographic region may be from a similar or the same manufacturing lot, and when the same is inserted and makes initial contact with the network, calibration parameters known for that lot may be provided to the transmitter, thus providing an immediate degree of calibration based on geographic location. Geolocation may be employed to identify a location, and the location may then be used to identify or categorize a sensor.

In the same way, sensors of like lots may be grouped by product, so different codes then are associated with different products (step 54). For example, a first product may have a first code associated with it, and all the sensors for that product may be manufactured in the same or a similar way, leading to little manufacturing variability between sensors associated with the particular product. In this case, once the product is identified, the associated sensor calibration parameters may be uniquely determined, at least as an average.

In another implementation, without specific regard to geographic location or product, a certain group of sensors having a particular code may be shipped with a code particularly associated with the respective user's transmitter (step 56). In this case once the calibration parameters are known for one member of the group sent, and such may be known long before the group is sent, then the calibration parameters for the rest of the group are also known.

RFID technology may also be used to identify a manufacturing lot of sensors (step 58). For example, a small RFID chip may be located on the base of the sensor, and may be read by the transmitter when the sensor and transmitter are coupled (step 60). In another implementation, an RFID may be read by the receiver (step 62), or alternatively a smart phone or other device. Alternatively, the RFID device may be located on the applicator, and the transmitter may again read the identification information (and thus calibration information) when the applicator is used to install a sensor in a patient.

In yet another implementation, near field communications (NFC) may be employed on the packaging or on any other component of the system (step 66) to communicate the identification information.

Other types of communication schemes may be employed to communicate the information from a sensor to a transmitter. For example, a mechanical sensor on the transmitter may allow communication of code information (step 72), e.g., bumps, vertical pins, a mechanical system sensing orientation of the transmitter to the base, or other mechanical elements readable by the transmitter. Magnetic sensors may be employed for the same purpose (step 78), and in the same way an optical reader on the transmitter may be employed (step 74) to read, e.g., barcodes or QR codes, as well as other identifying marks or colors. Resistive sensors may also be employed (step 76), or other sensors detecting a state of connection. For example, sensors of different codes may be provided with respective different lengths. Sensors may be provided with multiple contact pads that the sensors are aligned to. Sensors of different codes may be provided with different resistances, and measurement of the same may determine the code.

Figure 8:
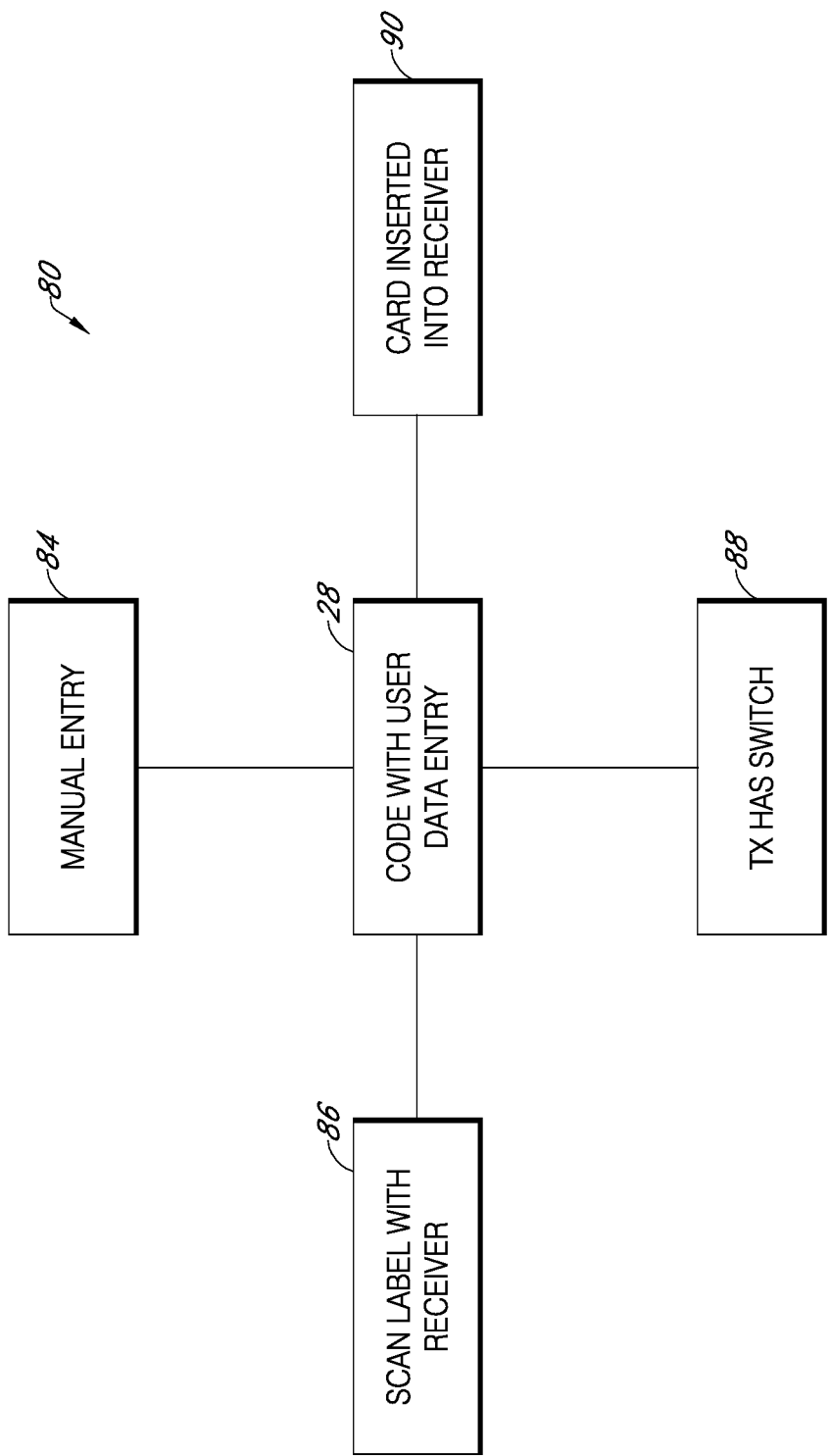
FIG. 8 illustrates options for providing factory information about a sensor to sensor electronics with user entry.

FIG. 8 illustrates a diagram 80 showing ways of code communication employing user data entry (step 28). In perhaps the simplest, the code may be provided to the user upon purchase, and the same simply manually entered (step 84) into the receiver, smart phone, or other device with a UI allowing data entry. For example, the user may input text, a number, a color, or the like. The sensor may also ship with a card, e.g., a SIM card, and the SIM card may be inserted into the receiver (step 90) to allow calibration information to be communicated but without requiring that the user enter a manual code. The transmitter may be provided with a switch system (step 88), and the user may adjust the position of switches on the transmitter according to instructions on the received sensor. For example, the transmitter switch may be a four position switch, or a DIP switch, and by appropriate adjustment, the user may provide a code associated with the sensor to the transmitter. The receiver or smart phone may also be enabled to scan a label associated with the sensor, via an integral camera or barcode reader, to allow the information to be communicated in that fashion. The scan may be of a bar label, QR code, or the like.

One variation is described below with respect to FIGS. 9-11. This implementation employs human data from the field to improve or enable a factory calibration. In more detail, factory calibration parameters (e.g., sensitivity and baseline over time) are often best identified using human data. Although bench data correlates with human data, the correlation is not yet perfect and there are often offsets in the correlations. Having access to human data generated by each lot of sensors produced during manufacturing would generally be the best data set to generate factory calibration information. Factory calibration parameters can change between lots and so characterizing each lot may be advantageous as improvements are made.

Figure 9:
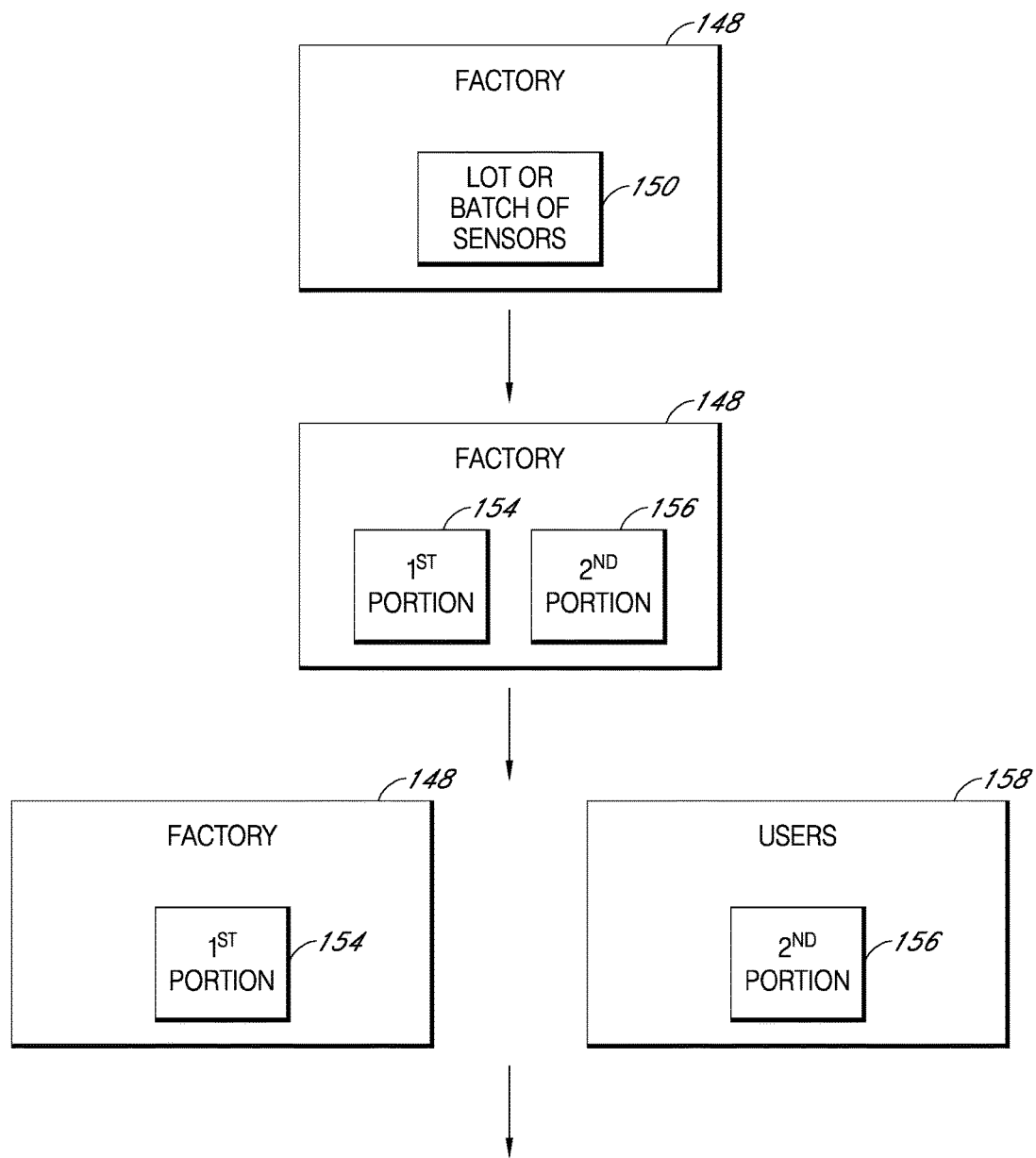
FIGS. 9 and 10 illustrate steps of using one portion of a lot of sensors, having obtained field data, to calibrate another portion of a lot of sensors.
Figure 10:
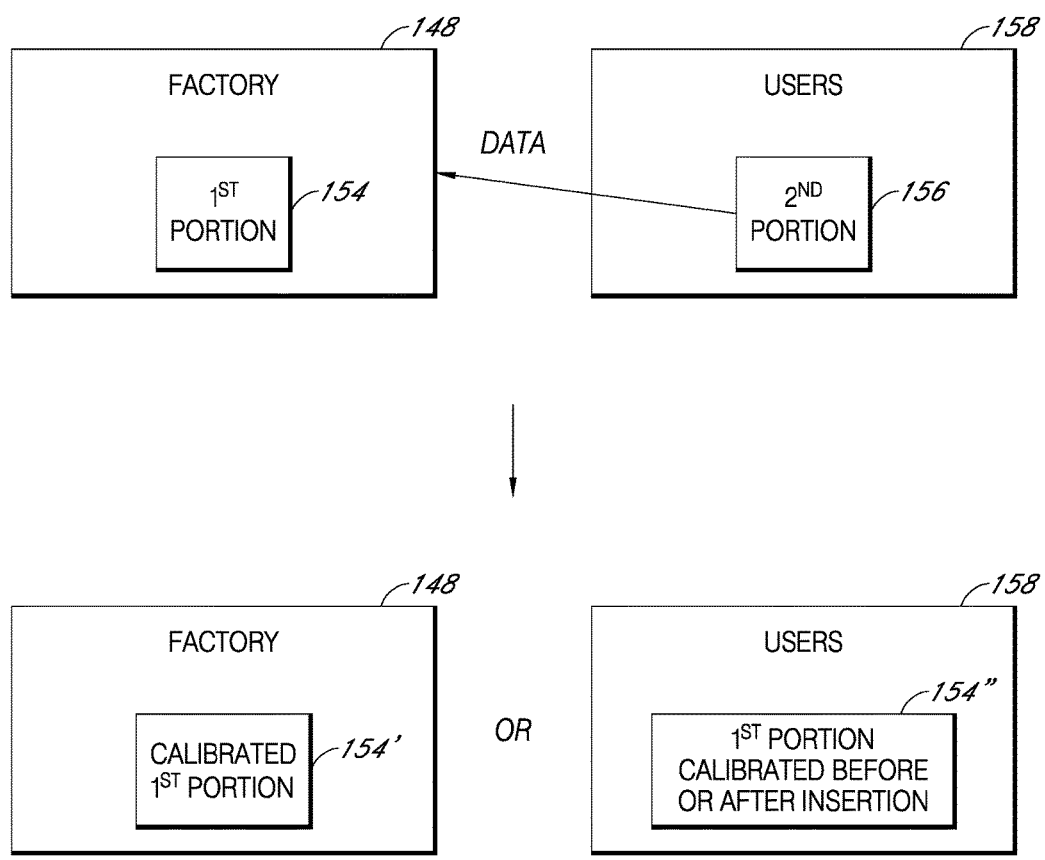
Figure 11:
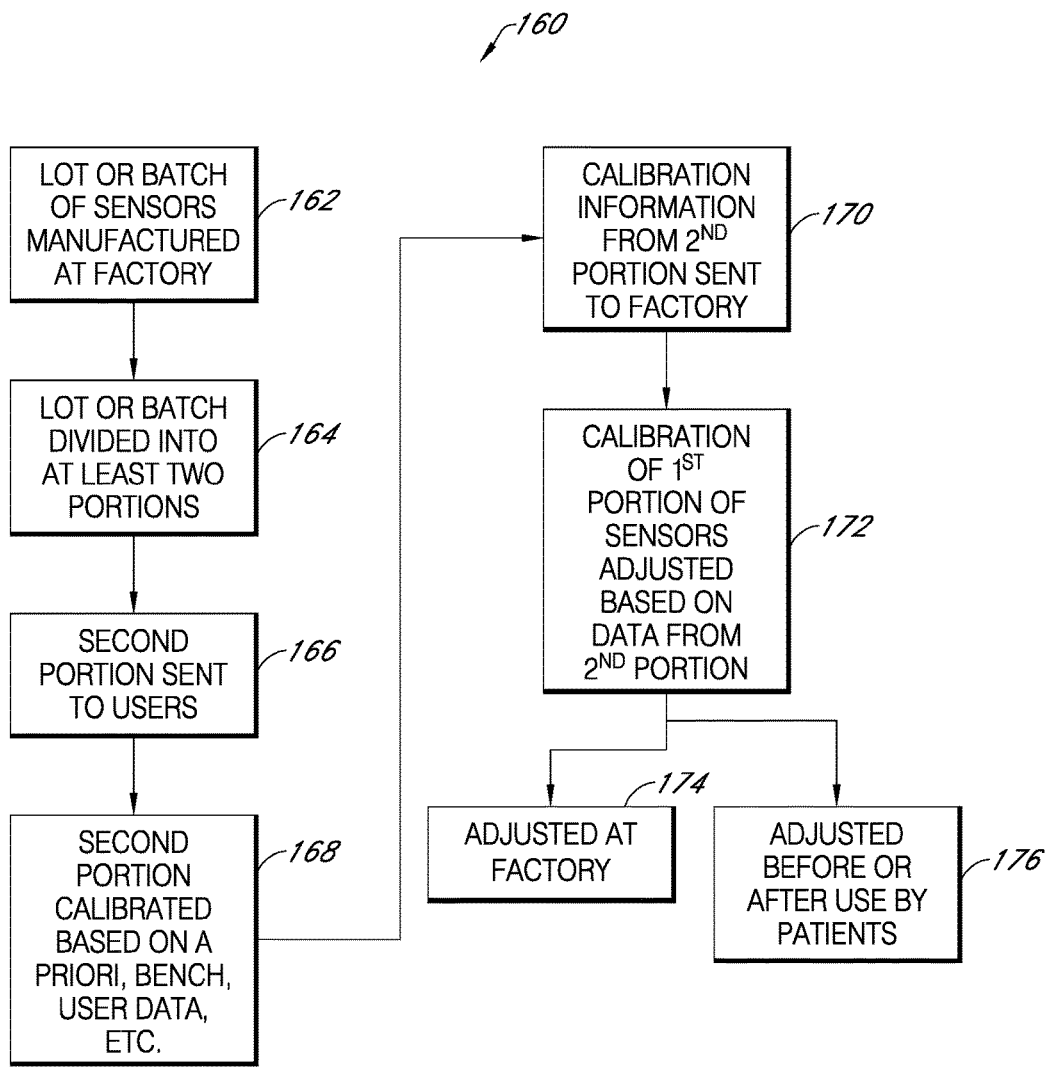
FIG. 11 is a flowchart illustrating an exemplary method according to present principles, and in particular for performing a method according to FIGS. 9 and 10.

FIGS. 9-11 shows a method that uses data collected in humans using part of a lot of sensors to generate or adjust the factory calibration numbers for the rest of the lot. There are several arrangements of this method.

In one arrangement, calibrated sensors are sent to the market for use by patients. As such sensors are calibrated in connected systems, e.g., via a blood glucose calibration techniques or other calibration techniques, including those using only the CGM signal itself, calibration information may be returned to the manufacturer through the cloud or other Internet-based network. The information may be used to generate the factory calibration settings for the remainder of the manufacturing lot of sensors that were not sent out to the market, and the same may then be shipped.

In another implementation, there is an initial factory calibration setting that is shipped with the product. Again cloud or network information may be monitored, and a determination may be made as to how closely the actual parameters match the initial factory calibration settings. Adjustments may then be made to the factory calibration setting of the unshipped sensors based on this determined closeness. In this implementation and in the prior one, release of the sensor products may be staggered so that subsequent shipments have improved accuracy. This implementation may further be performed even if all of the sensors have been shipped, as adjustments may be performed through the network or through the cloud.

In more detail, and referring to FIG. 9, a factory 148 is illustrated having a manufacturing lot or batch of sensors 150, the manufacturing lot or batch generally created in the same (or a very similar) manufacturing process. The lot or batch 150 may be divided into a first portion 154 and a second portion 156. The first portion 154 may temporarily stay with the factory 148, while the second portion 156 may be sent to a group of users 158.

Referring next to FIG. 10, data from the second portion 156 may be used at the factory 148 to inform the factory calibration of the first portion 154, transforming the same into a calibrated first portion 154'. If the first portion 154 has already been shipped, then within the user's group 158 the first portion may be calibrated before or after insertion, indicated as first portion 154". Calibration of the first portion following shipment may occur as noted above, by access to a network or cloud resource about factory calibration information, particularly where the same has been updated with data from sensors in the field.

FIG. 11 is a flowchart 160 illustrating the above-described method. First, a manufacturing lot or batch of sensors is manufactured under known and reproducible conditions at a factory (step 162). The lot or batch is divided into at least two portions (step 164). Two portions are described here for convenience, but it will be understood that the manufacturing lot may be divided for staggered release into any number of portions.

In this example, the second portion is sent to users (step 166). The second portion is then calibrated (step 168), and the calibration may occur in known fashion, e.g., using a priori information, bench calibration values, user data, finger stick calibrations, or the like. The calibration may also occur using techniques disclosed here.

The calibration information from the second portion may then be sent to the factory (step 170). The calibration of the first portion of the sensors may then be generated or adjusted based on data from the second portion (step 172). That is, if a factory calibration has been generated for the first portion, the same may be adjusted if required. If no factory calibration has been generated, received data from the second portion may be used to inform the calibration of the first portion, e.g., an average of determined sensitivities from the field, and so on. The adjustment or generation may occur at the factory (step 174), or the same may occur following shipment, before or after insertion in a patient (step 176), where the transmitter, receiver, or other monitoring device, e.g., smart phone, are in network communication with a server or other network resource operated by the factory 148.

Figure 12:
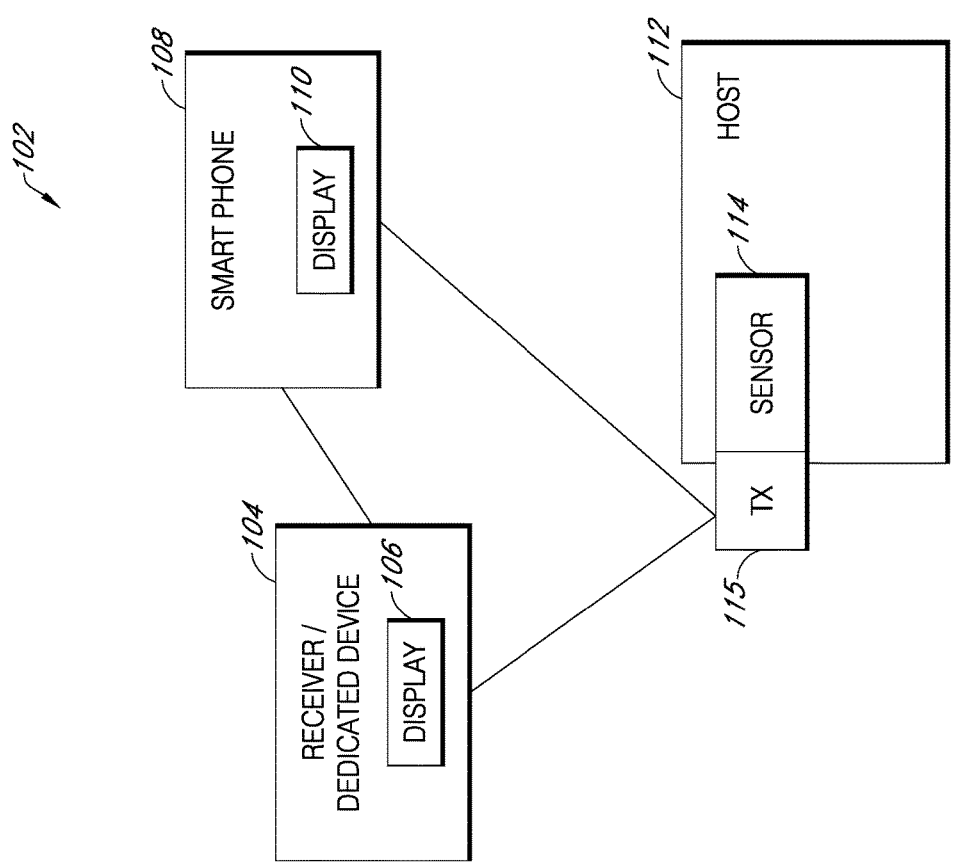
FIG. 12 is a schematic depiction of a sensor and transmitter within a host, communicating with a receiver and/or a smart phone.

Once sensors are inserted in a user and initial calibration is complete, any calibration from then on is termed "ongoing" or "continuing" calibration. Schematically this is illustrated in the diagram 102 of FIG. 12. A user, patient, or host 112 has an indwelling sensor 114, which is connected to a transmitter 115. In many cases the transmitter is used multiple times for different sensors. In other cases, the transmitter may be made disposable.

The transmitter 115 allows communication of signals measured by the sensor 114 to devices such as a receiver or dedicated device 104, or a smart phone 108. The receiver 104 is shown with a display 106, and the smart phone 108 is shown with a display 110. The displays 106 or 110 may be employed to indicate to the user clinical values of analyte concentrations, e.g., glucose concentrations. In doing so they rely upon the relationship noted above, that a measured current or counts is related to a clinical value of analyte concentration by a linear relationship having a slope representing the sensitivity.

Systems and methods according to present principles describe the development or determination of this linear relationship based largely or solely on characteristics of the sensor signal itself and do not rely, in some implementations, on external data, as prior systems did. In addition, such "self-aware" systems, employing "self" or "auto" calibration, may be employed not only to more accurately measure subsequent analyte concentrations but also to retrospectively modify results of prior measurements. In this way, when such is displayed on a display such as, e.g., display 106 or display 110, the same more accurately conveys measured data. Put another way, retrospective processing may be employed to correct or modify prior calibrations, and even to update data measured therefrom. In this way, if a display indicates historical data as well as current data, at least the historical data will be updated, i.e., the display of such will change, to reflect calibration parameters that are better known or known with more confidence than prior calibrations.

Figure 13:
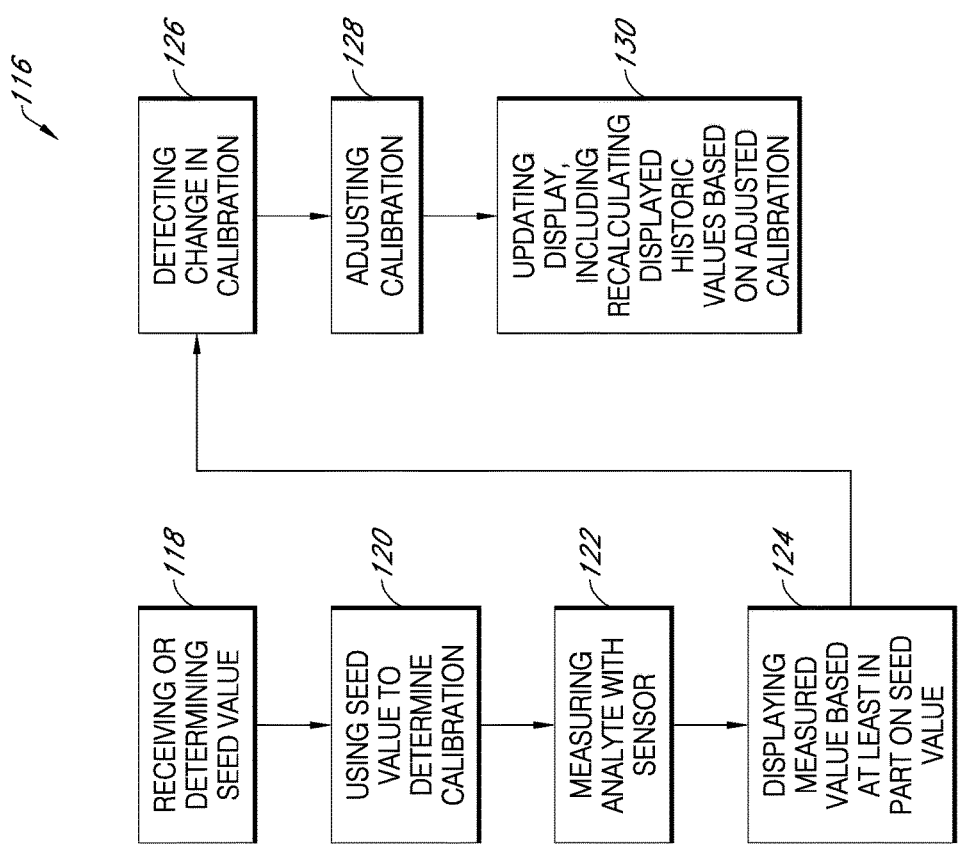
FIG. 13 is a flowchart illustrating another exemplary method according to present principles.

This method is illustrated by the flowchart 116 of FIG. 13, in which a first step is the reception or determination of a seed value (step 118), such as may be received or determined using the initial calibration procedures described above. The seed value may then be employed to determine the calibration (step 120). For example, if the received calibration parameter is a particular value of the slope or sensitivity m, then the same may be used to relate counts measured to a clinical value of analyte concentration, and may be used to begin immediately notifying the user of their measured analyte concentration, e.g., glucose measurement. That is, the analyte may be measured with the sensor (step 122), and the measured value may be displayed to the user based at least in part on the seed value received in step 118 (step 124).

In some cases a change in calibration will occur (step 126), and the same may be detected in various ways, including ways described below. The calibration, and in particular the calibration parameters including sensitivity and baseline, may then be adjusted (step 128). Upon the updating of the calibration parameters, the display may be updated (step 130).

As noted above, the updating of the display may not only refer to adjusting a currently measured value of analyte concentration, but also recalculating and thus changing the display of historic values based on the adjusted calibration. For example, a sensitivity may have been "seeded" by an initial value but following the receipt of data may be determined to actually be lower than the initial seed value by 10%. In this case, it is not just ongoing displayed analyte values that will be adjusted but also, in one implementation, historic values may be adjusted to reflect the updated sensitivity. This example illustrates a situation where a seed value is updated with the measured value. In some cases, a previously determined value (determined by seed or measurement) may be updated with a later determined value. This situation may arise, e.g., when a sensor calibration parameter "drifts". For example, if the calibration of the sensor is determined to have drifted, a change may be made to the calibration parameters such that the receiver, smart phone, or other monitoring device continues to display an accurate value of the analyte concentration. In one implementation, if it can be determined when the drift occurred, certain historic values may be updated in a display, i.e., those measured following the drift, while others need not be updated, e.g., those measured prior to the drift.

In one implementation, if the determined seed value and the initial seed value are close, e.g., within 10%, then the initial seed value (or other calibration parameter) may simply be adjusted accordingly. However, if the value is further away, then user may be prompted for intervention, e.g., by an optional finger stick.

Figure 14:
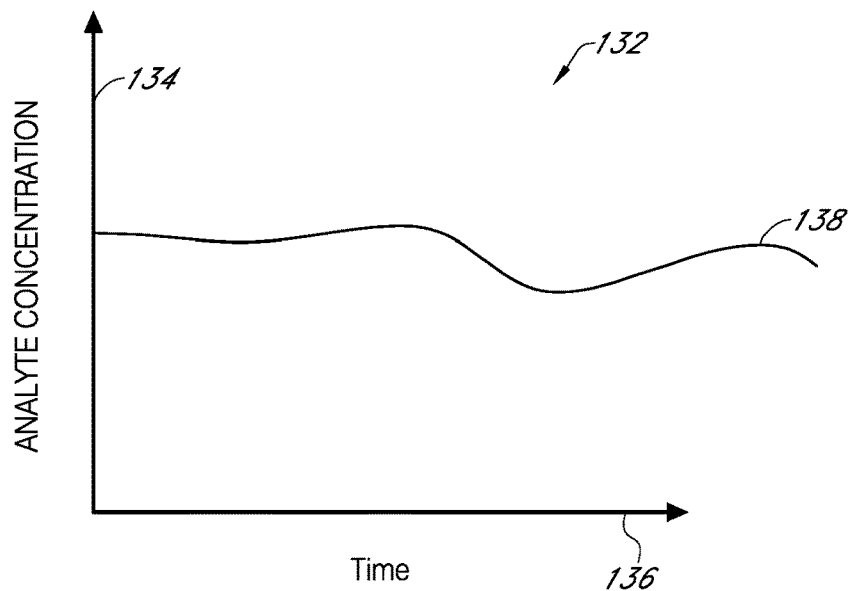
FIGS. 14 and 15 are graphs depicting an analyte concentration over time before (14) and after (15) a change in sensitivity.
Figure 15:
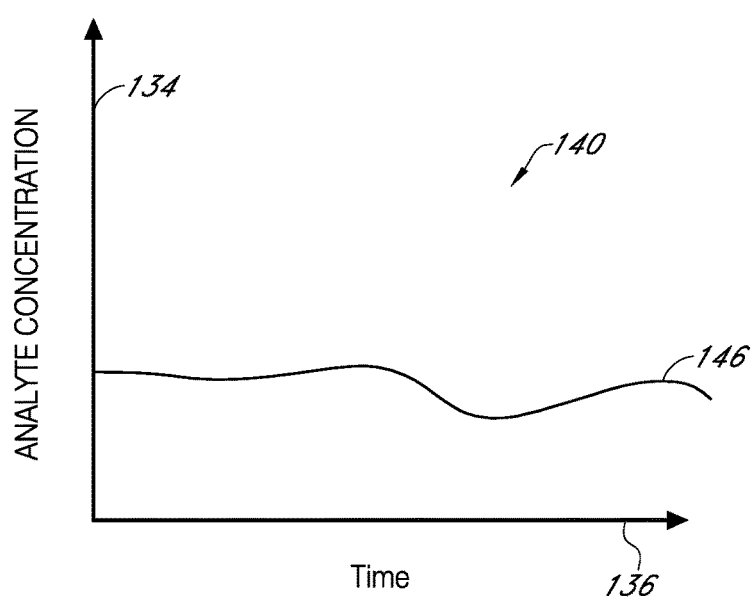

FIGS. 14 and 15 are graphs depicting an analyte concentration over time before (14) and after (15) a change in sensitivity. In particular, FIG. 14 illustrates a graph 132 in which a plot 138 is shown of an analyte concentration over time. The axis 134 represents values of the analyte concentration and the axis 136 represents time. Following a change in sensitivity, the graph becomes graph 140, with transformed historic analyte values 146. The change in sensitivity may be considered as an updated sensitivity or as an updated seed value, depending on implementation. Multiple other ways of adjusting calibration using sensor signal characteristics may be employed including, but not limited to, mean sensor signal, standard deviation or CV (coefficient of variation) or inter quartile range of sensor signal or other higher order or rank-order statistics.

In more detail, and in contrast to prior efforts, the preferred embodiments describe systems and methods for periodically or substantially continuously post-processing (e.g., updating) the substantially real-time graphical representation of glucose data (e.g., trend graph representative of glucose concentration over a previous number of minutes or hours) with processed data, where the data has been processed responsive to updates in calibration, e.g., as a result of sensor drift, system errors, or the like.

Figure 16:
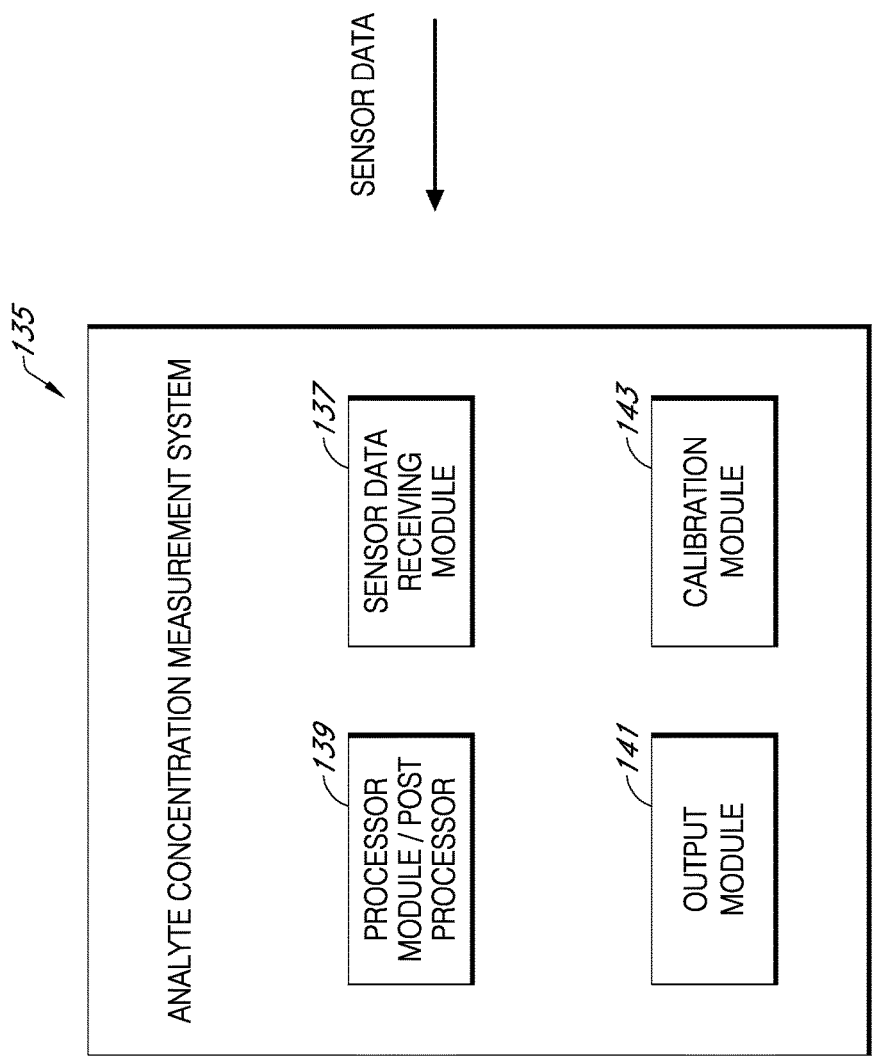
FIG. 16 is a modular depiction of an analyte concentration measurement system according to present principles.

Referring to the analyte concentration measurement system 135 depicted in FIG. 16, and in particular at block 137, a sensor data receiving module, also referred to as the sensor data module, or processor module, receives sensor data (e.g., a data stream), including one or more time-spaced sensor data points. In some embodiments, the data stream is stored in the sensor for additional processing; in some alternative embodiments, the sensor periodically transmits the data stream to the receiver or other monitoring device, such as a smart phone, which can be in wired or wireless communication with the sensor. In some embodiments, raw and/or filtered data is stored in the sensor and/or transmitted and stored in the receiver.

At block 139, the processor module is configured to process the sensor data in various ways. The processor module, in combination with a calibration module 143, may also be employed to determine whether a change in calibration has occurred, such as described in more detail above and below. In more detail, at block 143, a calibration module detects changes in calibration and more particularly changes in the sensitivity using data in the data stream.

At block 141, an output module provides output to the user via a user interface (not shown). The output is representative of the estimated glucose value, which is determined by converting the sensor data into a meaningful clinical glucose value. User output can be in the form of a numeric estimated glucose value, an indication of a directional trend of glucose concentration, and/or a graphical representation of the estimated glucose data over a period of time, for example. Other representations of the estimated glucose values are also possible, for example audio and tactile. In some embodiments, the output module displays both a "real-time" glucose value (e.g., a number representative of the most recently measure glucose concentration) and a graphical representation of the processed and/or postprocessed sensor data.

In one embodiment, the estimated glucose value is represented by a numeric value. In other exemplary embodiments, the user interface graphically represents the estimated glucose data trend over a predetermined time period (e.g., one, three, and nine hours, respectively). In alternative embodiments, other time periods can be represented. In alternative embodiments, pictures, animation, charts, graphs, ranges of values, and numeric data can be selectively displayed.

The processor module may further be configured to perform a step of postprocessing, e.g., may be configured to periodically or substantially continuously post-process (e.g., update) the displayed graphical representation of the data corresponding to the time period according to the received data, e.g., more recently received data. For example, the glucose trend information (e.g., for, the previous 1-, 3-, or 9-hour trend graphs) can be updated to better represent actual glucose values considering newly-determined calibration values. In some embodiments, the post processing module post-processes segments of data (e.g., 1-, 3-, or 9-hour trend graph data) every few seconds, minutes, hours, days, or anywhere in between, and/or when requested by a user (e.g., in responsive to a button-activation such as a request for display of a 3-hour trend graph).

In general, post-processing includes the processing performed by the processor module (e.g., within the hand-held receiver unit) on "recent" sensor data (e.g., data that is inclusive of time points within the past few minutes to few hours) after its initial display of the sensor data and prior to what is generally termed "retrospective analysis" in the art (e.g., analysis that is typically accomplished retrospectively at one time, in contrast to intermittently, periodically, or continuously, on an entire data set, such as for display of sensor data for physician analysis). Post-processing can include programming performed to recalibrate the sensor data (e.g., to better match to reference values), fill in data gaps (e.g., data eliminated due to noise or other problems), smooth out (filter) sensor data, compensate for a time lag in the sensor data, and the like. Preferably, the post-processed data is displayed on a personal hand-held unit (e.g., such as on the 1-, 3-, and 9-hour trend graphs of the receiver or smart phone) in "real time" (e.g., inclusive of recent data within the past few minutes or hours) and can be updated (post-processed) automatically (e.g., periodically, intermittently, or continuously) or selectively (e.g., responsive to a request) when new or additional information is available (e.g., new reference data, new sensor data, etc.). In some alternative embodiments, post-processing can be triggered dependent upon the duration of a change in calibration episode; for example, data associated with changes in calibration events extending past about 30 minutes can be processed and/or displayed differently than data during the initial 30 minutes of a change in calibration episode.

In one exemplary embodiment, the processor module filters the data stream to recalculate data for a previous time period and periodically or substantially continuously displays a graphical representation of the recalculated data for that time period (e.g., trend graph). In another exemplary embodiment, the processor module adjusts the data for a time lag (e.g., removes a time lag induced by real-time filtering) from data for a previous time period and displays a graphical representation of the time lag adjusted data for that time period (e.g., trend graph). In another exemplary embodiment, the processor module algorithmically smoothes one or more sensor data points over a moving window (e.g., including time points before and after the one or more sensor data points) for data for a previous time period and displays a graphical representation of the updated, averaged, or smoothed data for that time period (e.g., trend graph).

In some embodiments, the processor module is configured to filter the sensor data and to display a graphical representation of the filtered sensor data responsive to a determination of a start of a change in calibration event. In some embodiments, the processor module is configured to display a graphical representation of unfiltered data (e.g., raw data) responsive to a determination of an end of a change in calibration event. In some embodiments, the processor module is configured to display a graphical representation of unfiltered data except when a change in calibration event is determined. It has been found that adaptive filtering as described herein, including selective filtering during a change in calibration events, increases accuracy of displayed data, decreases display of noisy data, and/or reduces data gaps and/or early shut off as compared to conventional sensors.

Calibration Routines

As noted above, it is desirable to provide a more convenient calibration routine for users, and especially for type II users or for those using the system for weight loss optimization and/or sports and fitness optimization.

One way of reducing the need for user-based calibration is by employing more enhanced factory calibration, and certain details about methods associated with factory calibrations may be found in U.S. Ser. No. 13/827,119, filed Mar. 14, 2013, published as US 2014-0278189-A1; and U.S. Ser. No. 62/053,733, filed Sep. 22, 2014, both of which are owned by the assignee of the present application and herein incorporated by reference in their entirety.

Figure 17:
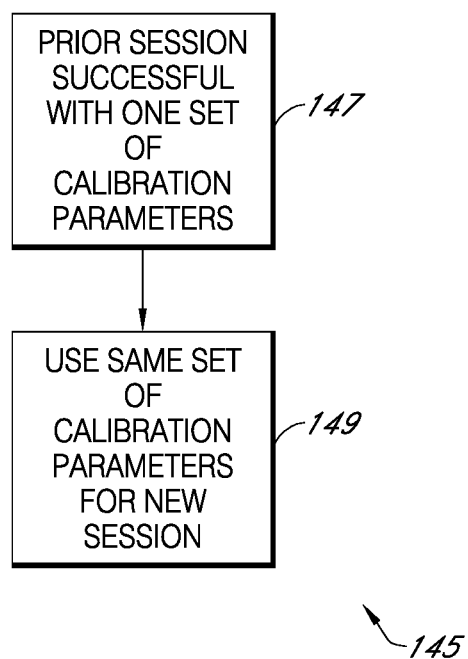
FIG. 17 is a flowchart illustrating another exemplary method according to present principles.

Other techniques may also be employed to ease calibration requirements. For example, referring to the flowchart 145 of FIG. 17, if a prior sensor session showed generally reliable results (step 147), the same calibration parameters may simply be employed from the prior session into a new sensor session (step 149). In particular, the calibration parameters from the old sensor session may be transmitted to the new sensor session in a number of ways, e.g., by employing the glucose signal transmitter technology, if the calibration parameters are stored on the sensor electronics, or by passing the calibration state variables on to the new session if the calibration parameters are stored in the monitoring device, e.g., smart phone. This technique may be particularly useful if the sensors are in some way related, e.g., from the same batch, the same package, of the same type, or the like.

This technique is not necessarily limited to just the use of a single prior sensor session, e.g., going back just one session. For example, repeated patterns, e.g., historic patterns, may be learned by analysis of several prior sensor sessions. For example, the system may learn that the user is accustomed to eating pizza on Friday, and has done so over the last seven sessions, and an algorithm may thus learn to not treat such events as outliers. Patient habits could also be learned, e.g., that the patient likes to eat many small meals versus just a few large ones. Failure modes could also be learned, e.g., if the patient tends towards a particular failure mode due to a particular way of installing and/or using their device. As discussed below in connection with FIG. 18, certain glucose trace characteristics, constituting repeatable events, may be advantageously learned from prior sensor sessions, and in many cases multiple prior sensor sessions are necessary to distinguish common events from outliers. In addition, where other event data is available, e.g., meal or exercise data, correlations between such repeatable events and the entered meal or exercise data may be learned.

Figure 18:
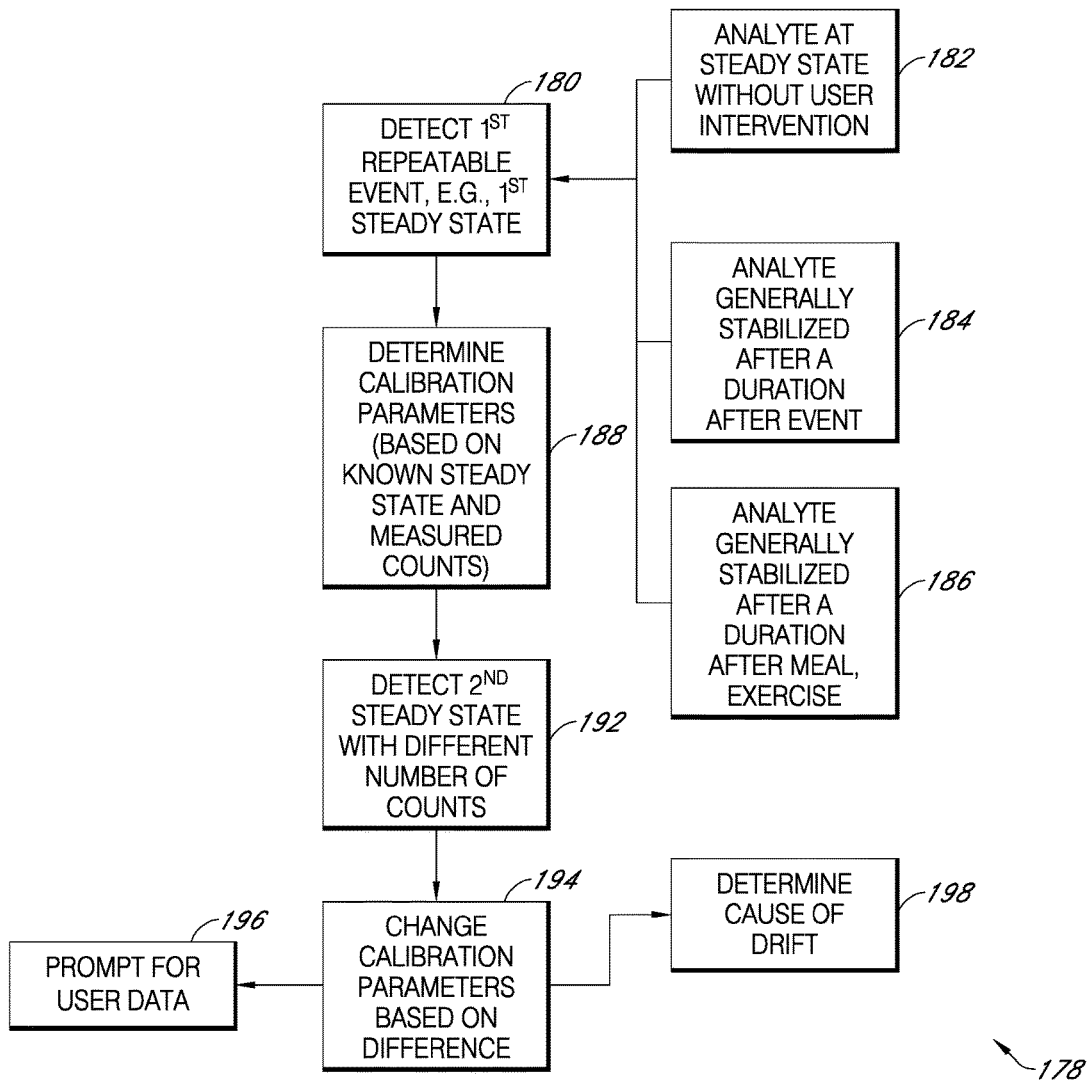
FIG. 18 is a flowchart illustrating another exemplary method according to present principles, employing a steady-state to perform calibration.

Next, referring to FIG. 18, a flowchart 178 is shown for another method of calibration. In particular, it is known that certain glucose trace characteristics are indicative of repeatable events that, if they recur, recur at known and repeatable glucose values. As examples, steady-state values, certain trend values including certain slopes, and so on, tend to be reproducible for a given patient. Such repeatable events tend to give rise to repeatable and detectable characteristic glucose trace signatures and/or patterns. For example, it is characteristic of many biological systems that analyte values, if not changing rapidly, i.e., are at a steady state, are highly reproducible. In other words, if an analyte value is at a steady state over a first time, and subsequently is at a steady state over a second time period, then the value of the analyte, e.g., concentration, is generally at or near the same value, in each of the steady-state time periods. This concept can be employed to calibrate analyte sensors.

For example, if a user is in a steady state with respect to an analyte, the value of the analyte can be measured and stored. When the user is again at a steady state, it is highly likely their analyte value is the same as the value measured previously, and thus a sensor, reading the analyte concentration value, can be calibrated.

Different analytes may achieve different steady states in various ways. For example, uric acid concentration changes very little throughout a typical day. If the user has not exercised and not eaten for several hours, their glucose value may be at a steady state. If the user has not exercised for several hours, their lactate value may be at a steady state. In general, if a biological system has not significantly changed state over a period of time, many analyte values, including glucose, will achieve a steady state. As noted the steady-state value is reproducible, especially for pre-diabetics, or nondiabetics, as well as for those who are using the system primarily for weight loss optimization or sports optimization. Thus, whenever a steady-state is detected in an analyte value, the sensor measuring the analyte can be calibrated.

In some cases the system may prompt a user to fast from food or exercise in order to achieve a steady-state, which can then be measured and employed subsequently for such calibrations. Moreover, the system may detect a steady-state but prompt the user for verification, e.g., by asking the user "have you been fasting?".

In some cases, a steady-state value may be determined based on demographics of the user, thus not requiring any measurement at all. For example, for nondiabetics a typical glucose value may be between about 80 and 100 mg/dL. In many cases, if a person is very nondiabetic their value may be about 80, while if they are progressing toward prediabetes their value may approach 100. Thus just providing the system with certain information about a user may allow a degree of calibration to be performed, particularly for certain applications, including where the user does not need to have accuracy determined to a precise value, but rather where accuracy only to a particular range is sufficient, e.g., hypoglycemic, hyperglycemic, or euglycemic.

Besides steady-states, other repeatable events that may be employed include slopes, responses after typical or similar meals, e.g., responses after breakfast if the user eats the same sort of breakfast every day. Other repeatable events include a range of low measurements to high measurements, e.g., on a daily basis, i.e., a daily high to low range, certain types of excursions, certain types of transient patterns, decay rates and slopes, rates of change, and the like.

As a particular example, if a user has a characteristic breakfast, and the characteristic breakfast leads to a characteristic postprandial glucose trend, then if a change in the trend occurs, it may be assumed that, at least to some degree, a change in sensitivity of the sensor has occurred and the sensor needs to be recalibrated.

Additional data may be employed to help the calibration as well. For example, if the user is a diabetic and is measuring their blood glucose several times a day anyway, such values may be employed as calibration values. This is particularly true if their blood glucose value varies significantly. In this case, if the system detects a local steady-state, the system can prompt the user to measure and enter a blood glucose value in order to correlate a value with the steady-state.

Historical data may in some cases be employed to determine steady-state calibration values, e.g., prior data from blood records, data from a prior session, estimations from measurements such as A1C that track long term glucose averages, or the like.

In some cases it is not necessary to hone in on a particular value. Determination that a user is in a range of values may be sufficient for type II users. The range may be determined and used in providing the user with information about whether goals are being met, or other information about the program they are on.

Use of steady state assumptions may be employed not just for initial calibration but also for update calibrations. That is, whenever the system is seen to be in a subsequent steady-state, the value measured during the subsequent steady-state may be assumed to be that determined originally for the user. Other calculations may also be employed, including using weighted averages, slow moving averages (see below), and the like.

Referring to FIG. 18, the method of flowchart 178 allows the calibration of glucose concentration or other analyte values using information generated directly from the device, i.e., the analyte concentration signal, itself.

Thus, referring to the flowchart 178, a first step in a calibration routine according to these principles is to detect that a system is in a steady-state (step 180), e.g., a first known steady state.

Commonly a steady-state may be detected without any action by the user at all (step 182). However in some cases a steady-state may be prompted by waiting a predetermined period of time after an event to allow a steady-state to be achieved (step 184), e.g., by waiting a predetermined period of time following a meal or exercise routine (step 186). The system or routine may ask or prompt for user information, e.g., about fasting, e.g., prompting the user to enter a duration since their last meal or related parameters. In the case of glucose the routine may be configured to look for a low rate of change, or a rate of change below a predetermined value, e.g., less than 0.25 mg/dL per minute. In some cases, where calibration has not yet occurred, the rate of change may be based on counts or microamps or other "raw" signal value. The rate of change may be determined by calculation of a derivative.

Once a steady state has been detected, calibration parameters such as sensitivity may be determined (step 188) based on the measured number of counts (or on current) at the steady state and the known steady state glucose value, which may be known or assumed. Subsequently, another steady state may be detected (step 192), and where drift has occurred the second steady state will be associated with a different number of counts. The different number of counts may be used to determine a degree of drift, and the system may be recalibrated (step 194) using the new (second) number of counts measured at the new (second) steady state, along with the previously-known steady state glucose value.

In some cases, where the change is substantial, e.g., exceeds a predetermined threshold, the user may be prompted for additional data (step 196), e.g., a finger stick, data about exercise or meals, and so on. The difference may also be employed to determine a cause of the drift (step 198).

A particular example is now described. A continuous glucose monitor may be used for a patient without diabetes. In patients without diabetes, their glucose values are typically in the 70 to 90 mg/dL range. Their glucose level deviates from this range only after meals or during extreme exercise, and in some cases such deviations may be detected by changes in the sensor signal or via auxiliary measurements using heart rate monitors and accelerometers. During these glucose excursions, the current measured by the sensor will be changing rapidly which can be easily detected by the monitoring device. The rate of change can be calculated using, e.g., an FIR filter over the last 20 minutes of glucose values, but can be extended to a simple rate of change as defined as the difference between two glucose values, at the start and end of a time period, divided by the duration of the time period. During rapid rates of change, the systems and methods according to present principles, if using steady-state occurrences as a repeatable event for calibrations, can avoid using such rapidly-changing data in calibrations, but rather may wait until the value is stable before performing a calibration event (as noted certain calibration methods may take advantage of such—e.g., as noted above, in some cases a repeatable event usable for calibration may include transient noise events or patterns—i.e., certain aspects of high variation areas or peaks may be useful for non-steady-state repeatable event calibrations, and in many cases transient events, including rapid or slow rates of change of analyte concentration values, may form signal characteristics from which patterns are deduced and used as repeatable events). In one example, an absolute rate of change threshold may be set at 0.25 or 0.5 mg/dL/minute over the last 25 minutes of glucose data. As above, uncalibrated units may also be employed. Thus, calibration may be prohibited if the absolute rate of change threshold is exceeded. In other implementations, different calibration values may be used, and the same may also be configured to depend on the direction of rate of change, or the calibration value used could be a function of the rate of change itself.

Figure 19:
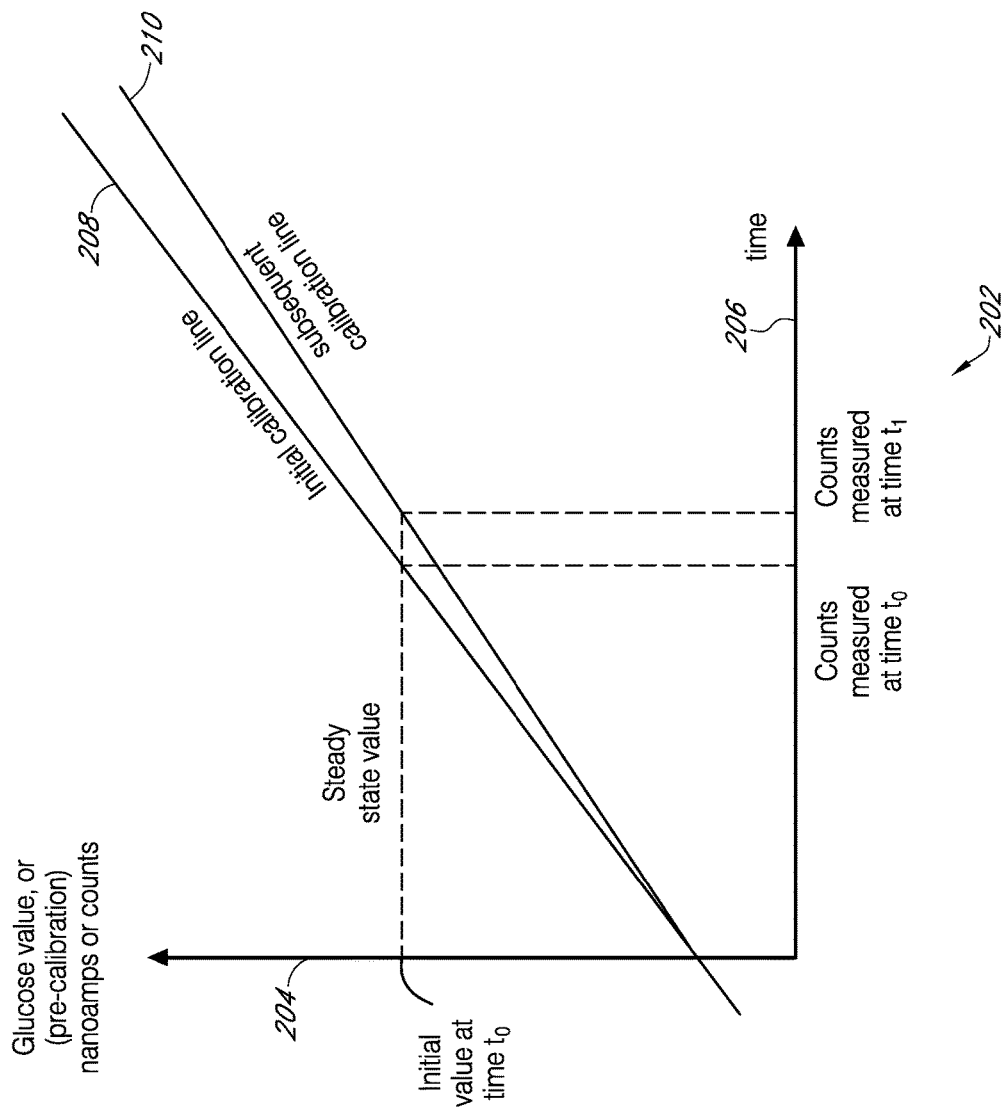
FIG. 19 is a graph illustrating two calibration lines, before and after a drift has occurred.

Referring to FIG. 19, and as noted with respect to step 194 of FIG. 18, steady states may be used to update calibration values as well as to determine initial ones. Moreover, the system may be employed even as calibration parameters change, e.g., as a sensor enzyme layer is altered over time with use, or as other drift occurs. For example, referring to the graph 202 of FIG. 19, the value of an analyte may be associated with either a calibrated value or uncalibrated value at a time $t_0$ (axis 206), and this steady-state value may be assumed to be reproducible whenever the user is at a steady-state in that analyte value. This knowledge can lead to an initial calibration line 208, which slope is the sensor sensitivity if the axis 204 has units of counts. At a subsequent time $t_1$, which is also assumed to be in the steady-state, even if the number of measured counts is different, knowledge of the same steady state value allows a subsequent calibration line 210 to be drawn and thus the system can be recalibrated. The degree of recalibration needed may be highly useful in the determination of the cause and treatment of drift.

Systems and methods according to present principles may be most effective when the baseline or background signal is sufficiently stable and predictable (or eliminated through advanced membrane or sensor technology). When the sensor starts up, a current is generated. If the baseline is sufficiently small or estimated with sufficient accuracy, then the remaining current will be from the analyte of interest. The algorithm may measure the current over a set period of time and if the current is stable, e.g., within prescribed limits, then the algorithm may assume that the glucose (or other analyte) is not changing and is within a narrow range. The algorithm may then calibrate the device automatically using a glucose value of approximately, e.g., 80 mg/dL (or whatever is determined to be the typical value for the user) and correlating that to the current that is generated during that time with stable glucose. In one implementation, a glucose value was set at 100 mg/dL (it is reiterated that the same can change depending on factors such as rate of change, duration of wear, time of day, characteristics of the user, e.g., state of progression toward diabetes, and so on). The systems and methods may employ a regression model to calculate the slope and baseline with two points. The first point being a current generated during the stable glucose (and the approximated glucose level of a user without diabetes) and the second point being zero glucose (using an estimated value for the background signal). The slope of the line may be determined using, e.g., a weighted average, of a regression slope (counts/assumed to BG) and the previous slope estimate. Subsequent to the calibration, glucose data may be presented to the user. The baseline of this implementation was assumed to be zero, however, a different nonzero baseline value could be used. Calibration may also be updated periodically, e.g., every few minutes or every few hours, depending on implementation.

The above technique may be employed in combination with factory calibration information generated during the manufacture of the device or it could also be used with externally-generated glucose information, and may further account for changing sensitivity over time by incorporating pre-prescribed drift curves or other drift compensation techniques, as described in greater detail in U.S. application Ser. No. 13/446,848, filed Apr. 13, 2012, and published as US 2012-0265035-A1, owned by the assignee of the present application and herein incorporated by reference in its entirety.

Systems and methods according to present principles may further be employed to use calibration information about one sensor to calibrate another, e.g., an adjacent sensor, e.g., one under the same membrane. Such calibration may be performed as drift parameters, if caused by the membrane, may be assumed to be the same for both sensors. For example, if both sensors are under the same membrane layer, e.g., a glucose sensor and a lactate sensor, and if one or more calibration parameters were determined ex vivo, then the calibration parameters may be assumed to bear a similar relationship in vivo, and thus the measurement of one can be used to determine the other. For example, if the lactate sensor has a known offset in calibration from the glucose sensor (or other relationship or scaling or correlation factor), as measured ex vivo, then in vivo, a determination of calibration for that glucose sensor may be employed to calibrate the lactate sensor. For example, if calibration of the glucose sensor is seen to drift by 50%, then the calibration of the lactate sensor may be assumed to have drifted by 50%. Consequently, an update of one or more calibration parameters of one sensor can result in the update of one or more calibration parameters of the other sensor.

Additional details of such aspects may be seen in U.S. application Ser. No. 12/770,618, filed Apr. 29, 2010, published as US-2011/0004085-A1; and U.S. Ser. No. 12/829,264, filed Jul. 1, 2010, published as US-2011/0024307-A1, and [545PR], all of which are owned by the assignee of the present application and herein incorporated by reference in its entirety.

In addition, systems and methods according to present principles may use factory calibration information to start and then incorporate an automatic calibration technique over time to get more accurate glucose information. If the signal did not follow pre-prescribed parameters, or was outside of pre-prescribed parameters, the system could request a calibration value using known techniques, e.g., SMBG or finger stick calibrations. The systems and methods may then incorporate this glucose information into the original parameters to adjust the setpoint from, e.g., 100 mg/dL, to a more appropriate and accurate value. That is, while the above techniques intended for use in certain applications may be generally configured to avoid the need for finger stick calibrations, if such are available, systems and methods according to present principles may apply the same advantageously, for calibration purposes and otherwise.

Systems and methods according to present principles may be configured to determine a confidence level or range, and as the resolution or accuracy of the data changes, the confidence level or range can change. In more detail, the display could generate a value and a trend graph or the same may show a range or other UI element. The range may change over time and shrink or expand as a confidence in the accuracy changes. For instance, during initial warm-up, a factory calibration value may be utilized. However, its accuracy may not be as precise as it would be with additional information. During this time, the display may show a range rather than a value.

A further feature of systems and methods according to present principles are that they may request information when a user is set up within the system and adjust which technique to use depending on the information. For example, the system may prompt the user to enter whether they have type I diabetes, type II diabetes, or are nondiabetic, and may select a different technique depending upon the answer. Systems and methods according to present principles may further ask if the user is interested in weight loss optimization, sports and fitness optimization, or other like optimization routines, and may adjust the algorithm accordingly. The device may also, e.g., be used in a "blinded" mode for an extended period of time, e.g., 14 days, and only accept blood glucose values. These blood glucose values could be used to learn what a patient's resting blood glucose is, which could better guide the assumption of the auto calibration steady-state blood glucose value. After the extended period of time, the user could then use the device in auto calibration mode.

Figure 20:
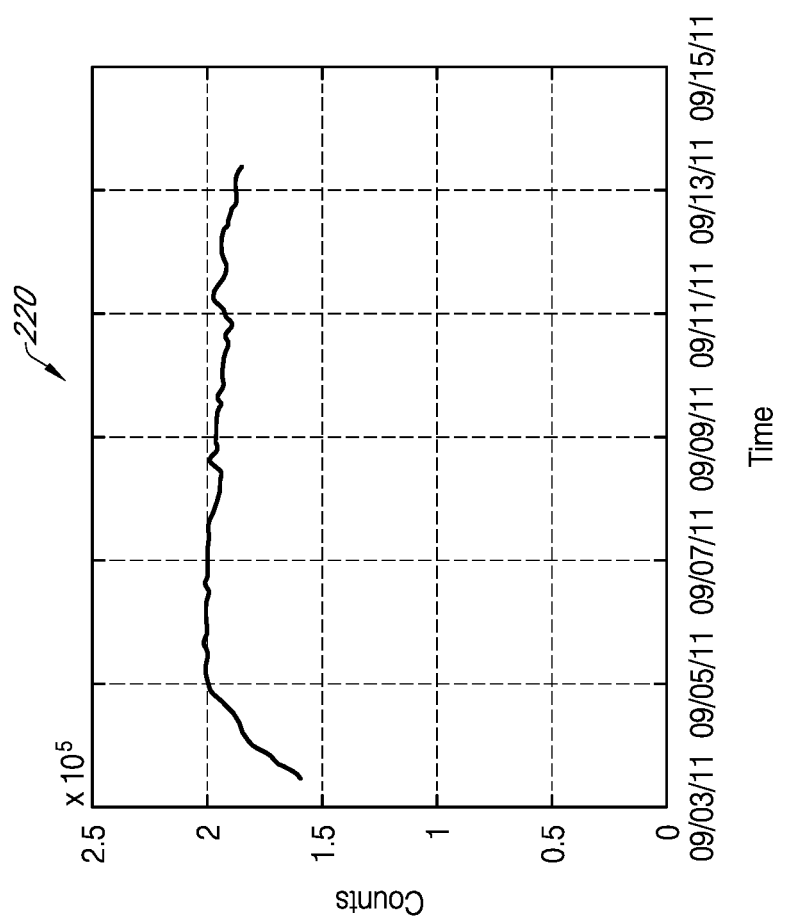
FIGS. 20 and 21 illustrate a slow-moving average of sensor count over time.
Figure 21:
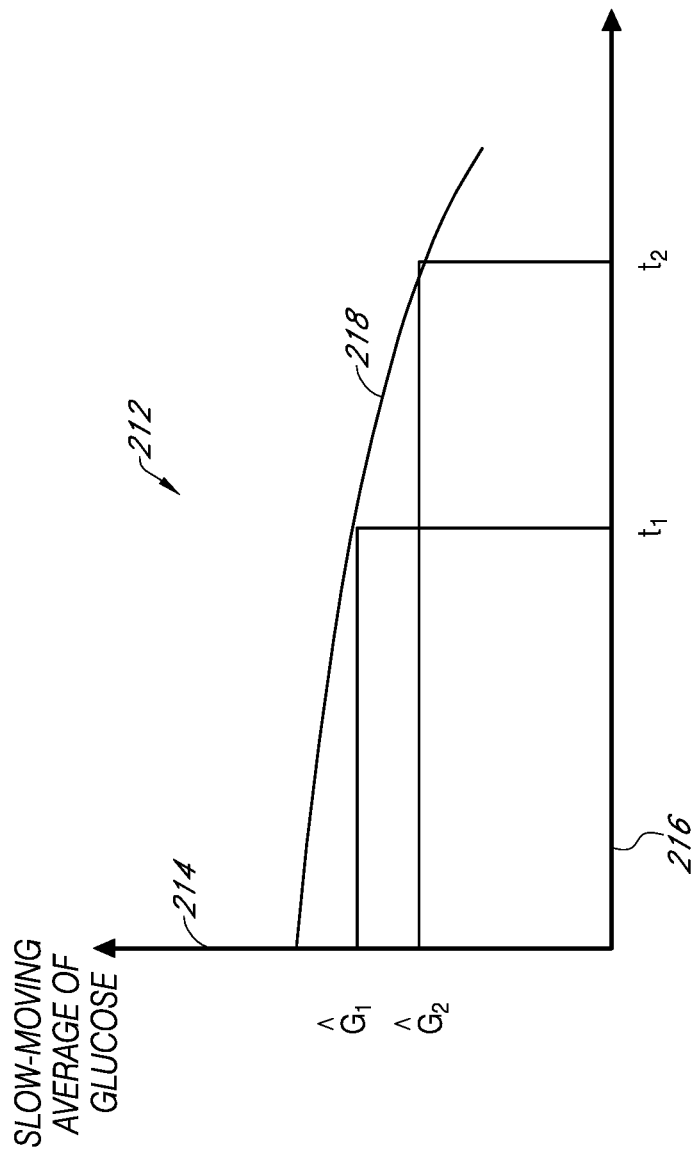

Besides the use of properties of the steady state value of analytes to glean additional information, "slow moving averages" may also be employed, i.e., average values taken over, e.g., 1-3 days, as such slow moving averages are also generally constant, particularly over the use of a sensor session. Thus, variations in the same can be used both qualitatively and quantitatively to detect and quantify drift. For example, values of a slow moving average of a glucose concentration are shown by the graph 220 in FIG. 20 and the more schematic graph 212 in FIG. 21, where sensor counts are shown on axis 214 versus time on axis 216. As may be seen, a slow moving average G1 measured at time $t_1$ may decrease to a slow moving average G2 at time $t_2$. The slow moving average may be used to quantify drift because the selectivity to glucose of an advanced sensor is high, therefore, the only thing contributing to the change in the slow moving average is the sensitivity.

While details of the use of slow-moving averages are described in detail below, it is noted here that the same need not be of a contiguous period of time. For example, a slow moving average may be taken by sampling a common time period over a number of days. For example, a slow-moving average may be taken of nighttime time periods, and such may then consider only, e.g., an 11 pm-7 am time period. The slow moving average would then constitute an average of data taken only during this time period, but over the course of several days. Other exemplary time periods in which such discrete or non-contiguous slow moving averages may be taken may include, e.g., post-prandial time periods, and so on. Such events could be time-based where the user has a very consistent timing of such events, or alternatively event based, e.g., where events are marked or tracked by one or more sensors. For example, an exercise event could be marked by an accelerometer, a meal event could be marked by detecting a glucose spike, and so on.

In more detail, in lieu of the use of a daily average, a time period may be employed over which an average is taken that is specific to a qualitative or quantitative type of time period that is specific and important to a user, e.g., making specific the time window looked at over which the average is taken. For example, a time window may be considered of "four hours after meals". The time period data can be used as measured over a number of days, but only looking at that particular time period, and thus only measuring variations from the average of the glucose response during that particular set of time periods. Put another way, the average may be determined by stitching together and averaging all of the glucose values from the individual time periods over the course of several days. In this way, if a drift is detected, the same is defined with respect to the average obtained by taking an average over such similar time periods. For example, a patient's daily average may be 100, but their nighttime average may be 85, and their "regular" waking daytime average is 120. Measurements of drift may be taken with respect to this defined "localized" average. Exemplary time periods may include, e.g., after dinner, 9 am to noon, sleeping, and so on.

The slow moving average may be taken of calibrated or even uncalibrated values, though by itself a slow moving average may need additional data to perform an initial calibration. For this reason implementations may include determining an initial glucose value using other methods, and obtaining, e.g., a days' worth of data, from which an initial slow moving average may be determined and then compared to subsequently-measured slow moving averages to determine, e.g., sensitivity drift corrections and the like. Such systems and methods may be particularly beneficial as the slow moving average can be checked very often compared to prior systems, e.g., every 5 minutes, as opposed to SMBG calibrations, which can only be done as often as the user is willing to take the reading.

Figure 22:
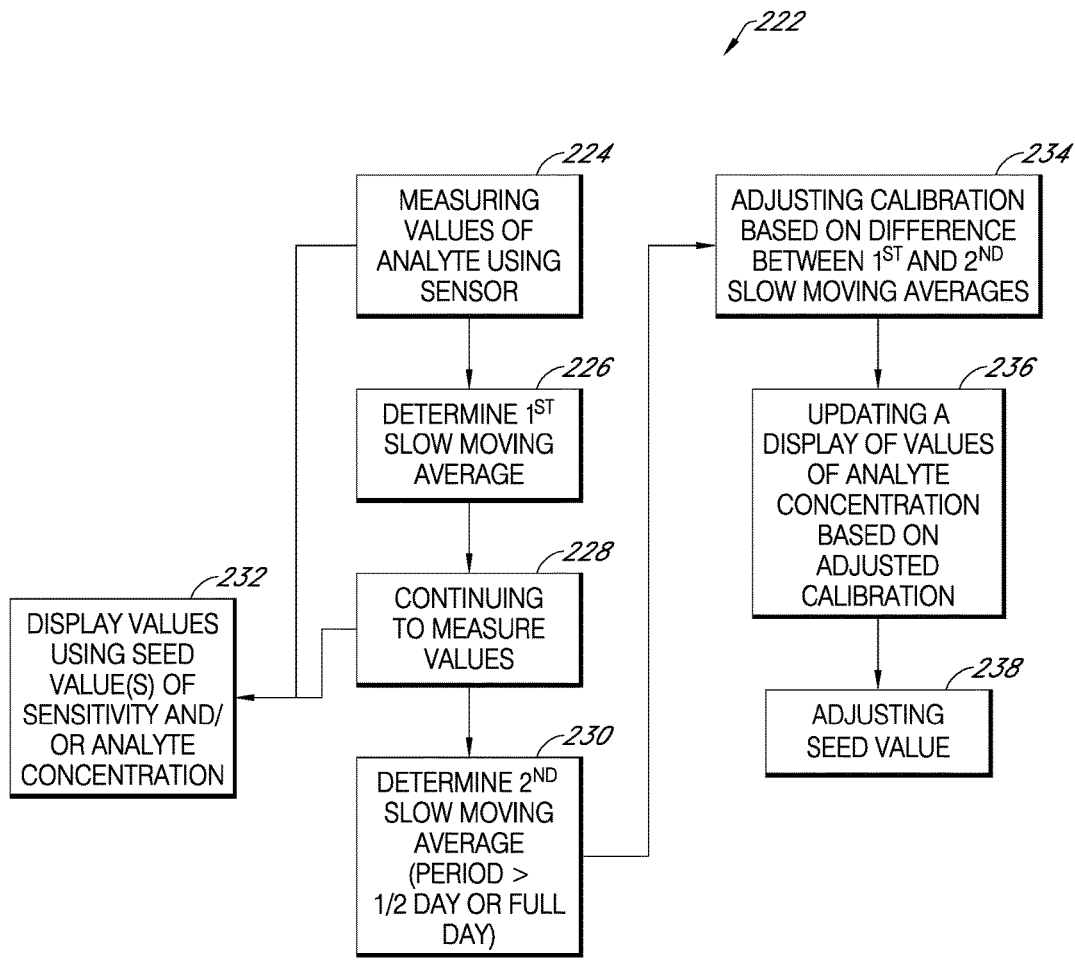
FIG. 22 is a flowchart illustrating another exemplary method according to present principles, employing a slow-moving average.

The flowchart 222 of FIG. 22 illustrates one implementation of the use of slow moving averages. In a first step, analyte values are measured using a sensor (step 224). A first slow moving average may then be determined (step 226). Analyte values may then continue to be measured (step 228), and the same may form the basis for displayed values of the analyte concentration (step 232), where the displayed values are based on an initial (or subsequent) value of the sensitivity. Second and subsequent slow moving averages may be determined (step 230), where the period of the slow moving average is generally greater than ½ day, e.g., 1-3 days. The slow moving averages may be taken as often as desired, e.g., every 5 minutes, every hour, and so on. In some implementations the time constant of the filter may be changed, e.g., if the user is having an actual high, and thus the effect (the high analyte concentration of the user) does not represent an actual drift or change in sensitivity of the filter. The use of a slow moving average may also be replaced by other forms of filtering such as order statistic filtering or time domain filtering.

If the first and second values (or second or subsequent values, or indeed any set of values) of the slow moving averages varies, then in one implementation a drift may be assumed to have occurred, and calibration may be adjusted (step 234) based on the drift, e.g., the difference between the slow moving averages. Implementations described below discuss other potential causes of variations in a slow-moving average. The display may be updated based on the recalibrated sensor (recalibrated based at least in part on the measured drift) (step 236). In some cases, the seed value (or other value used to base the display) may also be modified (step 238) to reflect (and compensate for) the drift.

Figure 23A:
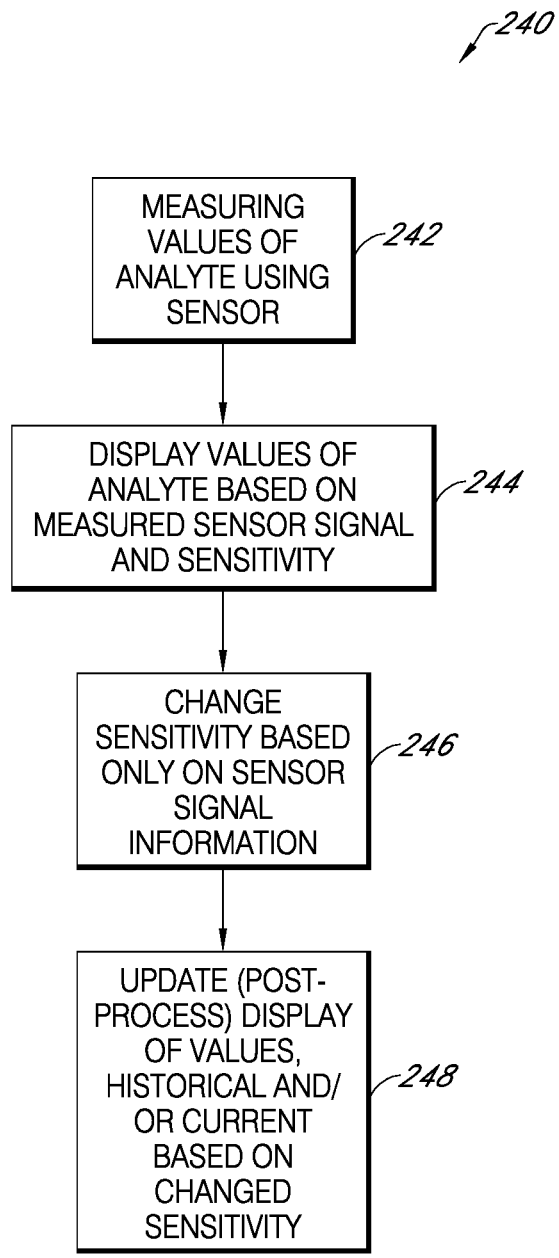
FIG. 23A is a flowchart illustrating another exemplary method according to present principles, illustrating updating of historical values.

Referring to the flowchart 240 of FIG. 23A, recalibrations based on data gleaned from the change of a slow moving average (or other recalibrations) may be also be used in post-processing to update the display of historic, here defined as "already displayed", values based on the recalibration. In a first step, values of an analyte concentration may be measured by a sensor (step 242). The values measured may be displayed as clinical values based on a calibration, e.g., based on a previously-determined value of sensitivity (step 244). The sensitivity may change based on sensor signal information (step 246), including based exclusively thereon, e.g., based on a change in a slow moving average or steady state value. The display may then be updated based on the change (step 248), and in particular historic already-displayed values may be redisplayed based on the recalibration, such that the historic values are represented more accurately. Other forms of detecting sensitivity changes (or drift) using signal characteristics (or features) include CV (coefficient of variation), standard deviation, or inter-quartile range of the signal and its relationship corresponding parameter of glucose.

Once a change has been detected, the same may be analyzed or 'discriminated' to determine the cause and/or magnitude of the change. It is common to find changes in sensitivity due to drift, but the same may also have other causes, including pump problems, e.g., blocked tubes, or other problems, e.g., membrane breaches, or the like. And it is further desirable to distinguish these changes from those due to actual changes in glucose value. At least as a first step in this latter determination, measured changes in glucose values can be compared to thresholds for such changes which are physiologically feasible. If the change is not physiologically feasible, then the change may be considered to be, at least in part, due to a drift or system malfunction.

Another way to discriminate signal drift behaviors is by comparing a signal drift curve to known signal drift curves, and in particular to a plurality or envelope of such curves. FIG. 4 illustrates one such curve, but for a given type of sensor, an envelope of such curves exists, i.e., there exists a pattern to how sensitivity changes. If the way in which the sensitivity is changing follows one of these curves, then it may be inferred that the change is due to a sensitivity drift and not an actual glucose value change or a system malfunction. Additional details about sensitivity profile curves are described in, e.g., U.S. patent application Ser. No. 13/796,185, entitled "Systems And Methods For Processing Analyte Sensor Data", filed Sep. 19, 2013, owned by the assignee of the present application and herein incorporated by reference in its entirety.

If the sensitivity changes by shifting to another of the known sensitivity curves, known calibration parameters for that curve may be employed in subsequent data analysis and display. If the sensitivity changes outside of the bounds of the known sensitivity curves, then it may be inferred that the changes are due to system issues or malfunctions as noted above, e.g., errors or artifacts. However, in certain implementations, a certain sensor may have sensitivity curves that are known to be within a band. Known failure modes may cause the sensitivity to shift, either to another curve within the band or to another band, i.e., the sensitivity may shift in a known failure mode to one of a known separate discrete band of curves.

Figure 23B:
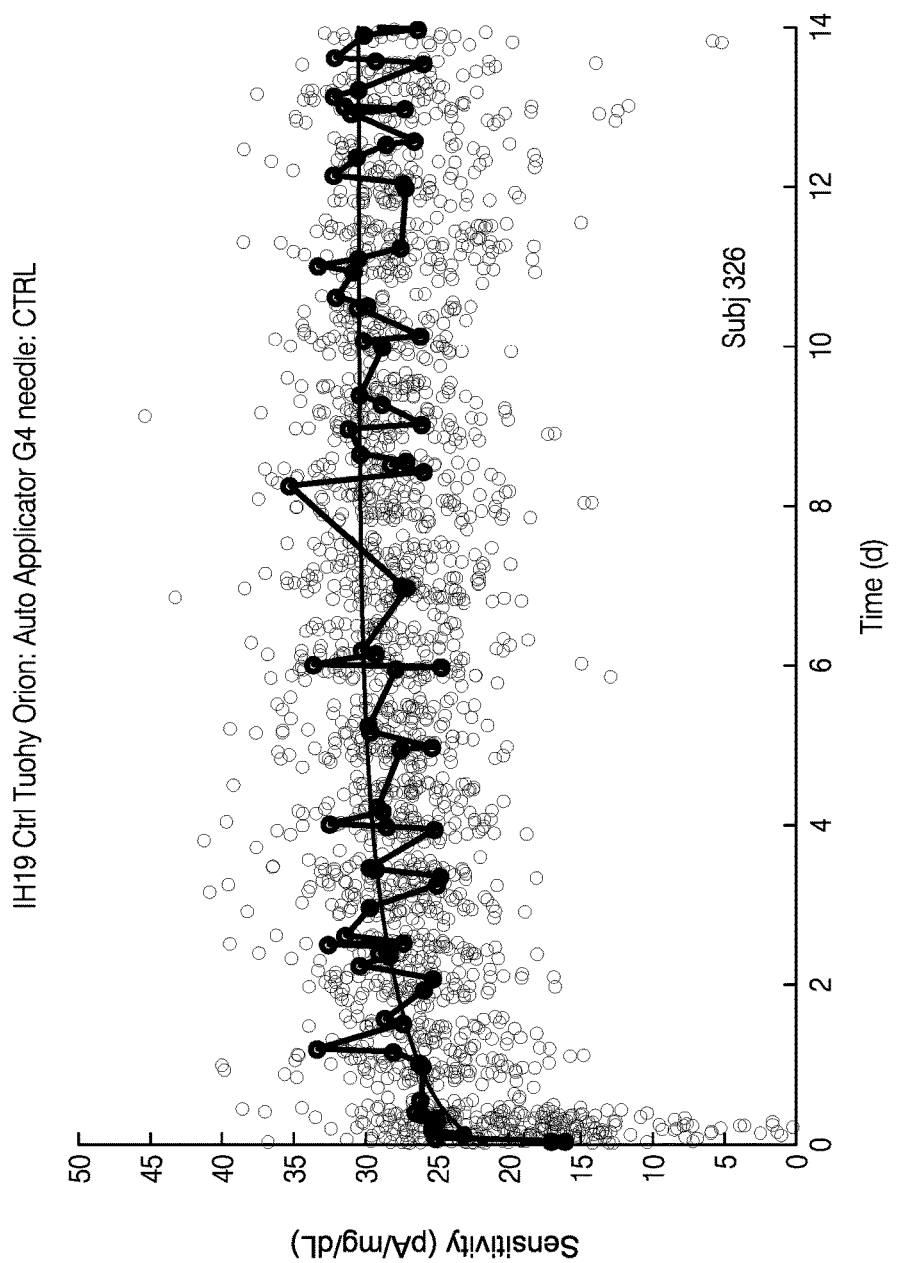
FIG. 23B is a chart showing sensitivity data over an extended sensor session, showing a characteristic drift.
Figure 23C:
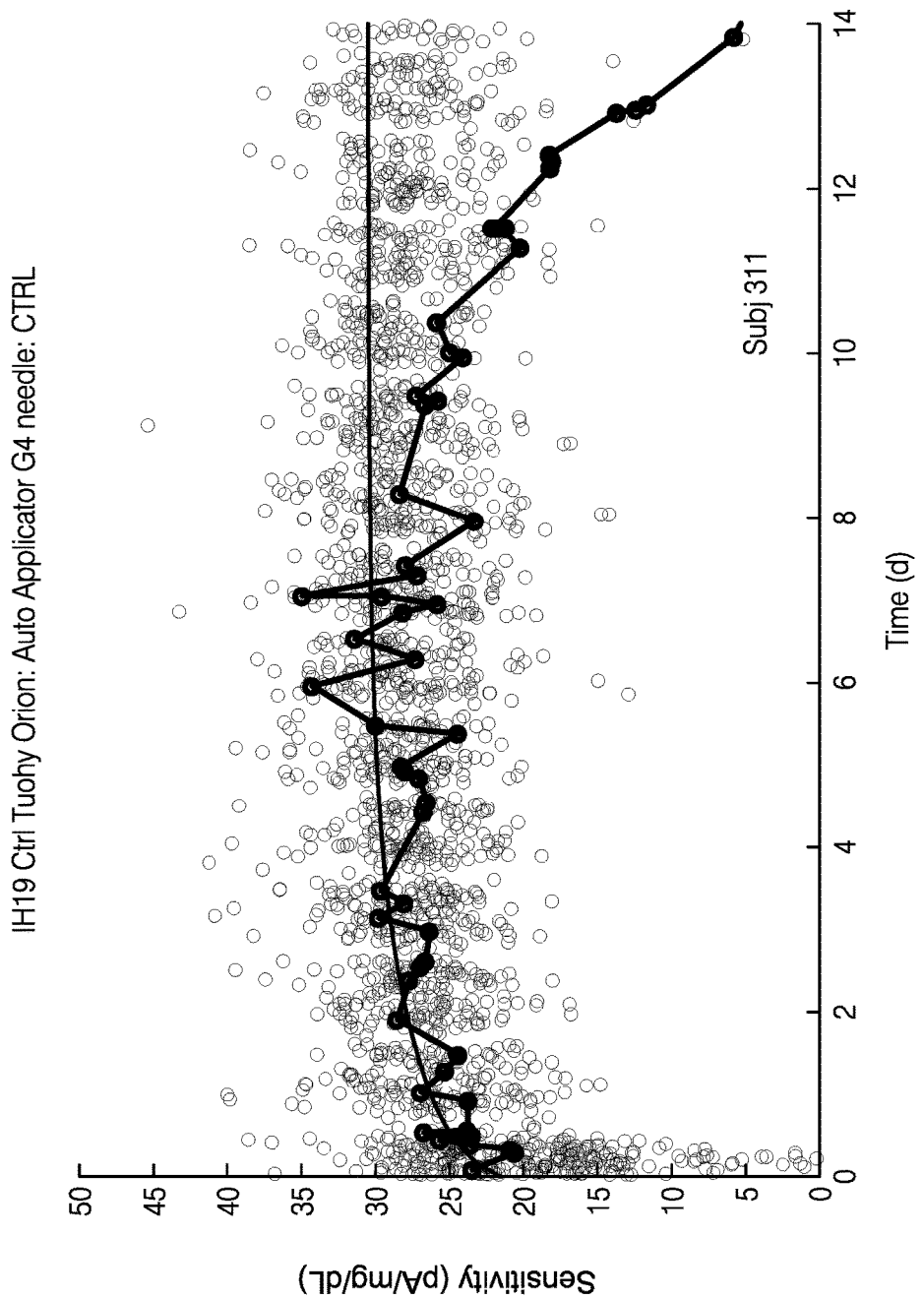
FIG. 23C is a chart showing sensitivity data over an extended sensor session, showing a characteristic drift along with a failure mode.

It is noted in this regard that generally sensors of a given type will be functional to meet required goals up to a certain tolerance. For example, 80% of sensors in a lot may work as desired (see FIG. 23B). The remaining 20% may on the other hand (see FIG. 23C) not follow an expected sensitivity curve. A large percentage, e.g., 75% of these remaining sensors, may follow a known failure mode, which results in their following a known alternate sensitivity curve, group of curves, or band of curves. By identifying which of these sensors are following the alternate sensitivity curve, and adjusting the calibrations of the sensors accordingly, the "failure" of the sensors may be remedied in large part. For example, if the failure mode is such that the 75% all have signal values that tend to decrease in the same way, upon determination of the failure mode, the "failure" may be remedied by adjusting the sensor readings "up". Such aspects may be particularly important as sensor sessions become longer and longer, e.g., go from 7 sessions to 14 day sessions. In the failure mode illustrated in FIG. 23C, a decrease in sensitivity began at about day eight. The ability to detect and remedy such failure modes is particularly important because, even as start of session sensor failure modes are becoming increasingly better characterized, end of session sensor failure modes, particularly with longer sessions, remain difficult to quantify.

In some implementations, considerations of glucose signal variability in combination with a slow moving average may be employed to differentiate glucose signal variations from sensor sensitivity fluctuations. For example, if the slow moving average decreases but the variability stays the same, or stays within a predefined range or band, then the cause of the slow moving average decrease is likely a sensitivity change. Alternatively, if the slow moving average decreases but the variability also decreases, then the cause of the decrease is likely a real and actual change in the glucose concentration.

Non-physiologically feasible changes, variations, errors, artifacts, and other signal behaviors may be the cause of various remedial actions by the system, and some of these have been mentioned above. For example, recalibrations may be performed, and the results may be propagated backwards to historical data. The user may be prompted to provide a fingerstick calibration. Part of a remedial action algorithm may be to determine whether to correct via recalibration or whether to prompt for a fingerstick or other calibration point. For example, if a signal is received that is outside physiologically feasible boundaries, then the user can be prompted for an additional calibration point, e.g., a fingerstick. Alternatively, the user may be prompted to provide additional information of other sorts, e.g., to enter data corresponding to recent exercise or meals, or other recent changes in user behavior. As a specific example, if a user's slow moving average of glucose concentration was 100 mg/dL for the first three days of a session, but on the fourth day it was suddenly 200, systems and methods according to present principles may prompt for a finger stick calibration. If the fourth day slow moving average was 105 mg/dL, then the system may scale or adjust the sensitivity accordingly, e.g., to bring the value back down to 100 mg/dL.

Where finger stick calibrations are performed, the use to which the fingerstick calibration data is put may vary depending on the use of the device. For example, if the device is being used adjunctively, i.e., non-therapeutically, which is the case for many type II users, if the fingerstick indicates a drift, it may still be possible to use the sensor if the drift is not substantial. In many cases, the techniques described here can be used to remedy the effect of the drift, and still allow the display of an accurate reading. If the device is being used non-adjunctively, e.g., for insulin using type I patients, then if the fingerstick indicates a drift, the remediation or adjustment, e.g., recalibration, may be made more aggressively, and if such cannot be made, or if an accurate sensor reading cannot be returned even upon recalibration, then an indication may be displayed to the user to cease use of the sensor.

Pattern analysis may be performed to determine if the change or variation is of a known type, e.g., is characteristic of known sensitivity changes. Pattern analysis may determine if changes or variations meet criteria, e.g., exceed certain thresholds, known for certain behaviors. As noted above a day's behavior may be employed in the determination of a slow moving average. If after analysis that day's data is determined by the system to be untrustworthy, another day's data may be used. Data may be displayed in ranges or bands, or with confidence intervals or other indications, rather than as a high precision numeral. Where slow moving averages are employed, the time constant of the slow moving filter may be adjusted so as to include or exclude more short term variations.

Figure 24:
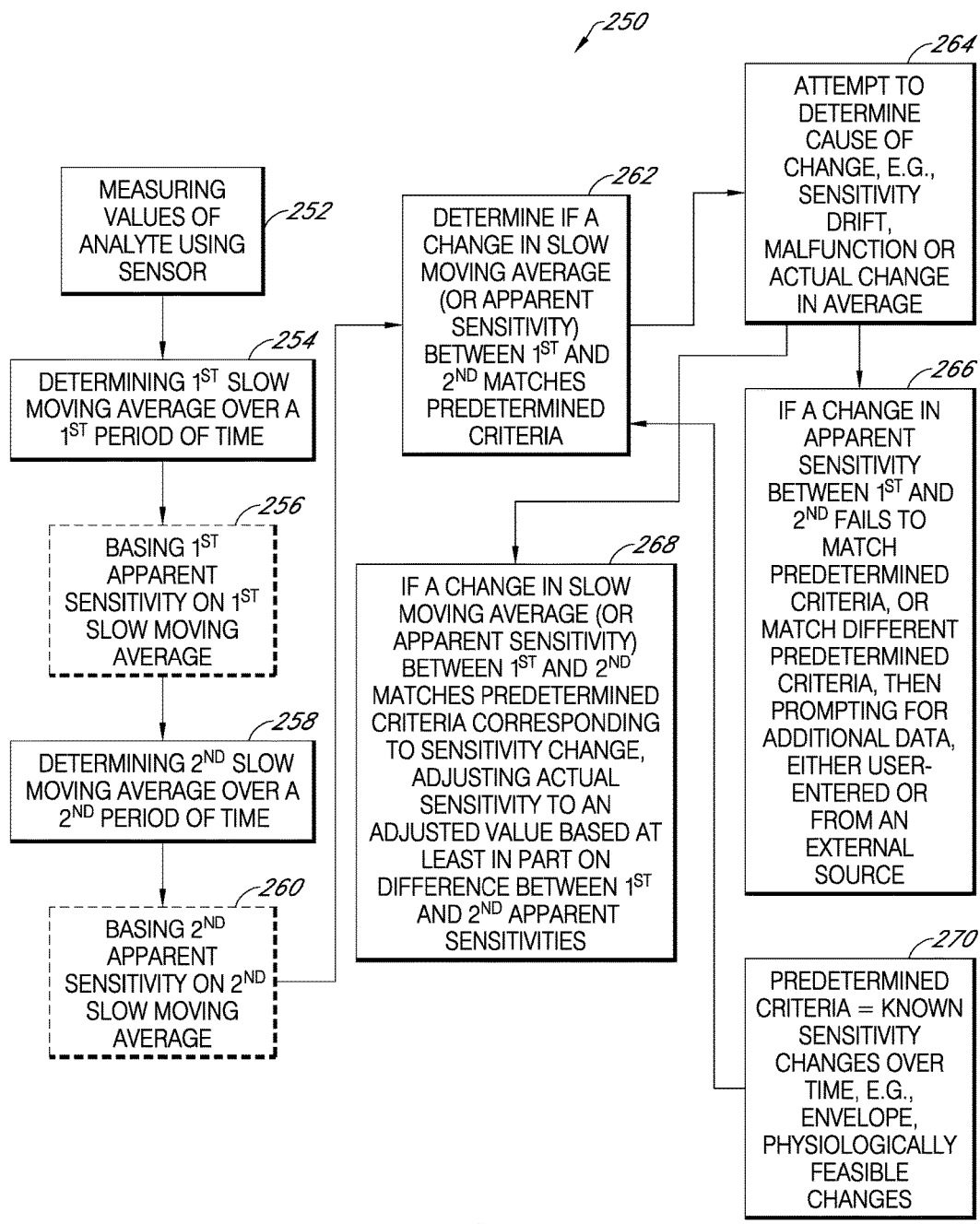
FIG. 24 is a flowchart illustrating another exemplary method according to present principles.

These aspects are summarized in the flowchart 250 of FIG. 24.

Referring first to FIG. 24, values of an analyte concentration may be measured by a sensor (step 252). Such values are generally measured as a current, e.g., as amps (picoamps), and equivalently as counts. A slow moving average may be defined by measuring the counts over a long period of time, such as over several hours, a half day, 24 hours, or 2-3 days. As sensors vary from unit to unit, the slow moving average will generally only be meaningful once an initial period, e.g., 24 hours, has passed. Thus, a next step is to determine a first slow moving average over a first period of time (step 254).

In one implementation, a value for initial use of a first apparent sensitivity may be posited via a seed value as in a manner described above. A first apparent sensitivity may then be determined based on the first slow moving average (step 256). In particular, if a first slow moving average is posited, then the first apparent sensitivity may be based on the relationship between the posited first slow moving average and the measured one.

Subsequently, a second slow moving average may be determined over a second period of time (step 258). And again, optionally, a second apparent sensitivity may be based thereon (step 260).

If the slow moving average, or apparent sensitivity, is seen to change between the first and second time periods, then remedial action may be called for. Thus, a next step is to determine if the change matches predetermined criteria (step 262). Predetermined criteria may include a number of elements (step 270), e.g. known sensitivity changes over time, an envelope of sensitivity profile curves, physiologically feasible changes, changes associated with errors such as pump malfunctions, or the like. For example, such a step may call for a determination as to whether a change matches criteria associated with a sensitivity drift, a malfunction, or an actual change in an average glucose concentration value (step 264). If consistent with drift, e.g., if it is determined that sensitivity has drifted by comparison with known sensitivity profile curves, then the correction may be made automatically. In any case, the sensitivity may be adjusted based at least in part on the difference between the two slow moving averages (step 268), as the same provides a quantitative indication of the degree of change or drift the sensor has undergone.

If the change is not consistent with drift, it may be determined if the change is consistent with other causes for which predetermined criteria exist. If the change is not consistent with known behaviors, e.g., matches no predetermined criteria, then the user may be prompted to enter information to explain the change (step 266), e.g., meal or exercise information, a finger stick calibration value, data from other external sources, or the like. In some cases, the user-entered data may be employed, along with the quantitative difference in slow moving average or sensitivity, in a recalibration routine, e.g., to determine a new or updated sensitivity.

Figure 25:
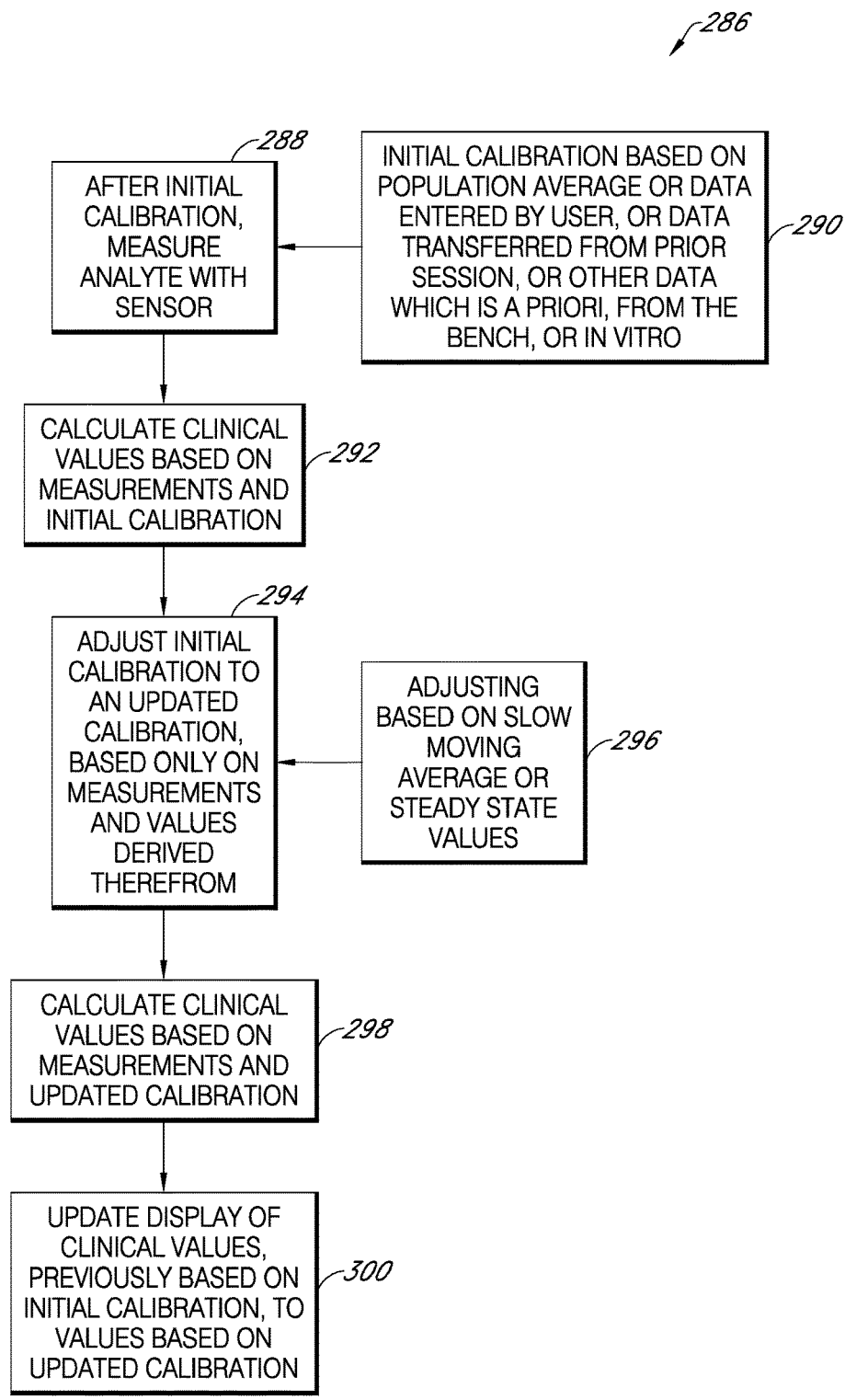
FIG. 25 is a flowchart illustrating another exemplary method according to present principles.

FIG. 25 illustrates another flowchart 286 of an exemplary method employing slow moving averages or steady state values. In a first step, after an initial calibration, analyte concentration values continue to be monitored with a sensor (step 288). The initial calibration may be based on a number of factors (step 290), including a population average, data from a prior session, bench data, in vitro data, or other a priori data.

Based on the measurements and on the initial value, a clinical value of the analyte concentration is calculated and/or displayed. An updated calibration may then be calculated, based only on the measurements, e.g., only on the signal from the sensor (step 294). The adjusting may be based on changes in the slow moving average, changes in steady state values, or other bases.

Subsequent to the updated calibration, clinical values may be calculated and/or recalculated based on the updated calibration (step 298), and the display may then be updated (step 300), including updating previously-displayed (historic) values to updated values based on the updated calibration.

Figure 26:
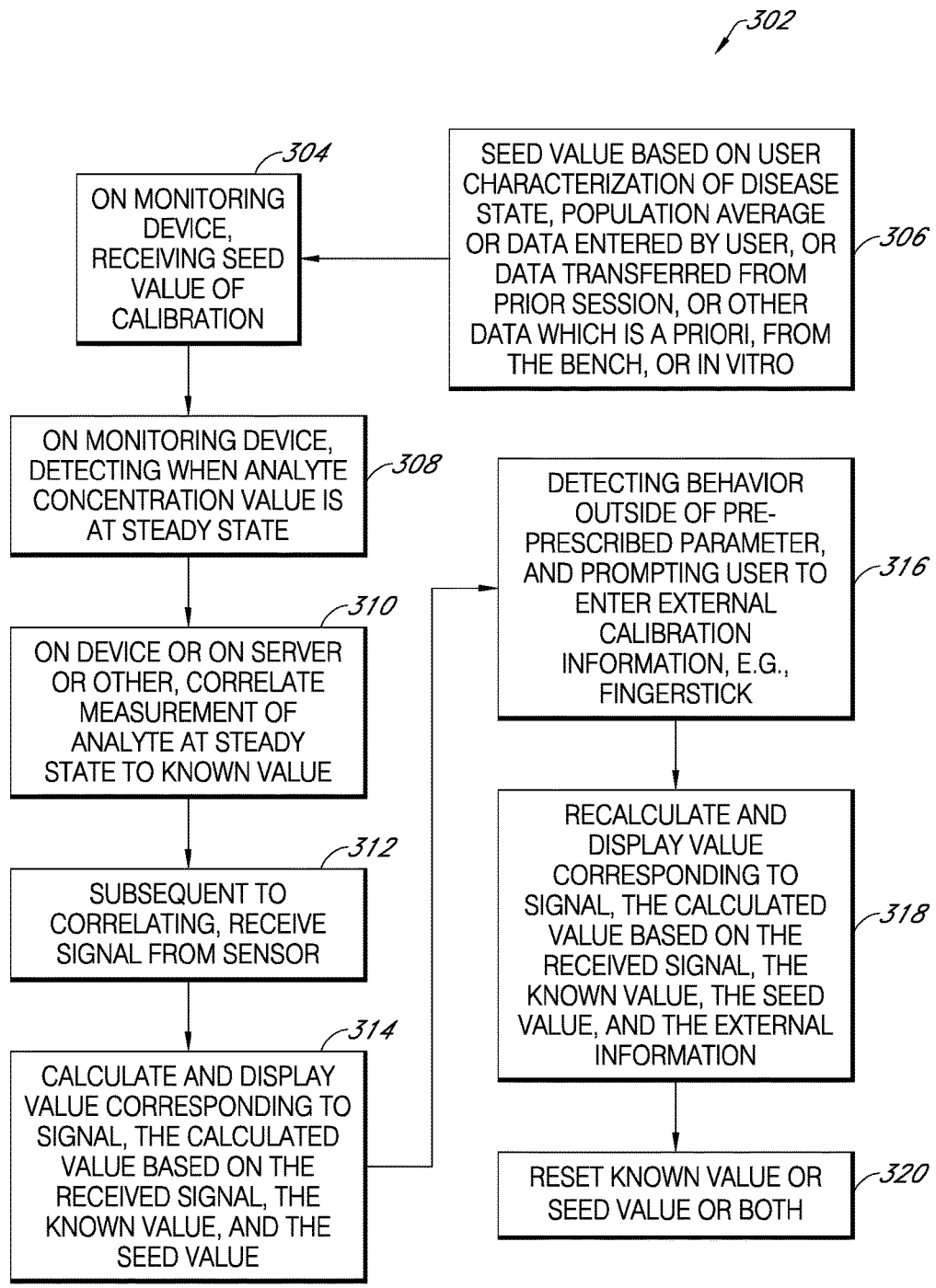
FIG. 26 is a flowchart illustrating another exemplary method according to present principles.
Figure 27:
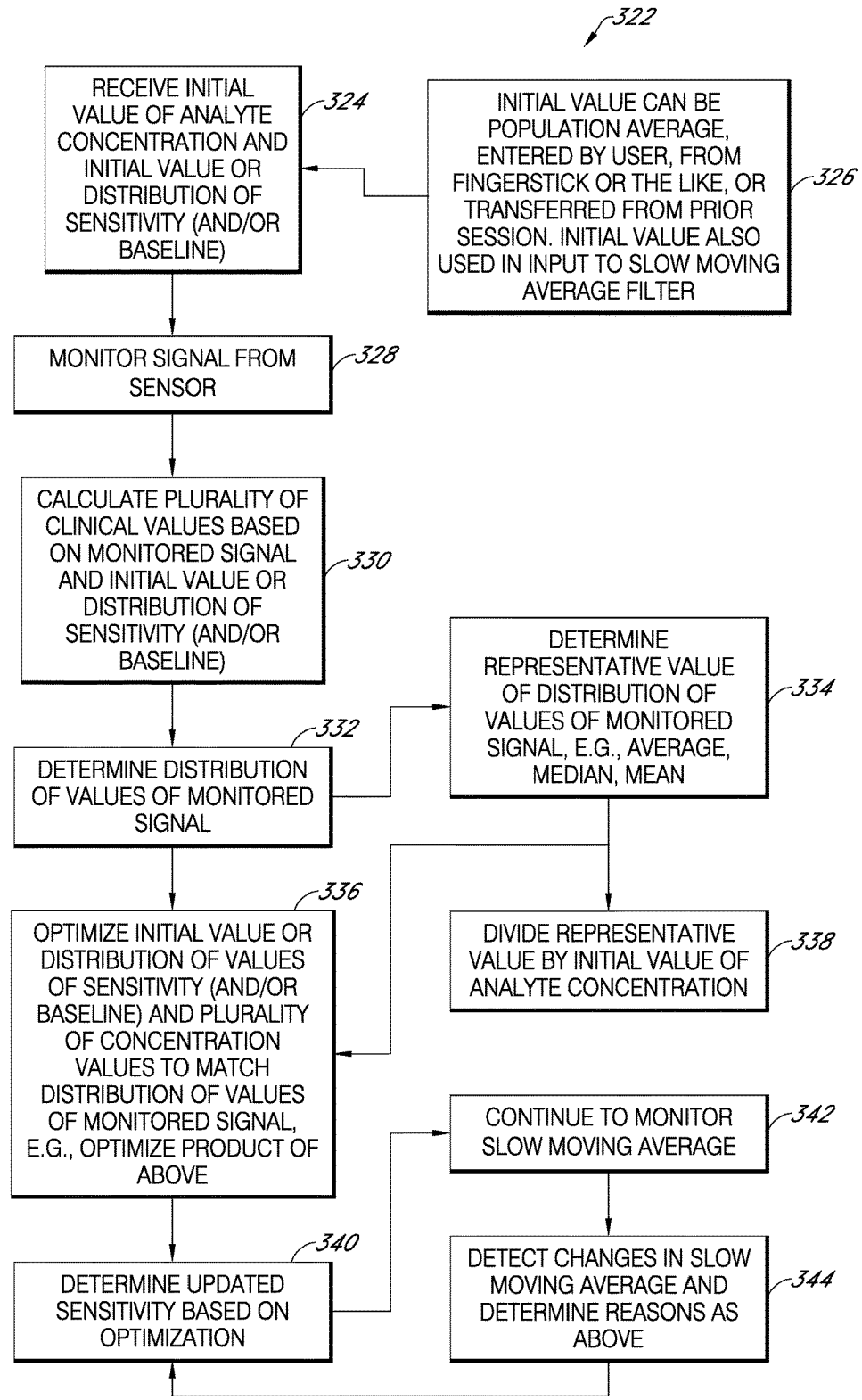
FIG. 27 is a flowchart illustrating another exemplary method according to present principles.

Yet another implementation of present principles is illustrated by the flowchart 302 of FIG. 26. A first step is, on a monitoring device, receiving a seed value of a calibration parameter (step 304), e.g., sensitivity. The seed value may be based on a number of factors (step 306), including a user self-characterization of a disease state, a population average, data from a prior session, bench data, in vitro data, or other a priori data.

The monitoring device then continues to receive sensor data, and may detect when an analyte concentration value is at a steady state (step 308). For example, this may occur when a set of received signals over a predetermined period of time is within a predetermined range or band of values. A correlation may then occur of the measured signal value, e.g., in current or counts, to the known or assumed steady state value (step 310).

Subsequent to the correlating step, the monitoring device continues to receive signals from the sensor (step 312). Clinical values of the analyte concentration are calculated and displayed based on the received signal, the known or assumed steady state value (even if the host is no longer at the steady state), and the seed value (step 314).

Behavior may be detected outside of pre-prescribed parameters, as described above in connection with FIG. 24, and users may be prompted to enter external data, e.g., a fingerstick calibration value (step 316). A recalibration may be computed, and/or a recalculation, followed by subsequent display (step 318), based on the received signal, the external data, and optionally the seed value. In some implementations the known steady state value, and/or the seed value, may be reset based on the calculations performed (step 320), and historic values recalculated and redisplayed.

FIGS. 27 to 33 illustrate a detailed method for determining calibration parameters, e.g., sensitivity and baseline, using a probabilistic approach. Certain aspects of probabilistic approaches are described in U.S. patent application Ser. No. 13/827,119, entitled "Advanced Calibration For Analyte Sensors", filed Mar. 14, 2013, owned by the assignee of the present application and herein incorporated by reference in its entirety. In this application incorporated by reference, which includes what is termed here a "signal based calibration algorithm", a priori calibration distribution information is modified with real time inputs and converted into a posteriori calibration distribution information, from which a calibrated data point is determined. In this way, calibration errors may be avoided where, e.g., regression results in errant sensitivity and/or baseline values due to improper assumptions about reference data. Other ways of determining calibration parameters such as sensitivity and baseline may also be employed, besides the ways described in the application incorporated by reference above. These ways include techniques enabling factory calibration usable during the life of a sensor session, and so on.

In FIGS. 27-33, distributions are again employed for calibration parameters such as sensitivity and baseline, but the same are optimized based on subsequently-known data, e.g., a sensor count distribution obtained over the first 24 hours of use of a sensor session. Referring first to the flowchart 322 of FIG. 27, a first step is to receive an initial value of an analyte concentration, from a sensor, and an initial value or distribution of sensitivity and optionally baseline (step 324). In some cases the effect of the baseline may be reduced to essentially zero, simplifying the calculations. The initial value of sensitivity can be from sources noted above (step 326), e.g., entered by a user, drawn from a population average, transferred from a prior session, or other sources of seed values. The initial value may also be used as part of a basis or in a calculation for a slow moving average filter. Where the initial values of sensitivity or baseline are distributions of such values, then the same may at least initially be developed from considerations of population statistics.

The analyte signal is then monitored from the sensor (step 328). A plurality of clinical values are then calculated and displayed, based on the monitored signal and on the initial value or distribution of sensitivity (step 330) or alternatively on an initial value of average glucose. For simplicity the baseline is assumed to be zero or negligible. The initial value or distribution of sensitivity is posited so that the user can be provided with displayed analyte concentration values, even if the same is less accurate during this initial time period than it will be subsequently, once additional data is gleaned.

A distribution of values of the monitored signal may then be determined (step 332). A representative value of the distribution of values of the monitored signal may be calculated (step 334), e.g., an average value, a median value, a mean value, and so on. As an initial sensitivity, the representative value may be divided by an initial value of analyte concentration (step 338), based on the initial posited sensitivity.

The initial value or distribution of values of sensitivity and/or the plurality of concentration values may then be optimized to match the distribution of values of the monitored signal (step 336). In more detail, the sensor count is the product of the sensitivity and the analyte concentration, and thus the concentration is equal to the sensor count divided by the sensitivity. The median sensor count may be determined, e.g., after 1 day's data is obtained, and a search may be performed that optimizes or provides the best fit for the distribution of the sensor count given the distributions or samples from a sensitivity parameter space and a baseline parameter space. For example, if a user's long term glucose values over a day ranged from 100 to 200, certain limits may be deduced on what the sensitivity and baseline can be. So the sensitivity and long term glucose values, within distributions, may be selected such that their product best optimizes the measured representative value of sensor counts. In addition, the sensitivity and long term glucose values may be selected (step 340) such that their values are 'most likely', where 'most likely' means that their values are closest to the centers of their respective distributions. A slow-moving average may be monitored (step 342), and changes in the same detected and analyzed as noted above (step 344).

Put another way, following the first day, data exists pertaining to a posited initial average glucose value, or sensitivity, and a distribution of sensor counts. From the distribution, a median sensor count may be obtained.

Sensor count $SC=f_{SC}(SC)$, which has a normal distribution.

The sensitivity equation has the form:

$y=mx+b$

If it is assumed $b=0$ and the equation is further specified to averages, then:

Median sensor count$=m*$average glucose value

And considering both sensor count and sensitivity as normal distributions:

$f_{SC}(SC)=m*GV$

Moreover, it is known that m is a slow moving function of time due to drift, and thus:

$f_{SC}(SC)=m(t)*GV$

And thus it is apparent that sensor count and glucose value are connected by a multiplicative "constant", which is actually a slow moving function of time.

The distribution of sensor count can also reveal aspects of the potential distribution of sensitivity, i.e., the potential initial sensitivity m, and in particular:

Average $GV=$(median $SC/m_{median}$)

And thus:

$m_{median}=$median $SC/$average $GV$

For example, if the median SC is 131,000 and the average GV is 131, then m is 1000 counts/(mg/dL). And the distribution of m may be checked to determine if this value is reasonable or unlikely. And a similar determination may be made for 'b', in cases where the same is non-negligible.

Figure 28:
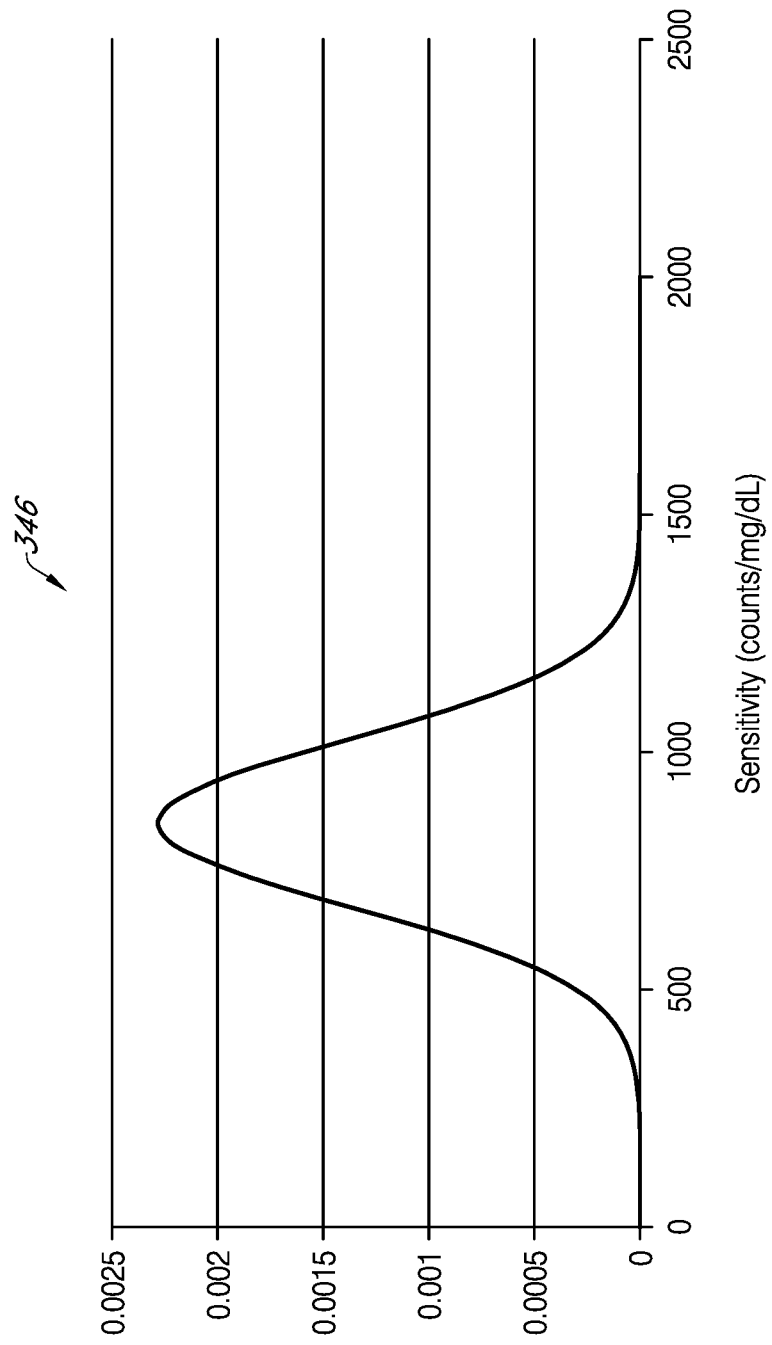
FIG. 28 is a graph illustrating a distribution of sensitivity.
Figure 29:
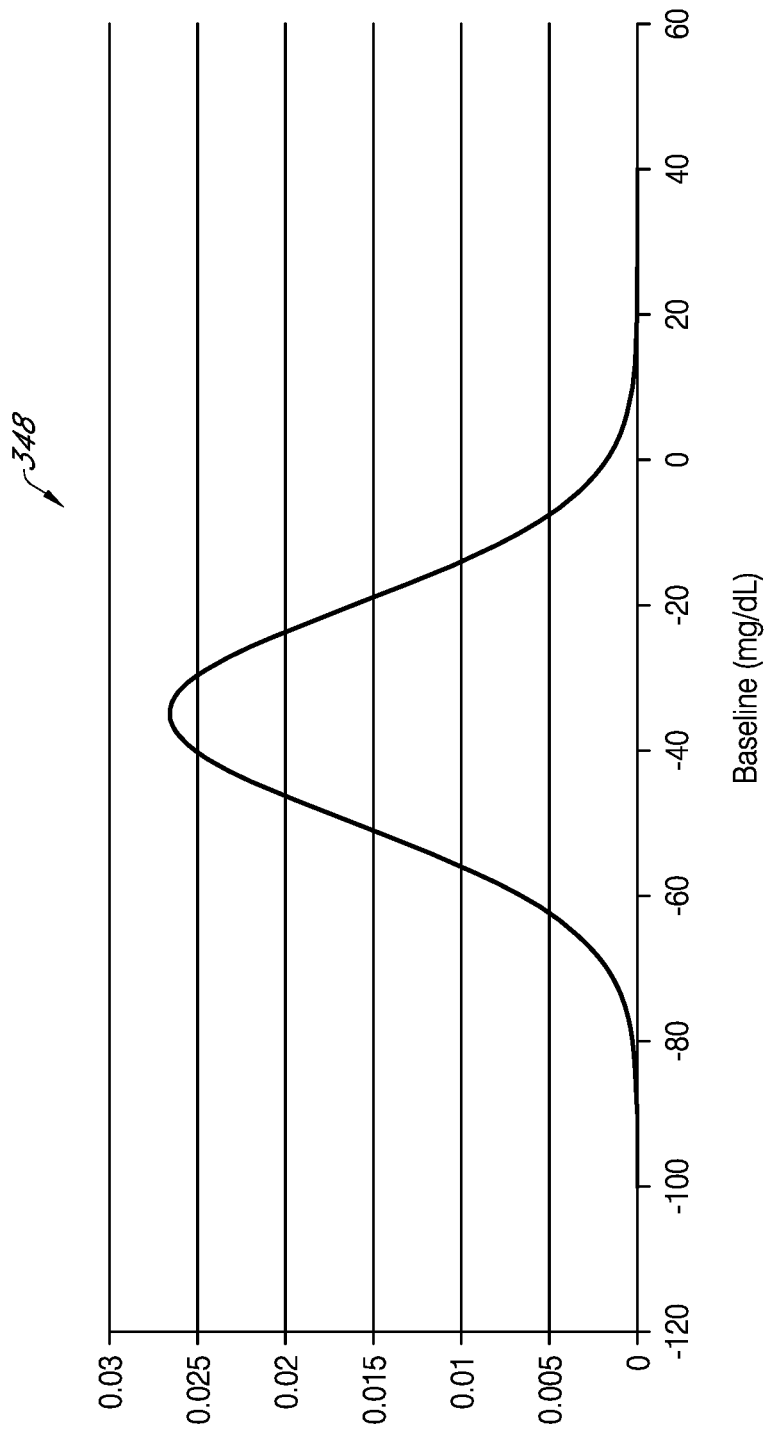
FIG. 29 is a graph illustrating a distribution of baseline.
Figure 30:
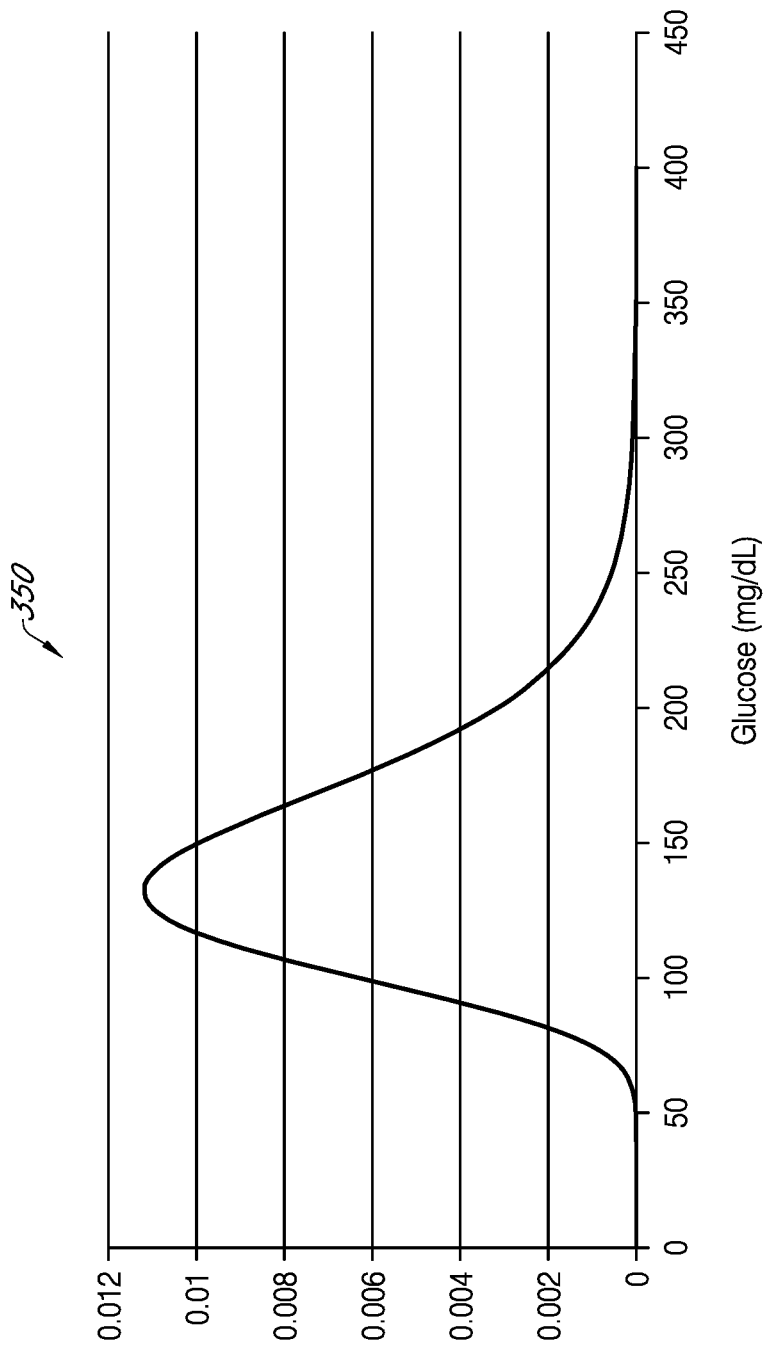
FIG. 30 is a graph illustrating a distribution of glucose values, e.g., long term glucose values.
Figure 31:
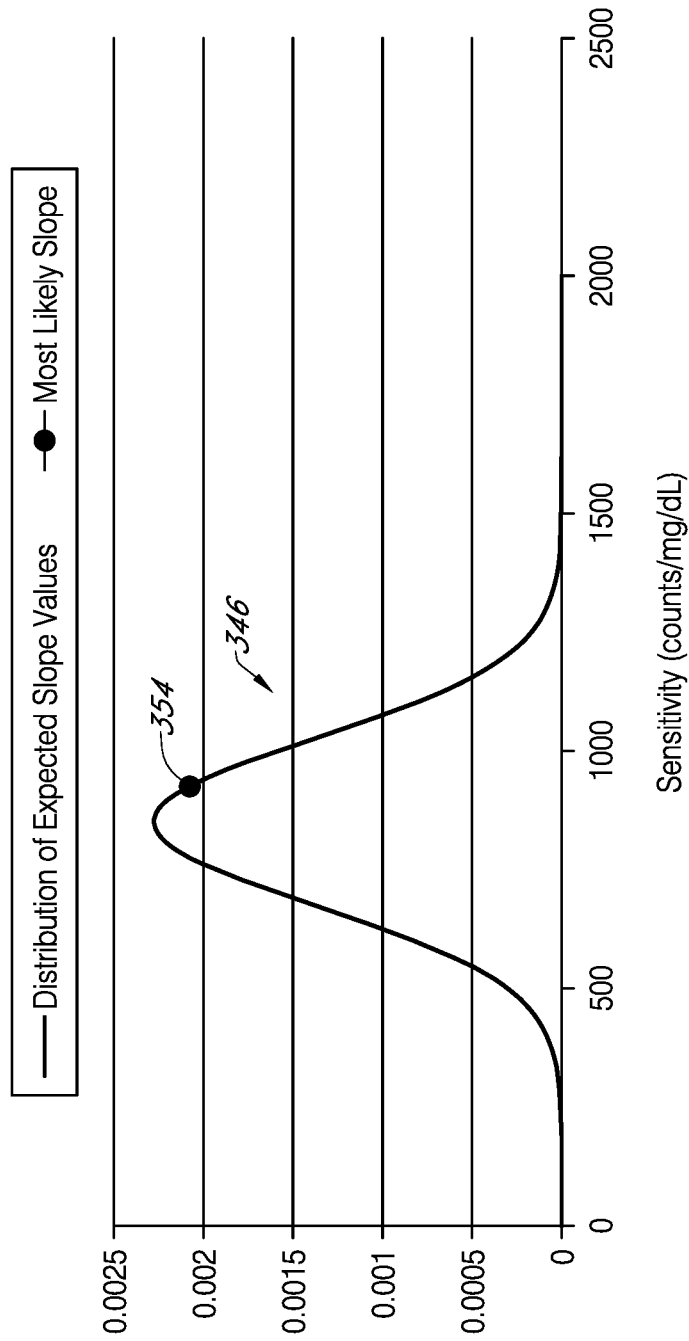
FIG. 31 is a graph illustrating a most likely sensitivity (slope) value, give exemplary parameters.
Figure 32:
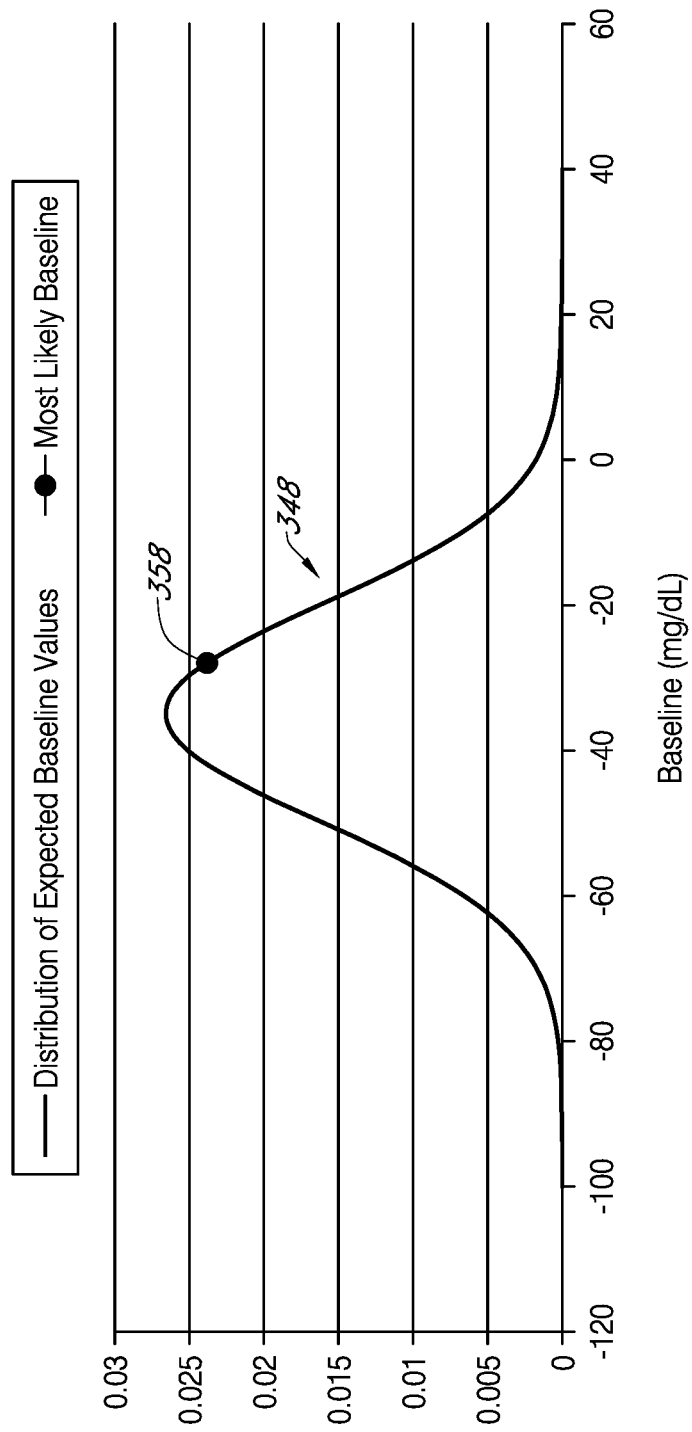
FIG. 32 is a graph illustrating a most likely baseline value, given exemplary parameters.
Figure 33:
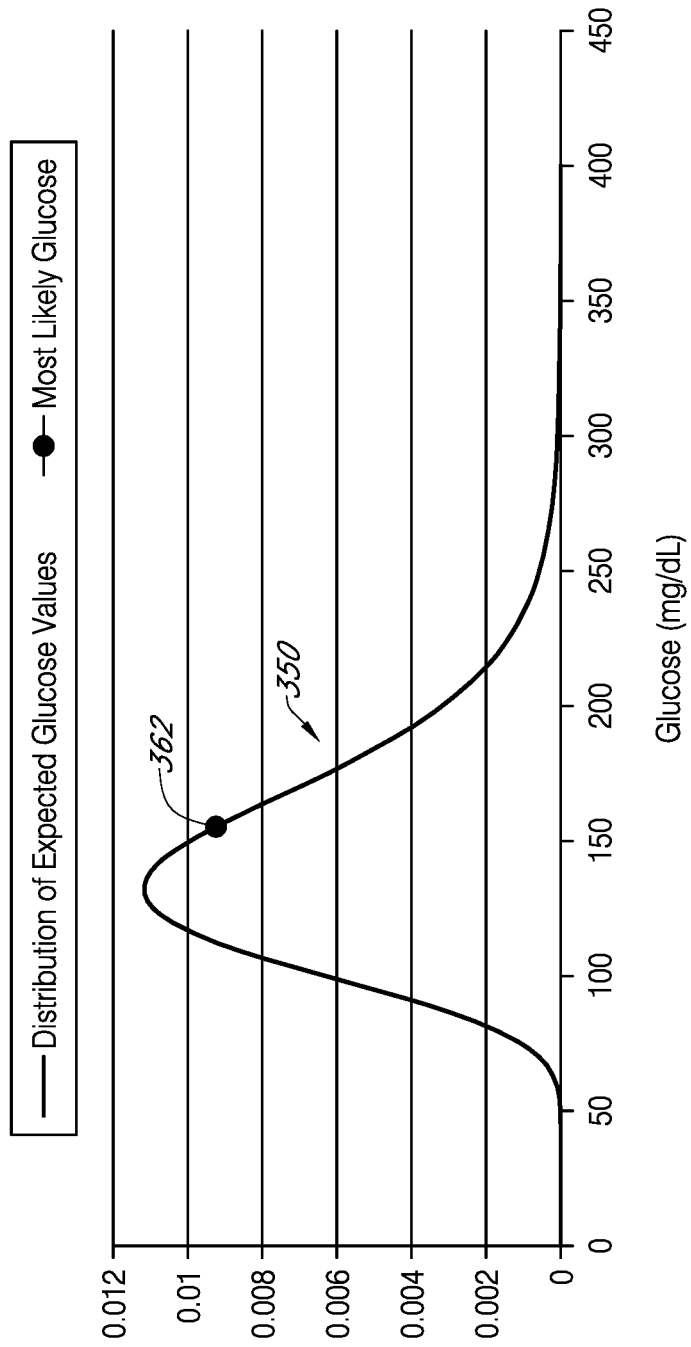
FIG. 33 is a graph illustrating a most likely glucose value, given exemplary parameters.

The representative value of the values of the monitored signal (sensor count) may be converted into an estimate of long term glucose:

Long term glucose=(long term sensor count)/(sampled sensitivity)−sampled baseline in mg/dL The graph 346 of FIG. 28 illustrates an exemplary distribution of sample sensitivities, the graph 348 from FIG. 29 illustrates an exemplary distribution of sample baselines, and the graph 350 of FIG. 30 illustrates an exemplary distribution of sampled long term glucose values. As one example, if a representative value of sensor count is 113,536, then given the constraints of the above-noted three distributions, the optimal slope is 890 counts/(mg/dL), the optimal estimate of long term glucose is 153.5685, and the optimal baseline is −26 mg/dL. These points are illustrated on the same set of graphs 346, 348, and 350, reproduced on FIGS. 31, 32, and 33, at points 354, 358, and 362, respectively.

In variations, distributions may be made more 'granular', such that different distributions may be provided for different demographic populations or groups. Other variations will also be understood.

As noted above, a slow moving average filter may be employed as part of drift quantification because the selectivity to glucose of an advanced sensor is high, therefore, the primary factor contributing to the change in a slow moving average is the sensitivity. To seed the slow moving average filter initially, the initial seed value of the average glucose concentration may be multiplied by the average sensitivity to get an initial number of counts. Subsequently:

$S_t=\alpha \text{Filter}_t\alpha * S_{t-1}+(1-\alpha)STX_t\text{sensor}_t$

After a period of time, e.g., 1 day, enough data may be received such that the same can be revised to the actual average and the same employed for determinations of drift. The above steps may then be repeated, to determine subsequent best combinations of slope, baseline, and glucose in the manner described above will give the best raw count to match up with the estimate of raw count determined from, e.g., day 1 data.

Distributions can be modified in some implementations according to measured data as more is obtained. In this way a better calibration may be obtained. At the beginning only posited distributions were employed. Subsequently, actual measured data is available and may be employed. Filters may be reseeded with a median or other representative sensor counts, and the distributions will generally converge to actual measured data. If fingerstick data is available, the same may be employed for even faster convergence.

The seeding or re-seeding may be performed in a number of ways, and tailored to enable a more rapid convergence of drift curves based on filter seed parameters. For example, initial seed values for the filter can be based on the expected signal level as estimated from an expected average glucose level and sensor sensitivity. Initial seed values for glucose can also be based on subject demographics such as age of user and their duration of diabetes. Initial seed values can also be based on data such as medical record information or laboratory tests such as fasting glucose levels, glycated hemoglobin (A1C) tests, current diabetes treatments (e.g. oral medications, basal insulin use, or intensive insulin therapy) or downloaded self-monitored blood glucose values.

In another implementation, an initial seed value can first be used to start a filter running in the forward direction. After a representative set of sensor readings has been collected, e.g., after 24 hours of sensor readings, then a second filter can be run in the reverse direction. When a representative set of sensor readings is available, then the forward or reverse filters can be seeded with a typical signal value, such as the median sensor reading, or the filters can be seeded with typical signal values that are adjusted for the expected drift, such as starting the forward filter with 0.9*median and the reverse filter with 1.1*median. These techniques have the benefit that when two or more filters are used, such as a forward filter and a reverse filter, then their seed values can be further optimized to minimize the difference between the two filter outputs. For example, one exemplary way is to minimize the mean squared error between the two filter outputs.

In the system and method according to present principles as described above, redefining the seed values from day to day helps minimize the mean absolute error in the signal domain. In one implementation, each day, using a rough estimate of signal trajectory, e.g., from day 1, a smooth trend of a noisy filter output can create the trajectory for drift for day 2. Drift rate estimates can be compared from two or more different methodologies, and a difference or error between the two can feed into an algorithm such as a signal based calibration algorithm such as is disclosed in the patent application incorporated by reference above (Ser. No. 13/827,119), that determines distributions of sensitivities, particularly with regard to certainty intervals. Also in this way, signal features can be extracted, including features corresponding to noise, level, drift model, power, energy, and so on. In this way, it can be determined whether the drift correction is on a proper trajectory. For example, if the drift slope is considerably different than what a factory calibration model would suggest, e.g., by more than a predetermined threshold percentage, then the user can be prompted for feedback or can be prompted to provide a finger stick calibrations.

In some implementations, smoothing filters may be employed to compensate for signal drift in real time. In one case, a double exponential smoothing filter is used. Such a filter may assume a multiplicative damped trend with no seasonality; however, one may assume an additive or multiplicative seasonality to improve performance. The double exponential filter operates to recover the underlying change in sensor signal, i.e., drift, as a function of time. There are three primary underlying equations that govern the double exponential smoothing filter:

$$\hat{y}_{t+h|t} = l_t * b_t^{\phi}$$
$$l_t = \alpha * y_t + (1-\alpha) * l_{t-1} * b_{t-1}^{\phi}$$
$$b_t = \beta * \frac{l_t}{l_{t-1}} + (1-\beta) * b_{t-1}^{\phi}$$

A table for the parameters in the equations can be seen below in Table I:

TABLE I

| | |
|---|---|
| $\phi$ | The dampening parameter (between 0 & 1) that dampens the trend. This makes the trend approach a constant sometime in the future. |
| $l_t$ | An estimate of the level of the series at time t |
| $b_t$ | An estimate of the growth rate (in relative terms) of the series at time t |
| $\alpha$ | The smoothing parameter for the level, $0 \le \alpha \le 1$ |
| $\beta$ | The smoothing parameter for the trend, $0 \le \beta \le 1$ |
| $y_t$ | Input into the time series, e.g., a filtered sensor count |
| $\hat{y}_{t+h|t}$ | The h-step ahead forecast of the sensor count |

In the above equations, and in this setting, alpha and beta may be considered to be small. Alpha is small because it is desirable to have the filter not be influenced by glucose excursions. Beta is small because the underlying trend being recovered is slow moving in nature. One set of exemplary results were generated using the following parameters (Table II (assumes a five-minute sampling rate)):

TABLE II

| | |
|---|---|
| $\alpha$ | 0.0006 |
| $\beta$ | 0.001 |
| $\phi$ | 0.1 |
| $b_{t-1}$ | 1.01 |
| $l_{t-1}$ | m * Mean Glucose |

In the above equations, slope can be the algorithm-calculated initial sensitivity or a value determined from another methodology, or using any of the methods for determining sensitivity values noted above. Mean glucose in the above equation can be the mean of historic glucose values from prior sessions or, e.g., based on A1C values reported by users. In one implementation, data were generated using the initial sensitivity estimated by the algorithm using a 2 hour calibration and self-reported A1C numbers from a cohort of test subjects.

A drift correction curve was estimated using the following equation:

$$Drift_t = \frac{\hat{y}_t - \hat{y}_0}{\hat{y}_0}$$

The sensor signal was then drift corrected using the following equation:

$$DriftCorrectedSensor_t = \frac{Sensor_t}{1 + Drift_t}$$

Glucose values were then calculated using the following equation:

$$Glucose_t = \frac{DriftCorrectedSensor_t - baseline}{slope}$$

In the above equation, slope is that estimated by the algorithm at the initial calibration and the baseline is the slope multiplied by 1 mg/dL.

Figure 34:
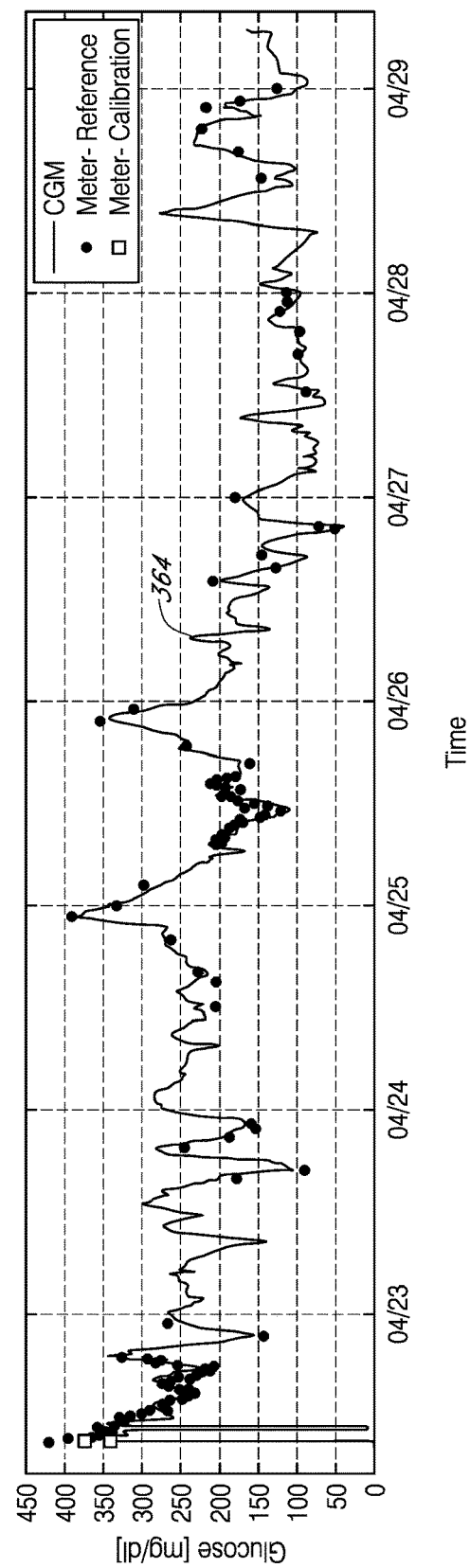
FIGS. 34 and 35 illustrate exemplary glucose traces.
Figure 35:
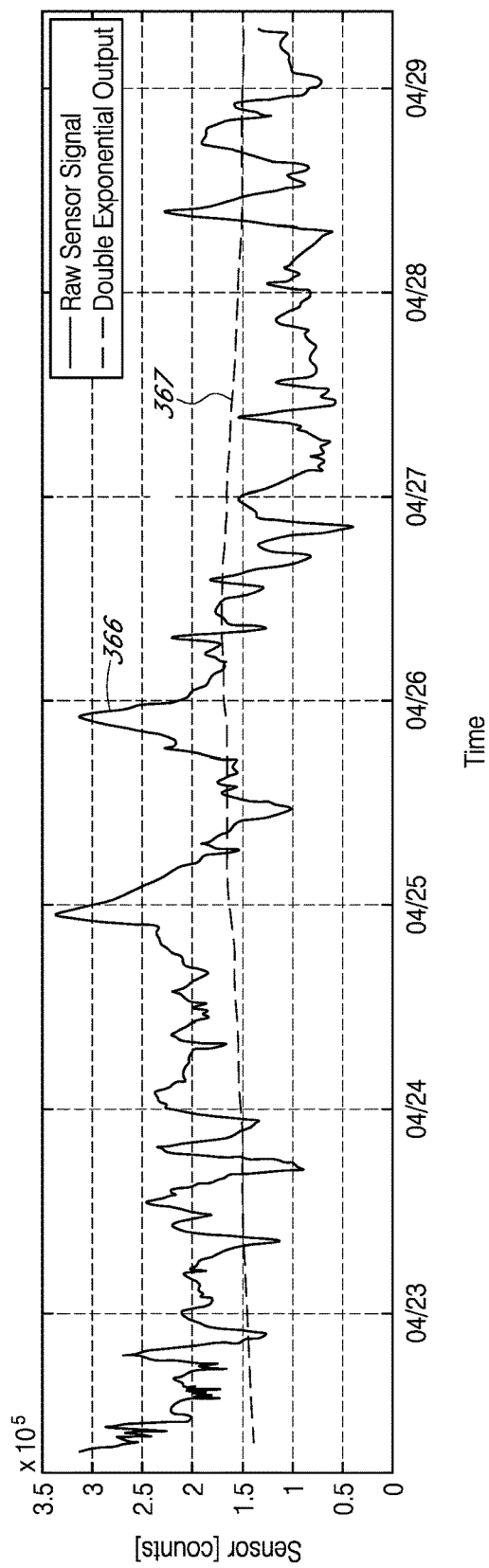

To show the efficacy of the double exponential filter, FIGS. 34 and 35 illustrate exemplary glucose traces. FIG. 34 shows a CGM trace 364 along with reference and calibration values. FIG. 35 illustrates a raw sensor signal 366 along with an output 367 from a double exponential filter. In this case the sensor was calibrated once using two start-up values entered by the user.

Figure 36:
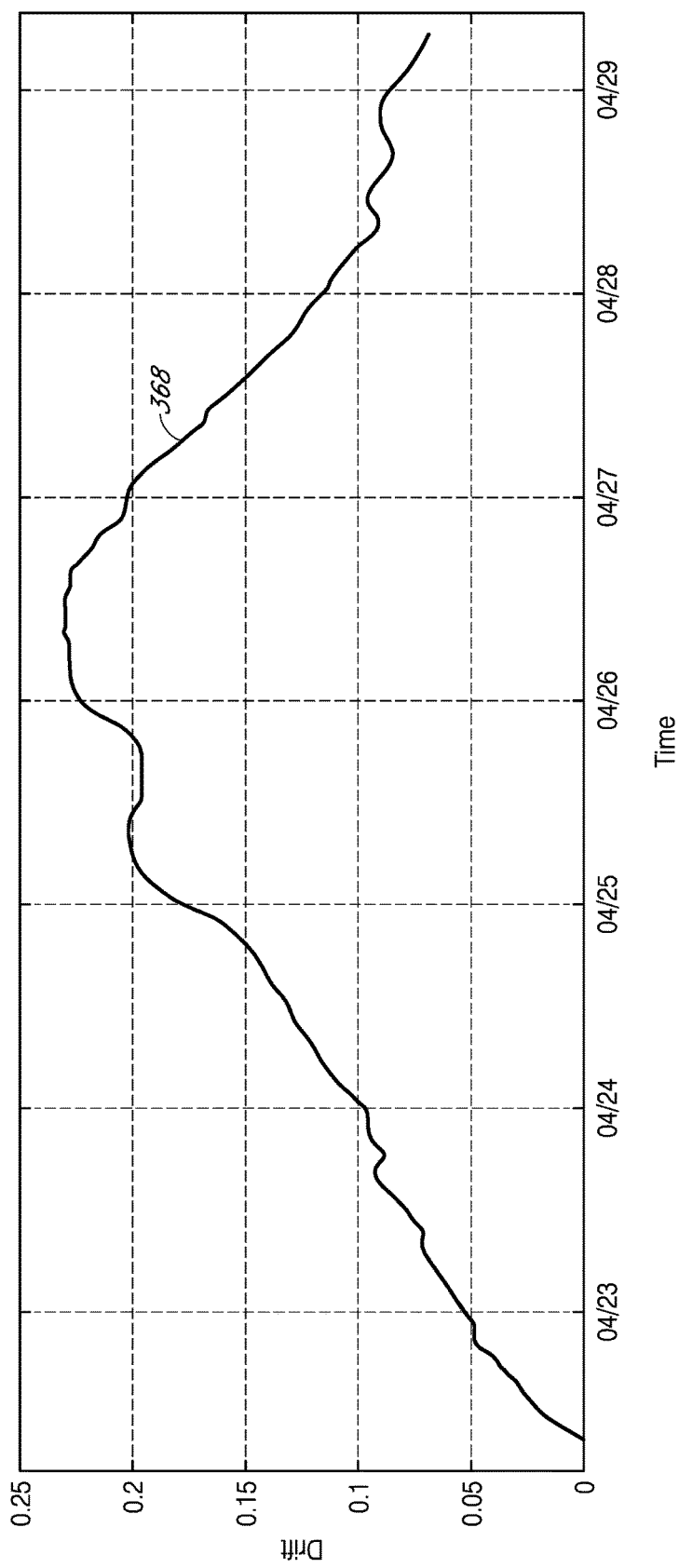
FIG. 36 illustrates an estimated drift curve for the sensor employed in determining FIGS. 34 and 35.

The estimated drift curve for the above sensor can be seen by the curve 368 in FIG. 36. As may be seen, the drift curve is readily seen in both upward and downward directions, and knowledge of the drift as detected and quantified by the double exponential filter allows for correction of the drift. One advantage of this implementation is that there is no need to rely on any known curve shapes to correct for drift.

Figure 37:
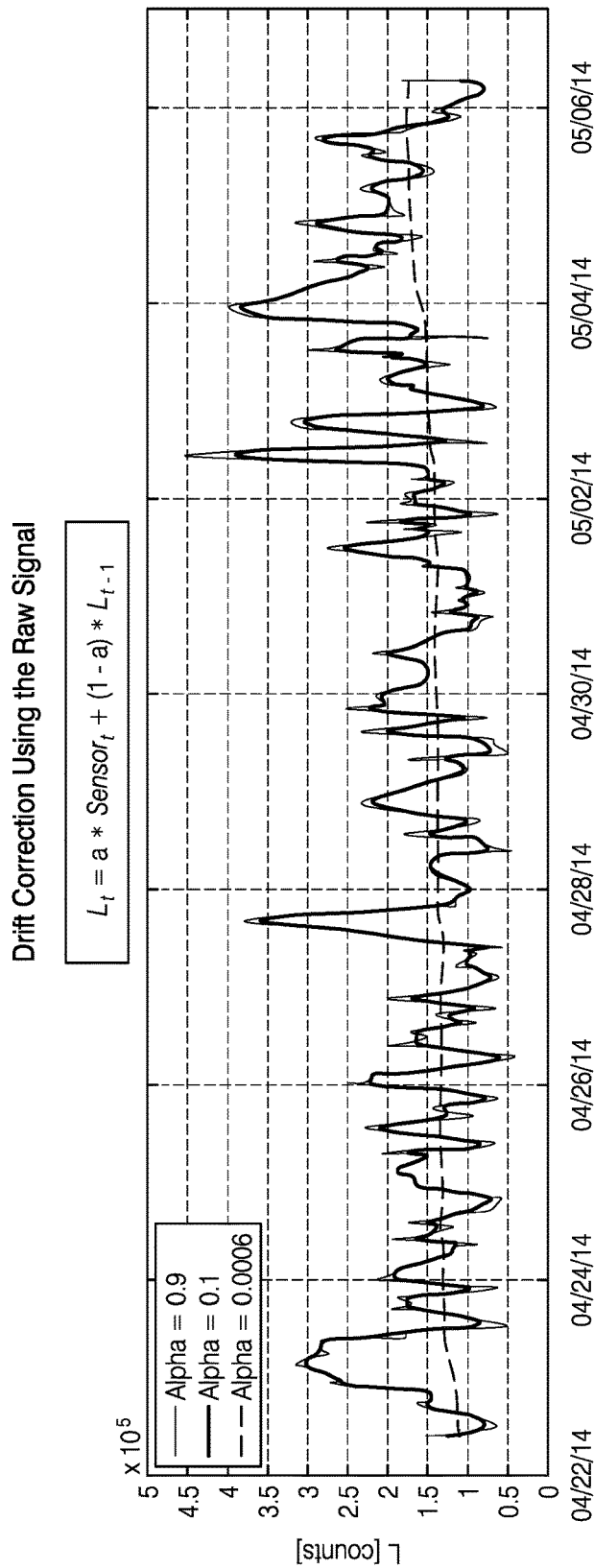
FIGS. 37-39 are additional charts in which drift correction according to the above principles is illustrated.
Figure 38A:
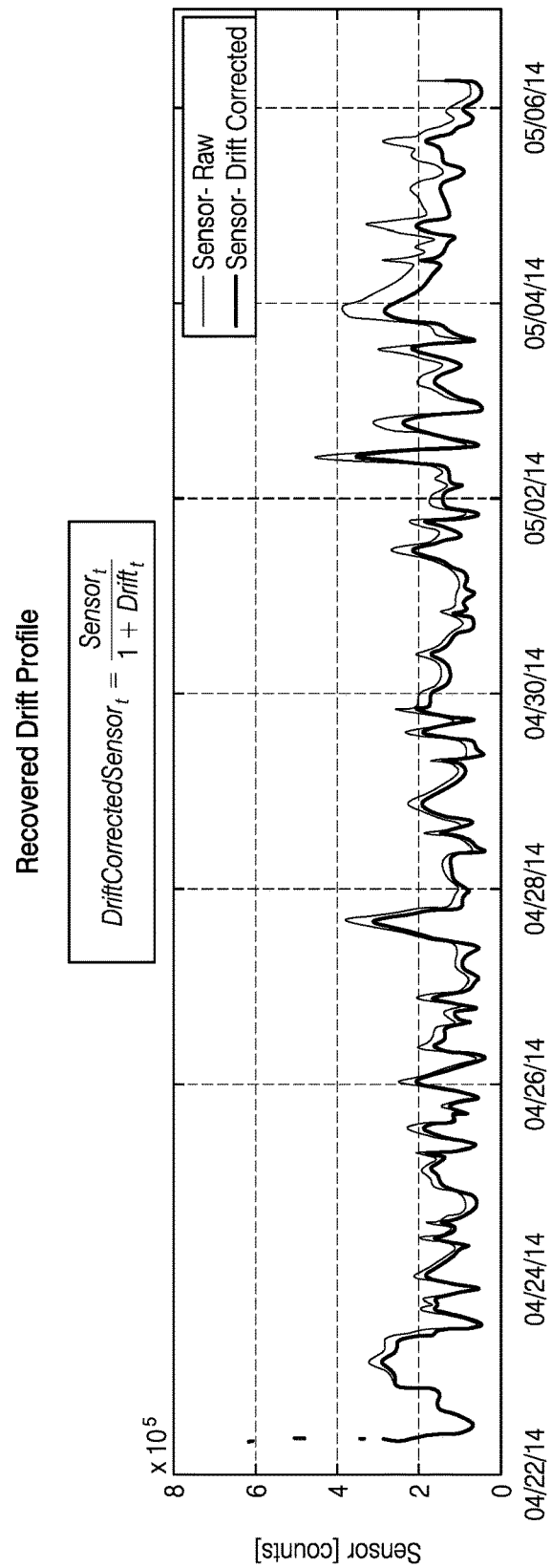
Figure 38B:
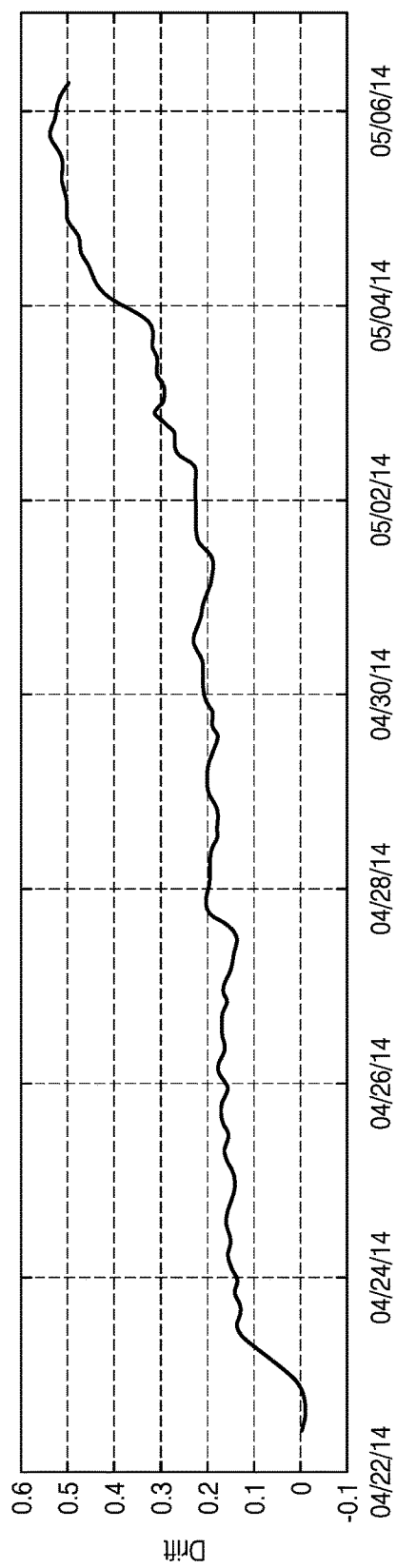
Figure 39:
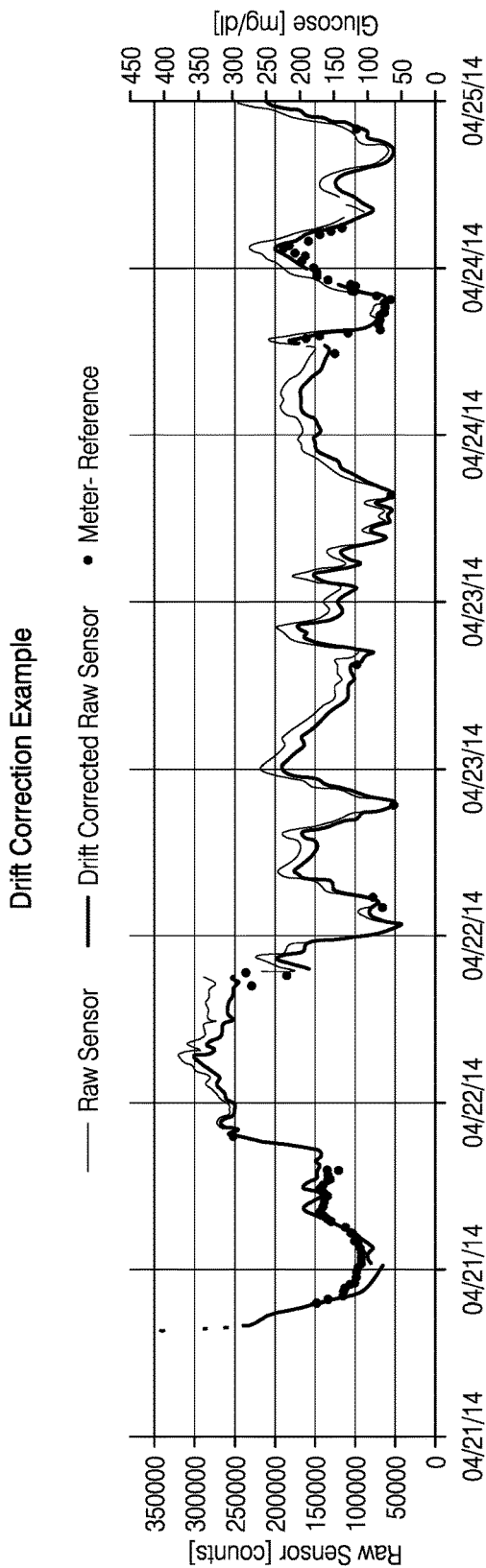

FIGS. 37-39 are additional charts in which drift correction according to the above principles is illustrated.

Besides the use of double exponential filters, other filters may also be used. For example, Kalman filters may be employed that include process noise, also known as model noise, and measurement noise estimates. Gaussian filters may also be used, as well as classical Butterworth low-pass filters, moving median filters, moving average filters, and so on, so long as the filter helps uncover an underlying trend. Filter banks or series of filters may be used, that combine multiple filters so as to obtain an average or combined trend in an underlying signal. Where multiple filters are used, different types of filters may be employed within a single bank, and filter settings may vary from filter to filter. By the use of multiple filters, signal correction may be improved at the ends of subsequent time periods, e.g., at the end of a second day's worth of data, at the end of a third day's worth of data, and so on. Without wishing to be bound by theory, it is assumed in the use of these filters that a variability in an average glucose measurement from day to day is insignificant compared to the change in slope or underlying signal change.

In other variations, signals may be pretreated before drift estimation filtering to remove data gaps and outliers. In addition, calibrations may be automatically updated in such a way as to reduce the occurrence of unexpected jumps in CGM readings. Such ways include making changes when the signal is stable, e.g., altering calibration settings in the middle of the night, or slowly blending the calibration changes into a current setting over a period of time, e.g., an hour or more.

Other useful techniques that may be employed with filtering include various decomposition techniques. For example, empirical mode decomposition can be employed to break down the signal into a series of intrinsic mode functions over time. Other time and frequency based decompositions may be employed, including Fourier transforms and wavelet transforms.

Figure 40:
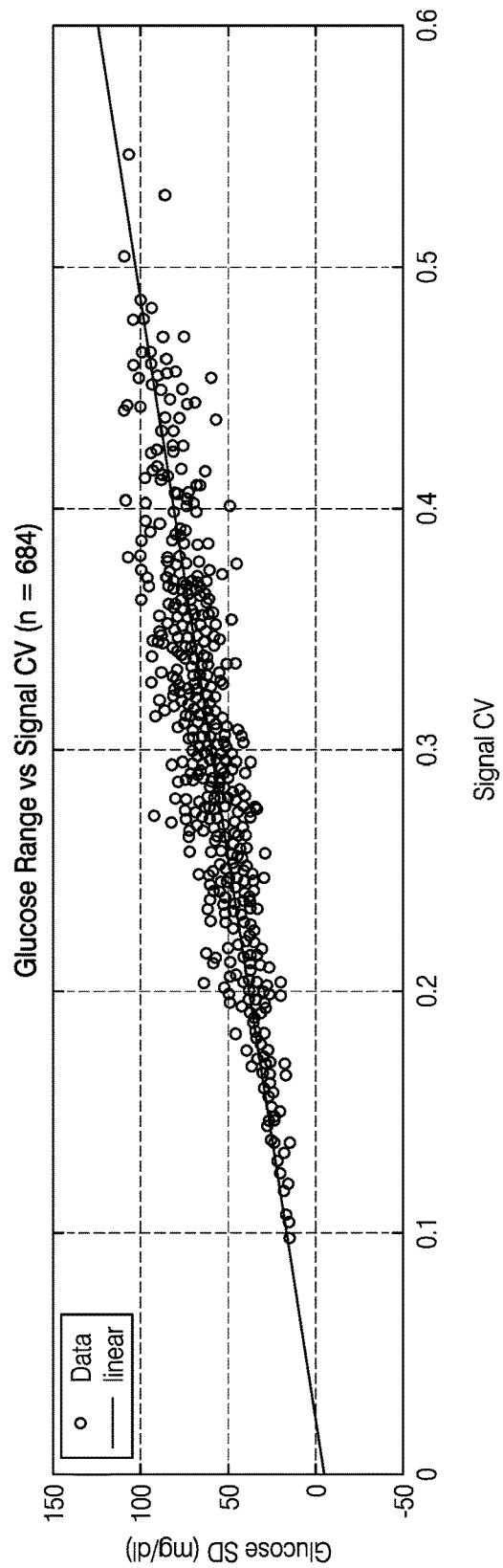
FIG. 40 illustrates a measured relationship between a signal coefficient of variation and a glucose concentration value standard deviation.

In another variation, other signal-based parameters can be determined and used in calibrations. For example, referring to FIG. 40, it may be seen that the coefficient of variation (CV) of the sensor signal has a strong correlation with the glucose variation in the signal, e.g., with the glucose standard deviation. Thus, in determining calibration parameters, this correlation may be employed to select calibration parameters that satisfy the signal CV—glucose standard deviation error model.

In more detail, a priori information as has been described can be employed in factory calibration and such includes information obtained prior to a particular calibration. For example, such information includes that from previous calibrations, that obtained prior to sensor insertion, and so on. Calibration information includes information useful in calibrating a continuous glucose sensor, such as, but not limited to: sensitivity (m), change in sensitivity (dm/dt), and other signal and time derivative aspects as have been described above. Also important a priori information includes distribution information, such as ranges, distribution functions, and distribution parameters including mean and standard deviation.

With respect in particular to the standard deviation of distributions of glucose values, the same may advantageously be employed, e.g., in determining boundaries of likely glucose values and probable combinations of sensitivity and baseline. Standard deviations may also be employed in determinations of levels of certainty from a priori calibration distribution information, such as where the same is a feedback of a posteriori calibration distribution information from a prior calibration (where the level of tightness or looseness of the distribution is quantified by the standard deviation). In the same way, levels of certainty may be determined from a posteriori calibration distribution information, e.g., based on the level of tightness or looseness of distribution, which again may be quantified by the standard deviation.

Figure 41:
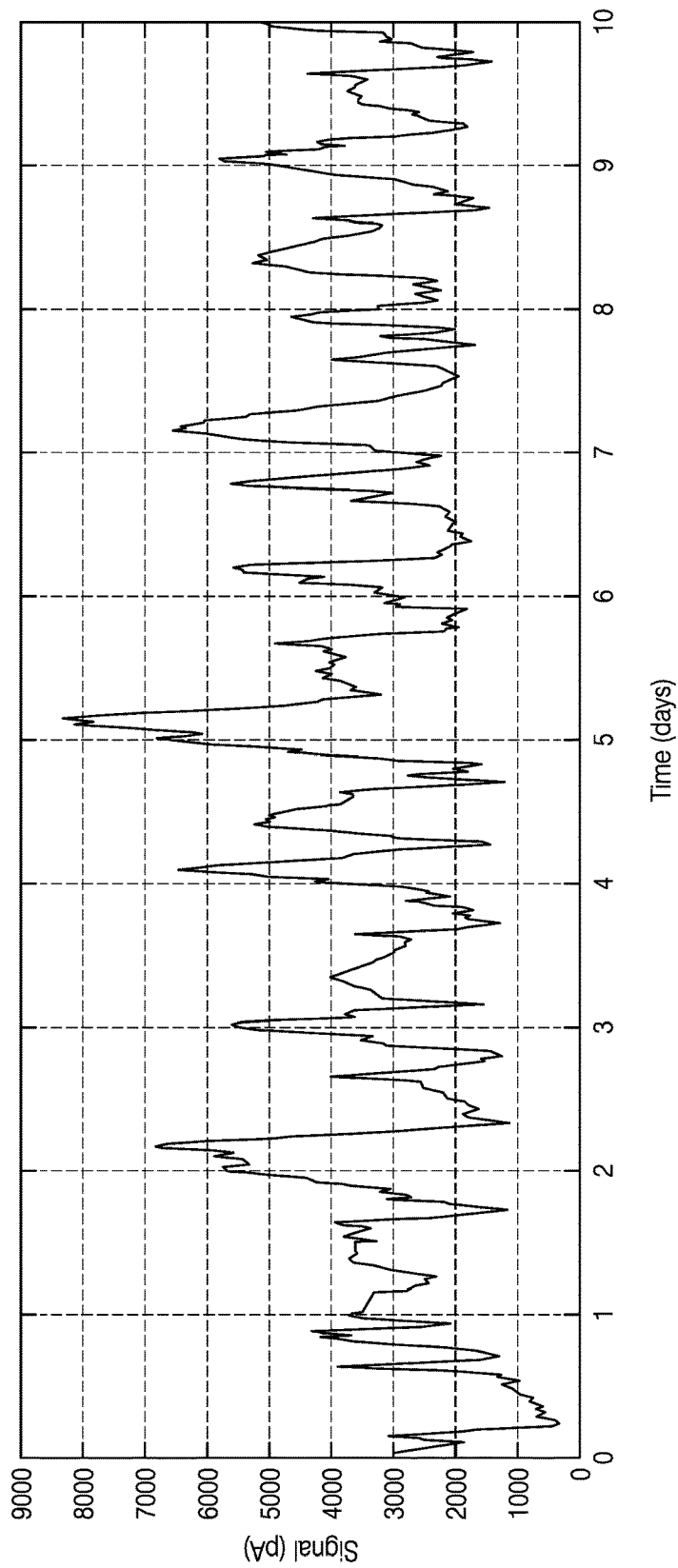
FIG. 41 illustrates a measured glucose concentration signal over a period of time.

As a particular example, FIG. 41 shows a glucose signal over the course of 10 days. From this a signal standard deviation and a signal mean may be computed. A signal coefficient of variation may then be determined by:

Signal CV=Signal Standard Deviation/Signal Mean

In the case of FIG. 41, the signal CV was calculated to be 0.4230.

Figure 42:
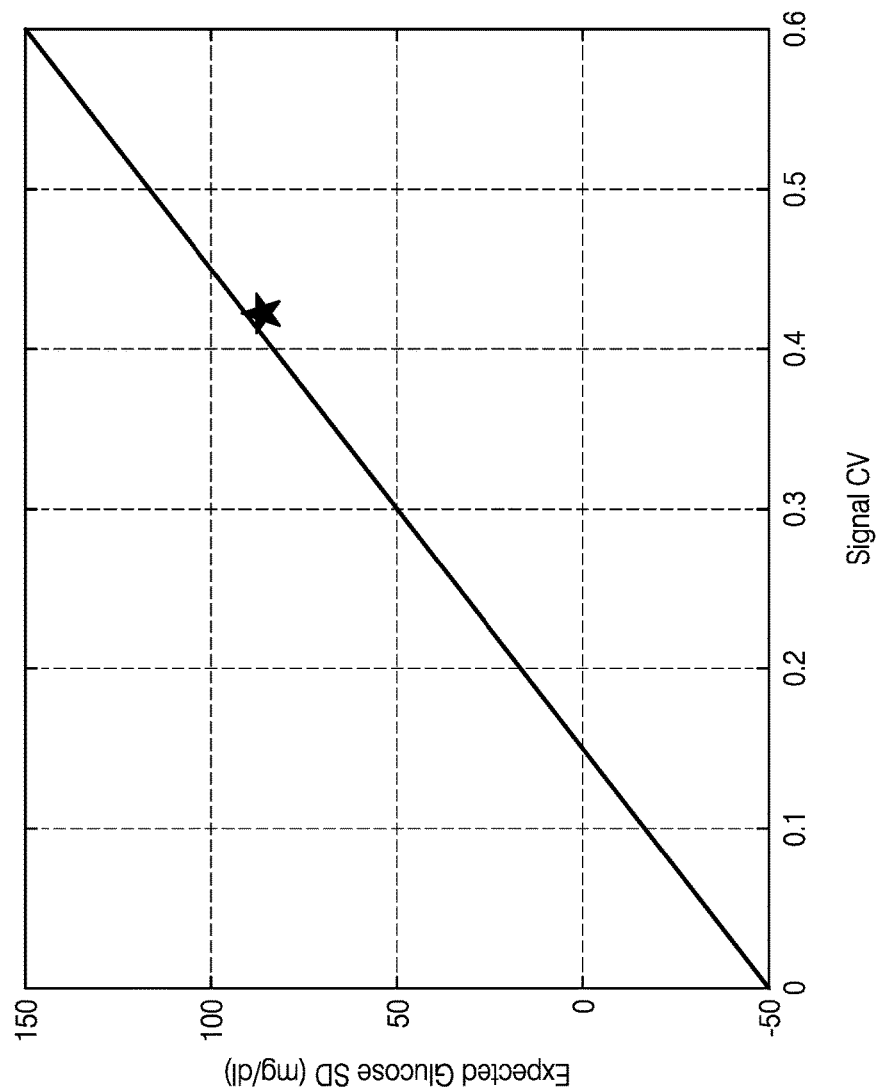
FIG. 42 illustrates a linear relationship between signal coefficient of variation and glucose concentration standard deviation, with an exemplary value marked.

If a relationship has been determined between the signal CV and the glucose standard deviation, e.g., see the line in FIG. 42, then the calculated signal CV determined above may be used to determine an expected glucose standard deviation, which may then be used in the calculations noted above, as well as other calculations. For example, an error model may be built using this correlation and the error model used in calibrations within the above incorporated by reference U.S. patent application Ser. No. 13/827,119.

Figure 43:
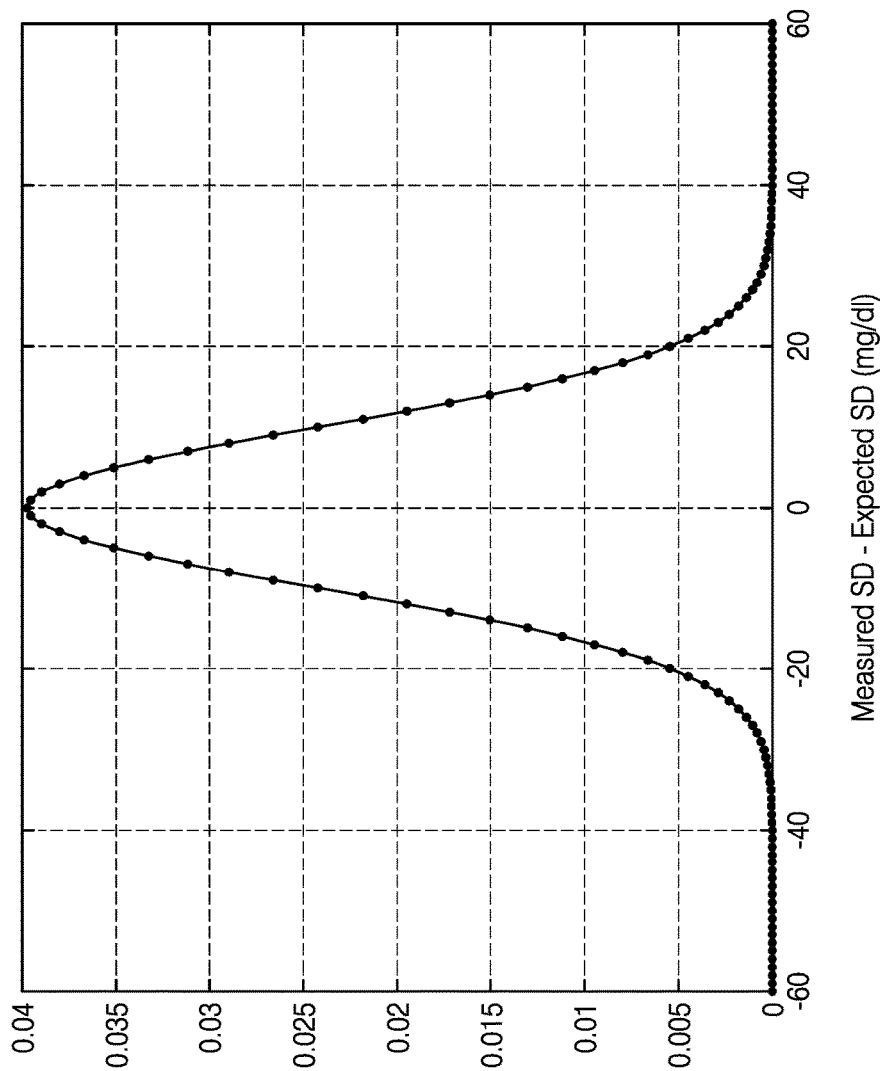
FIG. 43 illustrates a distribution of a difference between a measured standard deviation and an expected standard deviation.

FIG. 43 shows an exemplary distribution of the difference between the measured standard deviation and the expected standard deviation.

Figure 44:
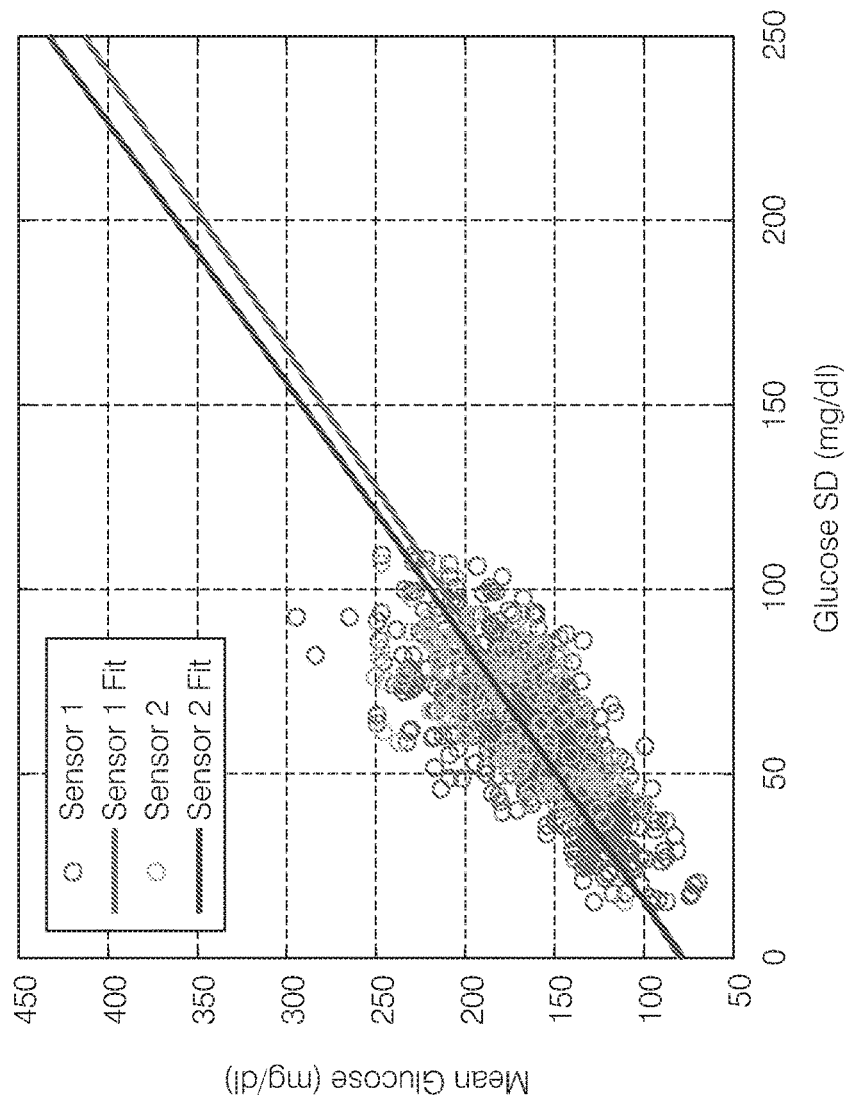
FIG. 44 shows a relationship between mean glucose and glucose standard deviation.
Figure 45:
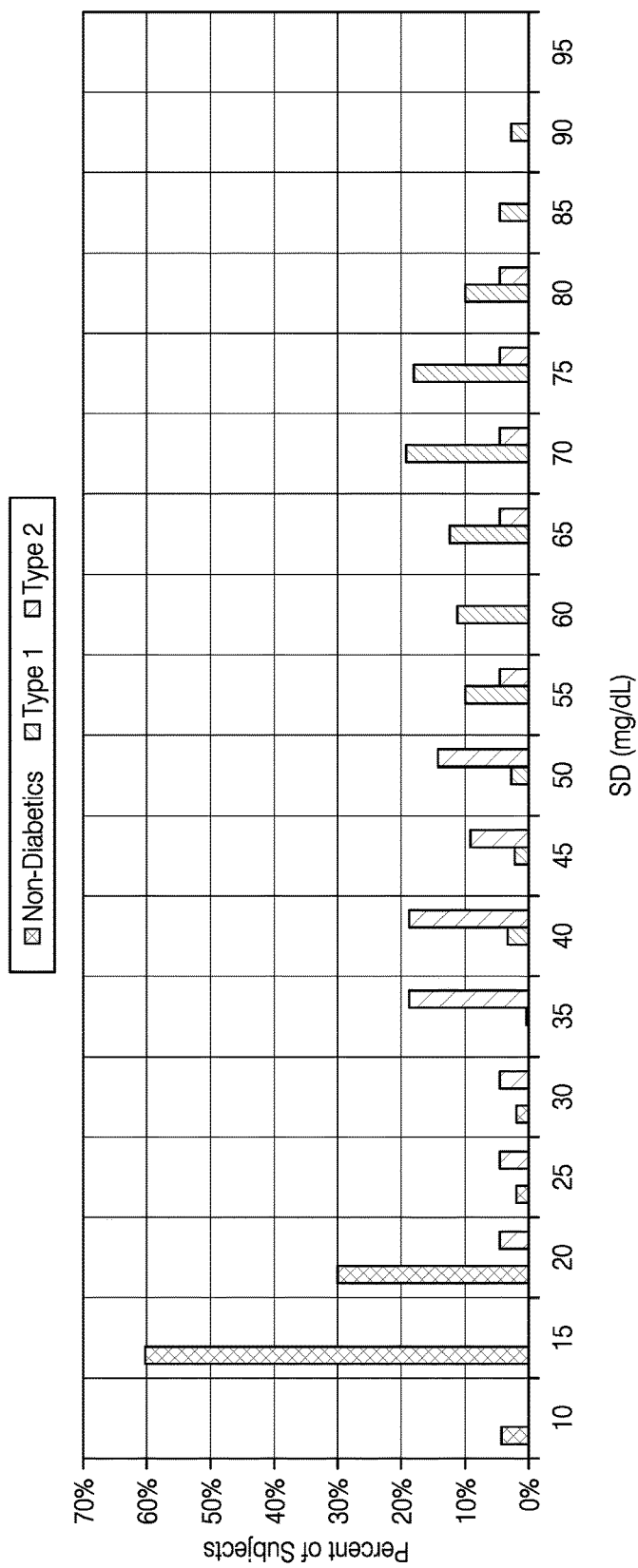
FIG. 45 shows distinctions between glucose standard deviations as between patient populations, i.e., non-diabetics, type I diabetics, and type II diabetics.

Other relationships may also be employed. For example, referring to FIG. 44, a relationship may be seen between the mean glucose value and the glucose standard deviation. In particular, it can be seen that users with a higher standard deviation tend to have a higher mean glucose. This relationship may be employed in determining, setting, inferring, or otherwise choosing calibration values. As another example, and referring to FIG. 45, another useful indicator is patient type. In particular, FIG. 45 illustrates a clear distinction in glucose standard deviation between non-diabetics, type I diabetics, and type II diabetics. Accordingly, based on the type of patient, the model chosen for a patient population could be changed based on the type of population, e.g. the standard deviation could be tightened on the CV error model, the mean could be shifted, and so on.

Figure 46:
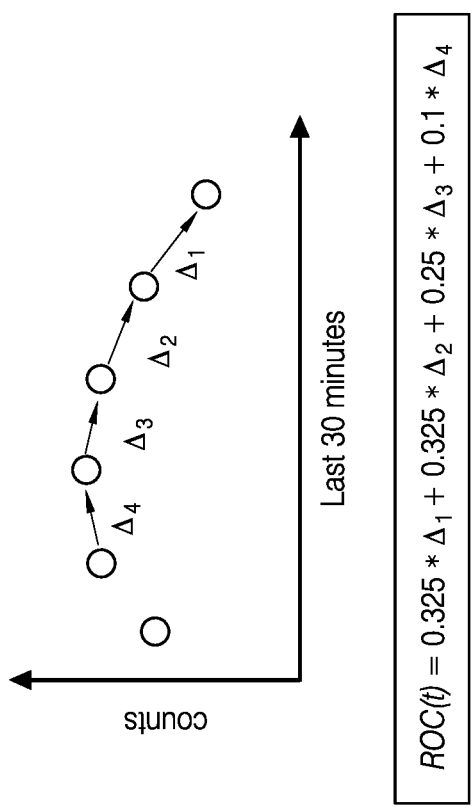
FIG. 46 show data points separated by time lags, wherein Δ represents the individual rate of change between two adjacent points.

As noted above, the system may adjust the data for a time lag (e.g., to remove a time lag induced by real-time filtering) from data for a previous time period and may display a graphical representation of the time lag adjusted data for that time period (e.g., trend graph). The system may also compensate for a time lag. For example, FIG. 46 show data points separated by time lags, wherein Δ represents the individual rate of change between two adjacent points. By use of an equation such as the below or similar, such time lags may be compensated for:

Glucose(*t*)=[DriftCorrectedSensor(*t*)+5*ROC(*t*)]/*m−b* (mg/dL)

For example, if the current point is in light noise, all filtered sensor counts may be employed.

Example

Figure 47:
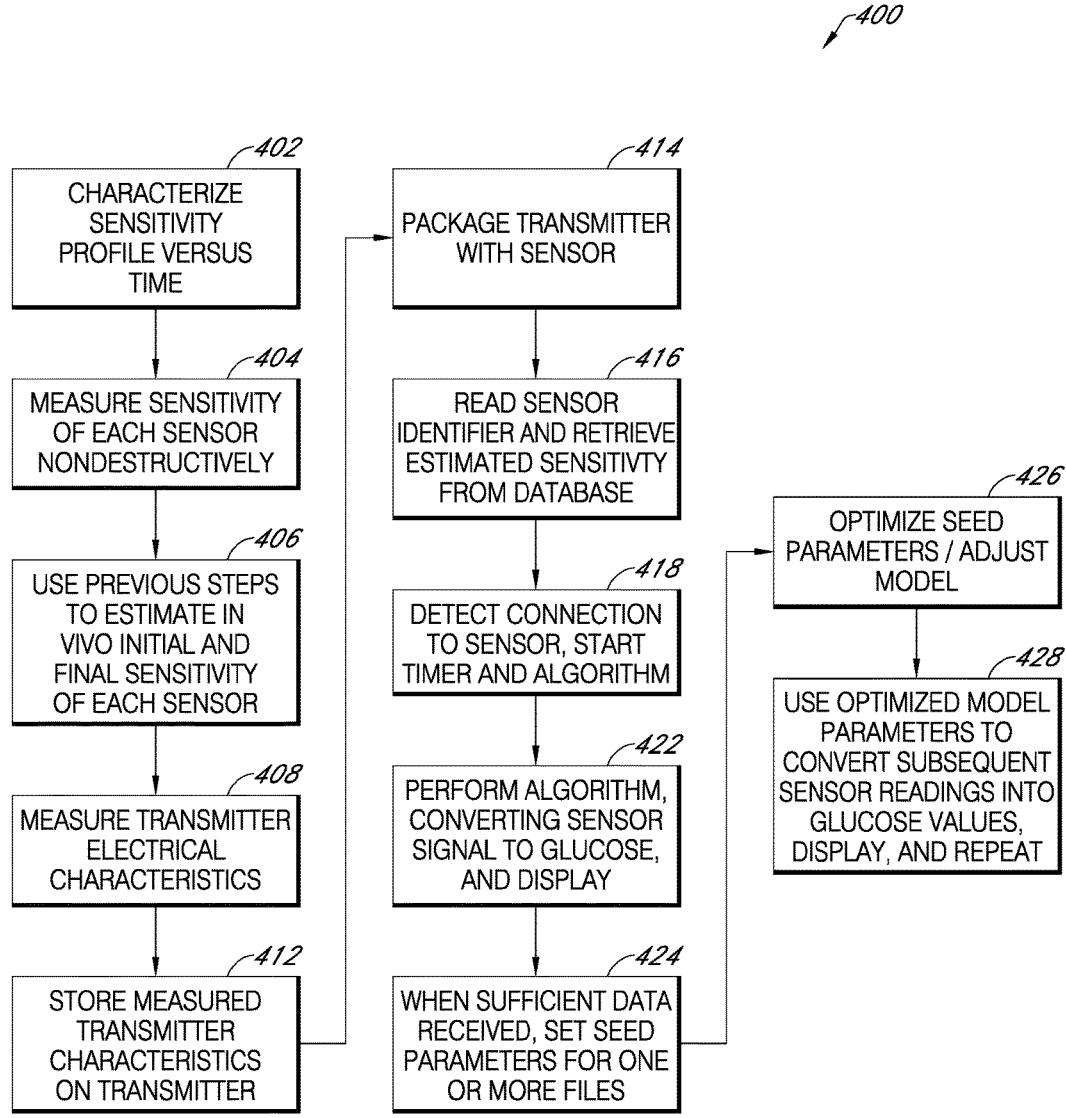
FIG. 47 is a flowchart illustrating another implementation of a method according to present principles.

An exemplary calibration routine is now described, steps of which may be seen in the flowchart 400 of FIG. 47. In a first step, a sensitivity profile versus time is characterized with a bench test that measures the sensor's response in a glucose solution for one or more days (step 402). As this is commonly a destructive test, the same may be run on a representative set of sensors from a manufacturing lot or manufacturing line. This test may be repeated periodically or when the process changes, such as when there are changes in the raw materials or equipment. The sensitivity of each sensor may then be measured with a nondestructive bench test (step 404). The results of steps 402 and 404 are used to estimate the in-vivo initial and final sensitivity of each sensor (step 406).

It is noted here that the destructive tests measure the long-term drift for a group of sensors, e.g., determining that the sensors drift 10% across the first two days. The nondestructive bench test provides a starting point for each sensor in the log, e.g., that a subject sensor may have a starting sensitivity of 20. Combining the two tests, it can be determined that, e.g., the subject sensor starts at 20 and is expected to drift 10%, e.g., to 22.

Thus, this step maps or transforms bench values into in-vivo values with a function that was trained or optimized on well characterized in-vivo data, like clinical trials. As another example, the subject sensor may start at 24 and drift to 26 in-vivo.

The transmitter's electrical characteristics (such as gain and offset) are calibrated during manufacturing (step 408) and these calibration factors are stored on the transmitter (step 412) so that the raw sensor signal can be corrected for part-to-part differences in the electronics before running the algorithm.

A sensor is then packaged with a single-use transmitter (step 414). The sensor's identifier, e.g., identification number, is read with an optical bar code and its estimated in-vivo sensitivity are retrieved from a manufacturing database and written to the transmitter using, e.g., wireless (NFC or Bluetooth®) communication (step 416).

When the transmitter first detects that it is connected to a functioning sensor a session timer is started and the algorithm starts (step 418). The algorithm starts converting the sensor signal to glucose (step 420) using the CGM model with model parameters set to the prior information about sensor sensitivity recorded in step 416.

When a representative set of signal data, e.g., 24 hours, is available, the seed parameters for forward and reverse filters may be set using the median signal value and assumed drift amount (step 422). These seed values are then further optimized to minimize the mean squared error between the two signal filters (step 424).

A signal-based calibration algorithm uses the average of the forward and reverse filter signal and the also the raw sensor signal, and in so doing, adjusts the model parameters, e.g., sensitivity and baseline, to meet several criteria (step 426). In so doing, time-based input data is employed to update the algorithm. An exemplary signal-based calibration algorithm is that disclosed in the patent application incorporated by reference above (Ser. No. 13/827,119), and in particular at [0188], i.e., Example 4, which illustrates a Bayesian learning approach for drift estimation and correction.

In the implementation of FIG. 47, the model is adjusted to meet a criterion that the mean glucose value is consistent with the expected diabetic mean, and may further be adjusted to meet another criterion that the CGM glucose variability is consistent with the mean glucose level. To calculate these metrics, the algorithm has an assumed relationship between mean glucose and glucose variability. For example, a nondiabetic can have a mean glucose level of 85 mg/dL and a standard deviation of 15 mg/dL. A diabetic could have a mean glucose of 170 mg/dL and a standard deviation of 65 mg/dL.

The optimized model parameters are used by the CGM model to convert subsequent sensor readings into glucose values (step 428), which are then displayed.

Steps 424 to 428 are repeated when a new set of signal data is available.

A similar method may be used to detect an unacceptable amount of sensor change (typically a loss of sensitivity from day 7 onwards) and to stop displaying potentially inaccurate readings.

In one preferred embodiment, the analyte sensor is an implantable glucose sensor, such as described with reference to U.S. Pat. No. 6,001,067 and U.S. Patent Publication No. US-2005-0027463-A1. In another preferred embodiment, the analyte sensor is a transcutaneous glucose sensor, such as described with reference to U.S. Patent Publication No. US-2006-0020187-A1. In still other embodiments, the sensor is configured to be implanted in a host vessel or extracorporeally, such as is described in U.S. Patent Publication No. US-2007-0027385-A1, co-pending U.S. patent application Ser. No. 11/543,396 filed Oct. 4, 2006, co-pending U.S. patent application Ser. No. 11/691,426 filed on Mar. 26, 2007, and co-pending U.S. patent application Ser. No. 11/675,063 filed on Feb. 14, 2007. In one alternative embodiment, the continuous glucose sensor comprises a transcutaneous sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al.

The connections between the elements shown in the figures illustrate exemplary communication paths. Additional communication paths, either direct or via an intermediary, may be included to further facilitate the exchange of information between the elements. The communication paths may be bi-directional communication paths allowing the elements to exchange information.

The various operations of methods described above may be performed by any suitable means capable of performing the operations, such as various hardware and/or software component(s), circuits, and/or module(s). Generally, any operations illustrated in the figures may be performed by corresponding functional means capable of performing the operations.

The various illustrative logical blocks, modules and circuits described in connection with the present disclosure (such as the blocks of FIGS. 2 and 4) may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise various types of RAM, ROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. Thus, in some aspects a computer readable medium may comprise non-transitory computer readable medium (e.g., tangible media). In addition, in some aspects a computer readable medium may comprise transitory computer readable medium (e.g., a signal). Combinations of the above should also be included within the scope of computer-readable media.

The methods disclosed herein comprise one or more steps or actions for achieving the described methods. The method steps and/or actions may be interchanged with one another without departing from the scope of the claims. In other words, unless a specific order of steps or actions is specified, the order and/or use of specific steps and/or actions may be modified without departing from the scope of the claims.

Certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention, e.g., as including any combination of the listed items, including single members (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All references cited herein are incorporated herein by reference in their entirety. To the extent publications and patents or patent applications incorporated by reference contradict the disclosure contained in the specification, the specification is intended to supersede and/or take precedence over any such contradictory material.

Headings are included herein for reference and to aid in locating various sections. These headings are not intended to limit the scope of the concepts described with respect thereto. Such concepts may have applicability throughout the entire specification.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of calibrating an analyte concentration sensor within a biological system, using a signal from the analyte concentration sensor, wherein at a steady state, the analyte concentration value within the biological system is known, comprising:
    on a monitoring device, receiving a seed value of a calibration parameter;
    on the monitoring device, detecting when an analyte concentration value as measured by an analyte concentration sensor indwelling in a biological system is at a steady state; and
    on the monitoring device or on a device or server operatively coupled to the monitoring device, correlating a measurement of the analyte concentration value when the biological system is at the detected steady state to the known analyte concentration value;
    subsequent to the correlating, receiving a signal from the sensor; and
    calculating and displaying a value corresponding to the received signal, the calculated value based on the received signal, the known analyte concentration value, and the seed value.

2. The method of claim 1, wherein the received seed value is received from a source including factory calibration information.

3. The method of claim 1, further comprising:
    detecting a behavior in the received signal outside of a pre-prescribed parameter; and
    prompting a user to enter external calibration information.

4. The method of claim 3, wherein the displayed value is further based on the external calibration information.

5. The method of claim 3, wherein the external calibration information is received from an SMBG or a fingerstick calibration.

6. The method of claim 3, further comprising resetting the known calibration value to a new known calibration value, the resetting based at least partially on the external calibration information.

7. The method of claim 3, further comprising resetting the seed value to a new seed value, the resetting based at least partially on the external calibration information.

8. The method of claim 1, further comprising altering the display based on a determined accuracy of the value.

9. The method of claim 8, wherein the altering the displaying includes displaying a range rather than a value, or vice versa.

10. The method of claim 1, wherein the received seed value of a calibration parameter is a user-entered characterization of disease state.

11. The method of claim 10, wherein the user entered characterization of disease state includes an indication of type I diabetes, type II diabetes, nondiabetic, or prediabetic.

12. The method of claim 1, wherein the received seed value of a calibration parameter is a value based on one or more user-entered blood glucose values.

13. The method of claim 1, wherein the displaying of a value corresponding to the received signal includes displaying a graph or table indicating currently measured and historic values of the analyte concentration, and further comprising:
  detecting that a change in calibration has occurred;
  adjusting one or more calibration parameters of the analyte concentration sensor according to the change in calibration; and
  following the adjusting, updating the display of the graph or table indicating currently measured and historic values of the analyte concentration according to the adjusted calibration parameters.

14. The method of claim 13, wherein the detecting that a change in calibration has occurred includes:
  detecting a change in a slow-moving average; or
  detecting a change in the steady state value.

15. The method of claim 13, wherein the adjusting is configured to occur at a time when a sensor reading is substantially stable, or within a predetermined range of readings for a threshold period of time, whereby an occurrence of unexpected jumps in readings is reduced.

16. An analyte concentration sensor system, comprising:
  an analyte concentration sensor configured to be calibrated within a biological system, using a signal from the analyte concentration sensor, wherein at a steady state, the analyte concentration value within the biological system is known;
  a processor comprising a component of a monitoring device or a device or server operatively connected to the monitoring device, wherein the processor is configured to:
    receive a seed value of a calibration parameter;
    detect when an analyte concentration value as measured by the analyte concentration sensor indwelling in a biological system is at a steady state;
    correlate a measurement of the analyte concentration value when the biological system is at the detected steady state to the known analyte concentration value; thereafter receive a signal from the sensor; and
    calculate a value corresponding to the received signal, the calculated value based on the received signal, the known analyte concentration value, and the seed value; and
  a display device, wherein the display device is configured to display the calculated value.

17. The system of claim 16, wherein the received seed value is received from a source including factory calibration information.

18. The system of claim 16, wherein the processor is configured to:
  detect a behavior in the received signal outside of a pre-prescribed parameter; and
  prompt a user to enter external calibration information.

19. The system of claim 18, wherein the processor is configured to reset the known calibration value to a new known calibration value based at least partially on the external calibration information.

20. The system of claim 18, wherein the processor is configured to reset the seed value to a new seed value based at least partially on the external calibration information.

21. The system of claim 16, wherein the processor is configured to alter the display based on a determined accuracy of the value.

22. The system of claim 16, wherein the display device is configured to display a graph or table indicating currently measured and historic values of the analyte concentration, and wherein the processor is further configured to:
  detect that a change in calibration has occurred;
  adjust one or more calibration parameters of the analyte concentration sensor according to the change in calibration; and thereafter
  update the display of the graph or table indicating currently measured and historic values of the analyte concentration according to the adjusted calibration parameters.

23. The system of claim 22, wherein the processor is configured to detect that a change in calibration has occurred by detecting a change in a slow-moving average or detecting a change in the steady state value.

24. The system of claim 16, wherein the processor is configured to adjust one or more calibration parameters at a time when a sensor reading is substantially stable, or within a predetermined range of readings for a threshold period of time, whereby an occurrence of unexpected jumps in readings is reduced.

* * * * *

UNITED STATES PATENT AND TRADEMARK OFFICE
CERTIFICATE OF CORRECTION

PATENT NO. : 10,470,661 B2
APPLICATION NO. : 15/261816
DATED : November 12, 2019
INVENTOR(S) : Arturo Garcia et al.

Page 1 of 1

It is certified that error appears in the above-identified patent and that said Letters Patent is hereby corrected as shown below:

In the Specification

In Column 13, Line 14, delete "andrenostenedione;" and insert -- androstenedione; --.

In Column 13, Line 37, delete "perioxidase;" and insert -- peroxidase; --.

In Column 13, Line 46, delete "sissomicin;" and insert -- sisomicin; --.

In Column 13, Line 50, delete "duodenalisa," and insert -- duodenalis, --.

In Column 13, Line 58, delete "Trepenoma pallidium," and insert -- Treponema pallidum, --.

In Column 13, Line 59, delete "stomatis" and insert -- stomatitis --.

In Column 27, Line 46, delete "sensitivity)," and insert -- sensitivity, --.

Signed and Sealed this
Third Day of March, 2020

Andrei Iancu
*Director of the United States Patent and Trademark Office*